(12) United States Patent
Hitchcock et al.

(10) Patent No.: US 9,303,045 B2
(45) Date of Patent: Apr. 5, 2016

(54) 5-HT3 RECEPTOR ANTAGONISTS

(71) Applicant: Takeda Pharmaceutical Company Limited, San Diego, CA (US)

(72) Inventors: Stephen Hitchcock, San Diego, CA (US); Holger Monenschein, San Diego, CA (US); Holly Reichard, San Diego, CA (US); Huikai Sun, San Diego, CA (US); Shota Kikuchi, San Diego, CA (US); Todd Macklin, San Diego, CA (US); Maria Hopkins, San Diego, CA (US)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 14/415,712

(22) PCT Filed: Jul. 16, 2013

(86) PCT No.: PCT/US2013/050762
§ 371 (c)(1),
(2) Date: Jan. 19, 2015

(87) PCT Pub. No.: WO2014/014962
PCT Pub. Date: Jan. 23, 2014

(65) Prior Publication Data
US 2015/0291624 A1    Oct. 15, 2015

(51) Int. Cl.
| | | |
|---|---|---|
| C07D 471/04 | (2006.01) |
| C07D 498/04 | (2006.01) |
| A61K 31/537 | (2006.01) |
| C07D 519/00 | (2006.01) |
| C07D 498/08 | (2006.01) |
| C07D 451/12 | (2006.01) |
| A61K 31/19  | (2006.01) |
| A61K 31/5386| (2006.01) |
| C07D 221/22 | (2006.01) |

(52) U.S. Cl.
CPC ............. *C07D 519/00* (2013.01); *A61K 31/19* (2013.01); *A61K 31/5386* (2013.01); *C07D 221/22* (2013.01); *C07D 451/12* (2013.01); *C07D 471/04* (2013.01); *C07D 498/08* (2013.01)

(58) Field of Classification Search
CPC .. C07D 471/04; C07D 519/00; C07D 498/04; A61K 31/537
USPC ............................. 546/121; 544/105; 514/299
See application file for complete search history.

(56) References Cited

U.S. PATENT DOCUMENTS

| | | |
|---|---|---|
| 4,789,673 A | 12/1988 | Donatsch et al. |
| 4,803,199 A | 2/1989 | Donatsch et al. |
| 4,886,808 A | 12/1989 | King et al. |
| 4,910,193 A | 3/1990 | Buchheit et al. |
| 4,948,803 A | 8/1990 | Tyers |
| 5,017,573 A | 5/1991 | Kon et al. |
| 5,034,398 A | 7/1991 | King et al. |
| 5,298,510 A | 3/1994 | Tyers |
| 5,344,831 A | 9/1994 | Satoh et al. |
| 5,684,003 A | 11/1997 | Kikuchi et al. |
| 2004/0038958 A1 | 2/2004 | Rundfeldt et al. |
| 2005/0234095 A1 | 10/2005 | Xie et al. |
| 2007/0191313 A1 | 8/2007 | Beard et al. |
| 2010/0113405 A1 | 5/2010 | Gant et al. |
| 2011/0319407 A1 | 12/2011 | Xie et al. |
| 2012/0101094 A1 | 4/2012 | Xie et al. |
| 2012/0190680 A1* | 7/2012 | Bakthavatchalam .. B64D 33/04 514/234.5 |

FOREIGN PATENT DOCUMENTS

| | | |
|---|---|---|
| EP | 020044 | 5/1986 |
| EP | 0223385 | 5/1987 |
| EP | 0469449 | 2/1992 |
| EP | 0491664 | 6/1992 |
| EP | 0708105 | 4/1996 |
| EP | 1156045 | 11/2001 |
| EP | 1243268 | 9/2002 |

(Continued)

OTHER PUBLICATIONS

Naghdi et al. "The effect of intrahippocampal injections of ritanserin (5HT2A/2C antagonist) and granisetron (5HT3 antagonist) on learning as assessed in the spatial version of the water maze" Behavioural Brain Research 157 (2005) p. 205-210.

(Continued)

*Primary Examiner* — Niloofar Rahmani
(74) *Attorney, Agent, or Firm* — Matthew J. Russo; David M. Stemerick

(57) ABSTRACT

The present invention provides compounds of the formula:

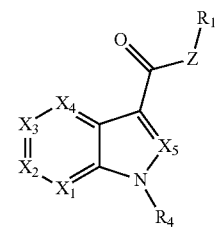

that are 5HT3 receptor antagonists and are therefore useful for the treatment of diseases treatable by inhibition of 5HT3 receptor such as emesis, pain, drug addiction, neurodegenerative and psychiatric disorders, and GI disorders. Also provided are pharmaceutical compositions containing such compounds and processes for preparing such compounds.

11 Claims, No Drawings

(56) References Cited

FOREIGN PATENT DOCUMENTS

| WO | WO/95/27490 | 10/1995 |
| WO | WO/03/035625 | 5/2003 |
| WO | WO/2004/029050 | 4/2004 |
| WO | WO/2004/089470 | 10/2004 |
| WO | WO/2005/092890 | 10/2005 |
| WO | WO/2006/077365 | 7/2006 |
| WO | WO/2007/038367 | 4/2007 |
| WO | WO/2007/095561 | 8/2007 |
| WO | WO/2008/048981 | 4/2008 |
| WO | WO/2008/097930 | 8/2008 |
| WO | WO/2009/023623 | 2/2009 |
| WO | WO/2009/108551 | 9/2009 |

OTHER PUBLICATIONS

Bermudez, Jose et al. "5-Hydroxytryptamine (5HT3) Receptor Antagonist. 1. Indazole and Indolzine-3-carboxylic Acid Derivatives" J. Med. Chem 1990, 33, p. 1924-29.

* cited by examiner

5-HT3 RECEPTOR ANTAGONISTS

CROSS-REFERENCE TO RELATED APPLICATIONS

This application is the U.S. National Stage entry under 35 U.S.C. §371(c) of International Application PCT/US2013/050762, filed Jul. 16, 2013, which claims the benefit of U.S. Provisional Application No. 61/708,521, filed Oct. 1, 2012, and U.S. Provisional Application No. 61/672,709, filed Jul. 17, 2012, which is herein incorporated by reference.

FIELD OF INVENTION

The present invention provides compounds that are 5HT3 receptor antagonists and are therefore useful for the treatment of diseases treatable by inhibition of the 5HT3 receptor such as emesis, pain, drug addiction, neurodegenerative and psychiatric disorders, and GI disorders. Also provided are pharmaceutical compositions containing such compounds and processes for preparing such compounds.

BACKGROUND

Serotonin type 3 (5HT3) receptors are part of the serotonergic system. Unlike other receptors of this system, which are all G-protein coupled receptors, the 5HT3 receptors are ligand-gated ion channels and belongs to the superfamily of Cys-loop receptors that include nicotinic acetylcholine, γ-aminobutyric acid (GABA)A and glycine receptors and a Zn+2 activated cation channel (see Davies et al., 2003, *J. Biol. Chem.*, 278, 712-717; Connolly et al., 2004, *Biochem Soc Trans* 32, 529-534). The $5HT_3$ receptors are made up of 5 subunits arranged around a central ion conducting pore, which is permeable to sodium, potassium, and calcium ions (see Boess et al., 1995, *J. Neurochem.* 64, 1401-1405; Connolly et al., 2004, *Biochem Soc Trans* 32, 529-534). Binding of serotonin to the $5HT_3$ receptors opens the channel, which, in turn, leads to an excitatory response in neurons. Functional data reported for 5HT3 receptors refer to 5HT3A or 5HT3AB receptors since the properties of these receptor subtypes have been most extensively studies to date.

5HT3 receptors are known to be expressed in the central nervous system in regions involving vomiting reflex, processing of pain, cognition and anxiety control and play a role in the pathogenesis of diseases such as emesis, migraine, drug addiction, and neurodegenerative and psychiatric disorders such as anxiety and depression (see Hewlett et al., 2003 *J. Clin. Psychiatry* 64, 1025-1030; Kelley et al., 2003a, *Eur J. Pharmacol.*, 461, 19-25; Haus et al., 2000 *Scand J Rheumatol Suppl* 113, 55-58; and Faris et al., 2006 *J affect Disorder* 92, 79-90), eating disorders (Hammer et al., 1990 *Am J Physiol* 259, R627-R636, and Jiang & Gietzen 1994 *Pharmacol Biochem Behav* 47, 59-63), schizophrenia (see Hermann et al. 1996 *Biochem Biophys Res Commun* 225, 957-960; Sirota et al., 2000 *Am J Psychiatry* 157, 287-289; Adler et al., 2005 *Am J Psychiatry* 162, 386-388; Koike et al., Levkovitz et al, 2005 *Schizophr Res* 76, 67-72), cognitive dysfunction associated with schizophrenia (see Zhang et al., 2006 *Schizophr Res* 88, 102-110; Akhondzadeh et al., 2009 *Schizophr Res* 107, 206-212), cognitive dysfunction associated with Parkinson's disease, Huntington's Chorea, presenile dementias and Alzheimer's disease (see Costall and Naylor 2004 *CNS Neurol Disord* 3, 27-37) substance abuse and addiction (see Johnson et al., 2002 *Psycho-pharmacology* (Berl) 160, 408-413; Johnson, 2004 *CNS Drugs* 18, 1105-1118; Dawes et al., 2005 *Addict Behav* 30, 1630-1637, Johnson 2006 *Drug Alcohol Depend* 84, 256-263), autish spectrum disorders (see Anderson et al *Neurogenetics* 10, 209-216) and pain (see Kayser et al, 2007 *Pain* 130, 235; Glaum et al., 1998 *Neurosci Lett* 95, 313-317; Schworer & Ramadori 1993 *Clin Investig* 71, 659; Thompson and Lummis 2007 *Exp Opin Ther Targets*, 11, 527-540). In addition, 5HT3 receptors are expressed in the GI tract and hence may play a role in GI disorders such as dyspepsia, gastroesophagal reflux disease and irritable bowel syndrome (see Graeff 1997 *Psychiatr Clin North Am* 20, 723; Thompson and Lummis 2007 *Exp Opin Ther Targets*, 11, 527-540; Barnes et al. 2009 *Neuropharmacology* 56, 273). Expression of the 5HT3A subunit has also been discovered extraneuronally in immune cells such as monocytes, chondrocytes, T-cells, synovial tissue and platelets (Fiebich et al., 2004 *Scan J Rheumatol Suppl*, 9-11, Stratz et al., 2008 *Thromb Haemost* 99, 784) and of 5HT3A, C-E within the lamina propia in the epithelium of the gut mucose (Kapeller et al., J Comp Neuro., 2008; 509: 356-371) thus suggesting they may be involved in immunological and inflammatory diseases like atherosclerosis, tendomyopathies and fibromyalgia.

The 5HT3 antagonists currently on the market are approved only for the treatment of emesis or irritable bowel syndrome. It is desirable to discover 5HT3 antagonists that can be used to treat other diseases amenable to alleviation by 5HT3 receptors such as schizophrenia and cognitive disorder associated with schizophrenia. The present invention can fulfill this and related needs. It is desirable to discover 5HT3 antagonists that have desirable pharmacokinetic and pharmacodynamic properties, such as selectivity over nicotinic-α7 receptors.

Certain antagonists the 5HT3 receptor are described in U.S. Pat. Nos. 4,789,763; 4,803,199; 4,886,808; 4,910,193; 5,334,831; EP 0 469 449; and EP 0 491 664. Certain inhibitors of TGF-β are described in EP 1 156 045 and certain treatment of nephritis is described in EP1 243 268. Certain antagonists of 5HT4 are described in EP 0 708 105. Certain ligands of nicotinic-α7 receptors are described in WO 2007/038367. Certain P2X7 antagonists are disclosed in WO 2009/023623.

SUMMARY

In a first aspect, this invention is directed to a compound of Formula (IA):

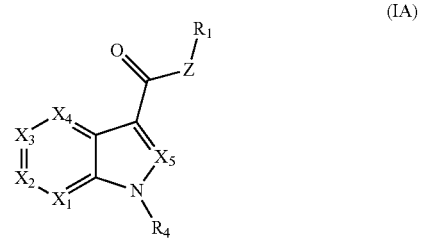

(IA)

wherein:

Z is O or $NR_a$;

$R_a$ is hydrogen or $C_{1-6}$ alkyl;

$R_1$ is a ring of the formula (a)-(h) below:

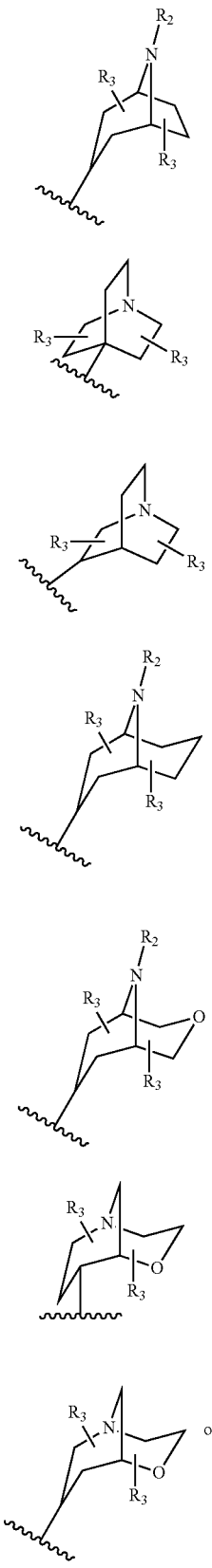

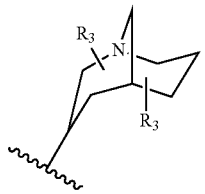

wherein:

$R_2$ is hydrogen, $C_{1-6}$ alkyl, or $C_{1-6}$ haloalkyl;

each $R_3$ is independently hydrogen, $C_{1-6}$ alkyl, $C_{1-6}$ alkoxy, $C_{1-6}$ haloalkoxy, or halo and can be present on any carbon atom in the rings;

$R_4$ is $C_{1-6}$ haloalkyl; $C_{1-6}$ cyanoalkyl; $C_{1-6}$ alkylsulfonyl; $C_{3-8}$ cycloalkylsulfonyl; heteroaryl selected from the group consisting of furanyl, thienyl, pyrrolyl, imidazolyl, oxazolyl, isoxazolyl, oxadiazolyl, thiazolyl, isothiazolyl, thiadiazolyl, triazolyl, tetrazolyl, pyrazinyl, pyridazinyl, pyrimidyl, azepinyl, diazepinyl, quinolyl, isoquinolyl, quinolizidine, benzofuranyl, benzothienyl, indolyl, isoindolyl, indazolyl, benzimidazolyl, benzisothiazolyl, benzisoxazolyl, benzoxadiazolyl, benzoxazolyl, benzothiazolyl, benzothiadiazolyl, benzotriazolyl, benzopyrazinyl, benzopyrazidinyl, benzoazepinyl, benzodiazepinyl, imidazopyridyl, pyrazolopyridyl, pyrrolopyridyl, quinazolyl, purinyl, furopyridyl, and thienopyridyl, each $R_4$ heteroaryl is optionally substituted with one or two substituents independently selected from $C_{1-6}$ alkyl, $C_{1-6}$ haloalkyl, $C_{1-6}$ haloalkoxy, $C_{1-6}$ alkoxy, hydroxy, cyano, or halo; $C_{3-6}$ heterocycloalkyl optionally substituted with one or two substituents independently selected from $C_{1-6}$ alkyl, $C_{1-6}$ alkoxy, $C_{1-6}$ haloalkoxy, $C_{1-6}$ alkylsulfonyl, or halo; $C_{3-6}$ oxoheterocycloalkyl optionally substituted with one or two substituents independently selected from $C_{1-6}$ alkyl, $C_{1-6}$ alkoxy, $C_{1-6}$ haloalkoxy, $C_{1-6}$ alkylsulfonyl, or halo; or phenyl optionally substituted with one, two, or three substituents independently selected from $C_{1-6}$ alkyl, $C_{1-6}$ haloalkyl, $C_{1-6}$ haloalkoxy, $C_{1-6}$ alkoxy, hydroxyl, cyano, or halo;

all of $X_1$-$X_4$ are $CR_5$ or one of $X_1$-$X_4$ is N and the others are $CR_5$;

each $R_5$ is independently hydrogen, $C_{1-6}$ alkyl, halo, hydroxy, or cyano provided that at least one of $R_5$ is hydrogen;

$X^5$ is N or $CR^6$ where $R^6$ is hydrogen, $C_{1-6}$ alkyl, or halo or $R^6$ together with $R^4$ and atoms to which they are attached form —O—$(CH_2)_2$—, —O—$(CH_2)_3$—, or —O—$(CH_2)_4$—;

or a pharmaceutically acceptable salt thereof or N-oxide thereof and provided that the compound of Formula (IA) is not:

N-(3)-1-azabicyclo[2.2.2]oct-3-yl-6-bromo-1-(difluoromethyl)-1H-indazole-3-carboxamide, N-(3)-1-azabicyclo[2.2.2]oct-3-yl-1-(difluoromethyl)-6-methoxy-1H-indazole-3-carboxamide, N-(3)-1-azabicyclo[2.2.2]oct-3-yl-5-bromo-1-(2,2,2-trifluoroethyl)-1H-indazole-3-carboxamide, N-(3)-1-azabicyclo[2.2.2]oct-3-yl-5-methoxy-1-(2,2,2-trifluoroethyl)-1H-indazole-3-carboxamide, or N-(3)-1-azabicyclo[2.2.2]oct-3-yl-1-(3-thienyl)-1H-indazole-3-carboxamide.

In one embodiment of the first aspect, the compounds have Formula (I):

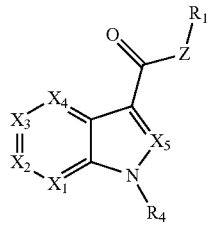
(I)

wherein:

Z is O or $NR_a$;

$R_a$ is hydrogen or $C_{1-6}$ alkyl;

$R_1$ is a ring of the formula (a)-(h) below:

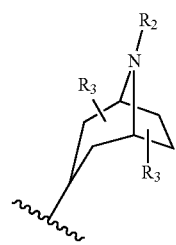
(a)

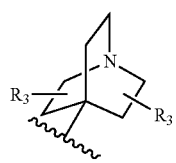
(b)

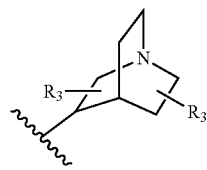
(c)

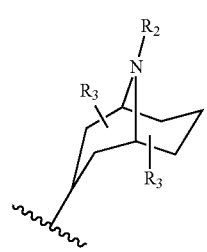
(d)

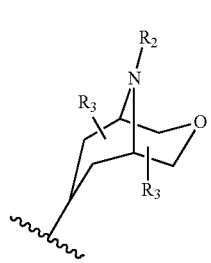
(e)

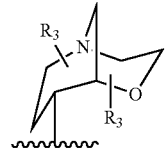
(f)

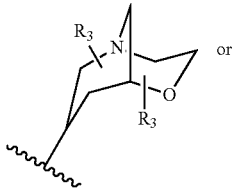
(g)

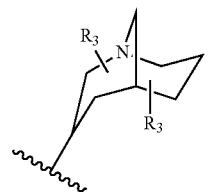
(h)

wherein:

$R_2$ is hydrogen, $C_{1-6}$ alkyl, or $C_{1-6}$ haloalkyl;

each $R_3$ is independently hydrogen, $C_{1-6}$ alkyl, $C_{1-6}$ alkoxy, $C_{1-6}$ haloalkoxy, or halo and can be present on any carbon atom in the rings;

$R_4$ is heteroaryl selected from the group consisting of furanyl, thienyl, pyrrolyl, imidazolyl, oxazolyl, isoxazolyl, oxadiazolyl, thiazolyl, isothiazolyl, thiadiazolyl, triazolyl, tetrazolyl, pyrazinyl, pyridazinyl, pyrimidyl, azepinyl, diazepinyl, quinolyl, isoquinolyl, quinolizidine, benzofuranyl, benzothienyl, indolyl, isoindolyl, indazolyl, benzimidazolyl, benzisothiazolyl, benzisoxazolyl, benzoxadiazolyl, benzoxazolyl, benzothiazolyl, benzothiadiazolyl, benzotriazolyl, benzopyrazinyl, benzopyrazidinyl, benzoazepinyl, benzodiazepinyl, imidazopyridyl, pyrazolopyridyl, pyrrolopyridyl, quinazolyl, purinyl, furopyridyl, and thienopyridyl; each $R_4$ heteroaryl is optionally substituted with one or two substituents independently selected from $C_{1-6}$ alkyl, $C_{1-6}$ haloalkyl, $C_{1-6}$ haloalkoxy, $C_{1-6}$ alkoxy, hydroxy, cyano, or halo;

all of $X_1$-$X_4$ are $CR_5$ or one of $X_1$-$X_4$ is N and the others are $CR_5$;

each $R_5$ is independently hydrogen, $C_{1-6}$ alkyl, halo, hydroxy, or cyano provided that at least one of $R_5$ is hydrogen;

$X^5$ is N or $CR^6$ where $R^6$ is hydrogen, $C_{1-6}$ alkyl, or halo or $R^6$ together with $R^4$ and atoms to which they are attached form —O—$(CH_2)_2$—, —O—$(CH_2)_3$—, or —O—$(CH_2)_4$—;

or a pharmaceutically acceptable salt thereof or N-oxide thereof and provided that the compound of Formula (I) is not: N-(3)-1-azabicyclo[2.2.2]oct-3-yl-1-(3-thienyl)-1H-Indazole-3-carboxamide.

In a second aspect, this present invention is directed to a pharmaceutical composition comprising a compound of Formula (IA) or (I) (or any embodiments thereof disclosed herein) or a pharmaceutically acceptable salt thereof and a pharmaceutically acceptable excipient; provided the compound of Formula (IA) is not N-(3)-1-azabicyclo[2.2.2]oct-3-yl-6-bromo-1-(difluoromethyl)-1H-Indazole-3-carboxamide, N-(3)-1-azabicyclo[2.2.2]oct-3-yl-1-(difluoromethyl)-6-methoxy-1H-Indazole-3-carboxamide, N-(3)-1-azabicyclo[2.2.2]oct-3-yl-5-bromo-1-(2,2,2-trifluoroethyl)-

1H-Indazole-3-carboxamide, N-(3)-1-azabicyclo[2.2.2]oct-3-yl-5-methoxy-1-(2,2,2-trifluoroethyl)-1H-Indazole-3-carboxamide, or N-(3)-1-azabicyclo[2.2.2]oct-3-yl-1-(3-thienyl)-1H-Indazole-3-carboxamide or the compound of Formula (I) is not N-(3)-1-azabicyclo[2.2.2]oct-3-yl-1-(3-thienyl)-1H-Indazole-3-carboxamide; individual stereoisomers, or a pharmaceutically acceptable salt thereof.

In a third aspect, this present invention is directed to a method of treating a disease treatable by administration of a 5HT3 receptor antagonist which method comprises administrating to the patient a pharmaceutical composition comprising a compound of Formula (IA) or (I) (or any embodiments thereof disclosed herein) and/or a pharmaceutically acceptable salt and a pharmaceutically acceptable excipient provided the compound of Formula (IA) is not N-(3)-1-azabicyclo[2.2.2]oct-3-yl-6-bromo-1-(difluoromethyl)-1H-Indazole-3-carboxamide, N-(3)-1-azabicyclo[2.2.2]oct-3-yl-1-(difluoromethyl)-6-methoxy-1H-Indazole-3-carboxamide, N-(3)-1-azabicyclo[2.2.2]oct-3-yl-5-bromo-1-(2,2,2-trifluoroethyl)-1H-Indazole-3-carboxamide, N-(3)-1-azabicyclo[2.2.2]oct-3-yl-5-methoxy-1-(2,2,2-trifluoroethyl)-1H-Indazole-3-carboxamide, or N-(3)-1-azabicyclo[2.2.2]oct-3-yl-1-(3-thienyl)-1H-Indazole-3-carboxamide or the compound of Formula (I) is not N-(3)-1-azabicyclo[2.2.2]oct-3-yl-1-(3-thienyl)-1H-Indazole-3-carboxamide. That is, In a the present invention provides a method of treating a disease treatable by administration of a 5HT3 receptor antagonist comprising: administrating to the patient in need thereof an effective amount of a compound of Formula (IA) or (I) (or any embodiments thereof disclosed herein) or a pharmaceutically acceptable salt thereof provided the compound of Formula (IA) is not N-(3)-1-azabicyclo[2.2.2]oct-3-yl-6-bromo-1-(difluoromethyl)-1H-Indazole-3-carboxamide, N-(3)-1-azabicyclo[2.2.2]oct-3-yl-1-(difluoromethyl)-6-methoxy-1H-Indazole-3-carboxamide, N-(3)-1-azabicyclo[2.2.2]oct-3-yl-5-bromo-1-(2,2,2-trifluoroethyl)-1H-Indazole-3-carboxamide, N-(3)-1-azabicyclo[2.2.2]oct-3-yl-5-methoxy-1-(2,2,2-trifluoroethyl)-1H-Indazole-3-carboxamide, or N-(3)-1-azabicyclo[2.2.2]oct-3-yl-1-(3-thienyl)-1H-Indazole-3-carboxamide or the compound of Formula (I) is not N-(3)-1-azabicyclo[2.2.2]oct-3-yl-1-(3-thienyl)-1H-Indazole-3-carboxamide.

In one embodiment of the third aspect, the disease is emesis, migraine, substance abuse and addiction, neurodegenerative and psychiatric disorders such as anxiety and depression, eating disorders, schizophrenia, cognitive dysfunction associated with schizophrenia, Parkinson's disease, Huntington's Chorea, presenile dementias and Alzheimer's disease, and pain; GI disorders such as dyspepsia, gastroesophagal reflux disease, and irritable bowel syndrome; and immunological disorders and inflammation such as atherosclerosis, tendomyopathies and fibromyalgia. In another embodiment of the third aspect the disease is schizophrenia or cognitive dysfunction associated with schizophrenia.

In a fourth aspect, the compound of Formula (IA) or (I) (or any embodiments thereof disclosed herein) or a pharmaceutically acceptable salt thereof is administered in combination with an antipsychotic drug provided the compound of Formula (IA) is not N-(3)-1-azabicyclo[2.2.2]oct-3-yl-6-bromo-1-(difluoromethyl)-1H-Indazole-3-carboxamide, N-(3)-1-azabicyclo[2.2.2]oct-3-yl-1-(difluoromethyl)-6-methoxy-1H-Indazole-3-carboxamide, N-(3)-1-azabicyclo[2.2.2]oct-3-yl-5-bromo-1-(2,2,2-trifluoroethyl)-1H-Indazole-3-carboxamide, N-(3)-1-azabicyclo[2.2.2]oct-3-yl-5-methoxy-1-(2,2,2-trifluoroethyl)-1H-Indazole-3-carboxamide, or N-(3)-1-azabicyclo[2.2.2]oct-3-yl-1-(3-thienyl)-1H-Indazole-3-carboxamide or the compound of Formula (I) is not N-(3)-1-azabicyclo[2.2.2]oct-3-yl-1-(3-thienyl)-1H-Indazole-3-carboxamide. In one embodiment of the fourth aspect, the antipsychotic drug is AMG 747, bitopertin (RG1678), RG1578, AMG579, GSK1018921, aripiprazole, risperidone, olanzapine, quetiapine, ziprasidone, or clozapine.

In a fifth aspect, the invention is directed to use of compound of Formula (IA) or (I) (or any embodiments thereof disclosed herein) or a pharmaceutically acceptable salt thereof as a medicament; provided the compound of Formula (IA) is not N-(3)-1-azabicyclo[2.2.2]oct-3-yl-6-bromo-1-(difluoromethyl)-1H-Indazole-3-carboxamide, N-(3)-1-azabicyclo[2.2.2]oct-3-yl-1-(difluoromethyl)-6-methoxy-1H-Indazole-3-carboxamide, N-(3)-1-azabicyclo[2.2.2]oct-3-yl-5-bromo-1-(2,2,2-trifluoroethyl)-1H-Indazole-3-carboxamide, N-(3)-1-azabicyclo[2.2.2]oct-3-yl-5-methoxy-1-(2,2,2-trifluoroethyl)-1H-Indazole-3-carboxamide, or N-(3)-1-azabicyclo[2.2.2]oct-3-yl-1-(3-thienyl)-1H-Indazole-3-carboxamide or the compound of Formula (I) is not N-(3)-1-azabicyclo[2.2.2]oct-3-yl-1-(3-thienyl)-1H-Indazole-3-carboxamide; individual stereoisomers, or a pharmaceutically acceptable salt thereof.

In a sixth aspect, the invention is directed to a compound of Formula (IA) or (I) (or any embodiments thereof disclosed herein) or a pharmaceutically acceptable salt thereof for use as medicament; provided the compound of Formula (IA) is not N-(3)-1-azabicyclo[2.2.2]oct-3-yl-6-bromo-1-(difluoromethyl)-1H-Indazole-3-carboxamide, N-(3)-1-azabicyclo[2.2.2]oct-3-yl-1-(difluoromethyl)-6-methoxy-1H-Indazole-3-carboxamide, N-(3)-1-azabicyclo[2.2.2]oct-3-yl-5-bromo-1-(2,2,2-trifluoroethyl)-1H-Indazole-3-carboxamide, N-(3)-1-azabicyclo[2.2.2]oct-3-yl-5-methoxy-1-(2,2,2-trifluoroethyl)-1H-Indazole-3-carboxamide, or N-(3)-1-azabicyclo[2.2.2]oct-3-yl-1-(3-thienyl)-1H-Indazole-3-carboxamide or the compound of Formula (I) is not N-(3)-1-azabicyclo[2.2.2]oct-3-yl-1-(3-thienyl)-1H-Indazole-3-carboxamide; individual stereoisomers, or a pharmaceutically acceptable salt thereof.

In one embodiment of the fifth and sixth aspects, the use is for the treatment of emesis, migraine, substance abuse and addiction, neurodegenerative and psychiatric disorders such as anxiety and depression, eating disorders, schizophrenia, cognitive dysfunction associated with schizophrenia, Parkinson's disease, Huntington's Chorea, presenile dementias and Alzheimer's disease, and pain; GI disorders such as dyspepsia, gastroesophagal reflux disease, and irritable bowel syndrome; and immunological disorders and inflammation such as atherosclerosis, tendomyopathies and fibromyalgia. In another embodiment of the fifth and the sixth aspects the use is for the treatment of schizophrenia or cognitive dysfunction associated with schizophrenia also known as cognitive impairment associated with schizophrenia. In yet another embodiment of the fifth and sixth aspects, and embodiments contained therein, the compound of Formula (IA) or (I) is administered in combination with an antipsychotic drug. In one embodiment, the antipsychotic drug is AMG 747, bitopertin (RG1678), RG1578, AMG579, GSK1018921, aripiprazole, risperidone, olanzapine, quetiapine, or ziprasidone, clozapine.

DETAILED DESCRIPTION OF THE INVENTION

Definitions:

Unless otherwise stated, the following terms used in the specification and claims are defined for the purposes of this application and have the following meaning:

"$C_{1-6}$ alkyl" means a linear saturated monovalent hydrocarbon radical of one to six carbon atoms or a branched saturated monovalent hydrocarbon radical of three to six carbon atoms, e.g., methyl, ethyl, propyl, 2-propyl, butyl (including all isomeric forms), pentyl (including all isomeric forms), and the like.

"$C_{1-6}$ alkoxy" means a —OR radical where R is $C_{1-6}$ alkyl as defined above, e.g., methoxy, ethoxy, propoxy, or 2-propoxy, n-, iso-, or tert-butoxy, and the like.

"$C_{1-6}$ alkylsulfonyl" means a —SO$_2$R radical where R is $C_{1-6}$ alkyl as defined above, e.g., methylsulfonyl, ethylsulfonyl, 2-propylsulfonyl, and the like.

"$C_{3-8}$ cycloalkyl" means a 3 to 8 membered saturated cyclic hydrocarbon radical e.g., cyclopropyl, cyclobutyl, cyclopentyl, cyclohexyl, and the like.

"$C_{3-8}$ cycloalkylsulfonyl" means a —SO$_2$R radical where R is $C_{3-8}$ cycloalkyl as defined above, e.g., cyclopropylsulfonyl, and the like.

"$C_{1-6}$ cyanoalkyl" means $C_{1-6}$ alkyl radical as defined above where one hydrogen atoms in the alkyl radical is replaced by cyano, e.g., cyanoethyl, cyanopropyl, and the like.

"Halo" means fluoro, chloro, bromo, or iodo, preferably fluoro or chloro.

"$C_{1-6}$ haloalkyl" means $C_{1-6}$ alkyl radical as defined above, which is substituted with one or more halogen atoms, preferably one to five halogen atoms, preferably fluorine or chlorine, including those substituted with different halogens, e.g., —CH$_2$Cl, —CF$_3$, —CHF$_2$, —CH$_2$CF$_3$, —CF$_2$CF$_3$, —CF(CH$_3$)$_2$, and the like. When the $C_{1-6}$ alkyl is substituted with only fluoro, it can be referred to in this application as $C_{1-6}$ fluoroalkyl.

"$C_{1-6}$ haloalkoxy" means a —OR radical where R is $C_{1-6}$ haloalkyl as defined above e.g., —OCF$_3$, —OCHF$_2$, and the like. When R is haloalkyl where the $C_{1-6}$ alkyl is substituted with only fluoro, it can be referred to in this application as $C_{1-6}$ fluoroalkoxy.

"$C_{3-6}$ heterocycloalkyl" means a saturated or unsaturated monovalent monocyclic group of 4 to 8 ring atoms in which 1 or 2 ring atoms are heteroatom selected from N, O, or S(O)$_n$, where n is an integer from 0 to 2, the remaining ring atoms being C, unless stated otherwise. More specifically the term heterocyclyl includes, but is not limited to, pyrrolyl, piperidinyl, homopiperidinyl, morpholinyl, piperazinyl, tetrahydrofuranyl, tetrahydropyranyl, thiomorpholinyl, and the like. When the heterocyclyl ring is unsaturated it can contain one or two ring double bonds provided that the ring is not aromatic.

"$C_{1-5}$ heteroaryl" means a monovalent monocyclic aromatic radical of 5 or 6 ring atoms where one, two, or three, ring atoms are heteroatom selected from N, O, or S, the remaining ring atoms being carbon. Representative examples include, but are not limited to, pyrrolyl, thienyl, thiazolyl, imidazolyl, pyrazoly, furanyl, oxazolyl, isoxazolyl, pyridinyl, pyrimidinyl, pyrazinyl, pyridazinyl, triazolyl, and the like.

"$C_{3-6}$ oxoheterocycloalkyl" means a saturated or unsaturated monovalent monocyclic group of 4 to 8 ring atoms in which 1 or 2 ring atoms are heteroatom selected from N, O, or S(O)$_n$, where n is an integer from 0 to 2, and 1 or 2 rings atoms are —C(O)—, the remaining ring atoms being C, unless stated otherwise. More specifically the term heterocyclyl includes, but is not limited to, 2-oxo-1,2-dihydropyridinyl, and the like. When the heterocyclyl ring is unsaturated it can contain 1 or 2 ring double bonds provided that the ring is not aromatic.

The present invention also includes the prodrugs of compounds of Formula (IA) and (I). The term prodrug is intended to represent covalently bonded carriers, which are capable of releasing the active ingredient of Formula (IA) and (I) respectively, when the prodrug is administered to a mammalian subject. Release of the active ingredient occurs in vivo. Prodrugs can be prepared by techniques known to one skilled in the art. These techniques generally modify appropriate functional groups in a given compound. These modified functional groups however regenerate original functional groups in vivo or by routine manipulation. Prodrugs of compounds of Formula (IA) and (I) include compounds wherein a hydroxy, amino, carboxylic, or a similar group is modified. Examples of prodrugs include, but are not limited to esters (e.g., acetate, formate, and benzoate derivatives), carbamates (e.g., N,N-dimethylaminocarbonyl) of hydroxy or amino functional groups in compounds of Formula (IA) and (I)), amides (e.g., trifluoroacetylamino, acetylamino, and the like), and the like. Prodrugs of compounds of Formula (IA) and (I) are also within the scope of this invention.

The present invention also includes protected derivatives of compounds of Formula (IA) and (I). For example, when compounds of Formula (IA) and (I) contain groups such as hydroxy, carboxy, thiol or any group containing a nitrogen atom(s), these groups can be protected with a suitable protecting groups. A comprehensive list of suitable protective groups can be found in T. W. Greene, *Protective Groups in Organic Synthesis*, John Wiley & Sons, Inc. (1999), the disclosure of which is incorporated herein by reference in its entirety. The protected derivatives of compounds of Formula (IA) and (I) can be prepared by methods well known in the art.

A "pharmaceutically acceptable salt" of a compound means a salt that is pharmaceutically acceptable and that possesses the desired pharmacological activity of the parent compound. Such salts include: acid addition salts, formed with inorganic acids such as hydrochloric acid, hydrobromic acid, sulfuric acid, nitric acid, phosphoric acid, and the like; or formed with organic acids such as formic acid, acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like. It is understood that the pharmaceutically acceptable salts are non-toxic. Additional information on suitable pharmaceutically acceptable salts can be found in *Remington's Pharmaceutical Sciences*, 17th ed., Mack Publishing Company, Easton, Pa., 1985, which is incorporated herein by reference.

The compounds of the present invention may have asymmetric centers. Compounds of the present invention containing an asymmetrically substituted atom may be isolated in optically active or racemic forms. It is well known in the art how to prepare optically active forms, such as by resolution of materials. All chiral, diastereomeric, meso, racemic forms are within the scope of this invention, unless the specific stereochemistry or isomeric form is specifically indicated.

Additionally, as used herein the term $C_{1-6}$ alkyl and terms derived therefrom includes all the possible isomeric forms of said $C_{1-6}$ alkyl group. Furthermore, the cyclic groups such as aryl, heteroaryl, $C_{3-6}$ heterocycloalkyl include all the positional isomers. Furthermore, all polymorphic forms and hydrates of a compound of Formula (IA) and Formula (I) are within the scope of this invention.

The terms "compound" and "a compound of the invention" and "compound of the present invention" and the like, and their plural expressions include the embodiment of Formula (IA) and Formula (I) and the other more particular embodiments encompassed by Formula (IA) and Formula (I) described herein and exemplified compounds described herein and a pharmaceutically acceptable salt of each of these embodiments. All references to compounds, include all isotopes of the atoms contained therein, including isotopically-labeled compounds.

The compounds of the present invention exist as tautomers. All tautomeric forms the compounds of the invention are contemplated to be within the scope of the present invention.

"Optional" or "optionally" means that the subsequently described event or circumstance may but need not occur, and that the description includes instances where the event or circumstance occurs and instances in which it does not. For example, "$C_{3-6}$ heterocycloalkyl group optionally substituted with an $C_{1-6}$ alkyl group" means that the alkyl may but need not be present, and the description includes situations where the heterocycloalkyl group is substituted with an alkyl group and situations where the heterocycloalkyl group is not substituted with alkyl.

A "pharmaceutically acceptable carrier or excipient" means a carrier or an excipient that is useful in preparing a pharmaceutical composition that is generally safe, non-toxic and neither biologically nor otherwise undesirable, and includes a carrier or an excipient that is acceptable for veterinary use as well as human pharmaceutical use. "A pharmaceutically acceptable carrier/excipient" as used in the specification and claims includes both one and more than one such excipient. Pharmaceutically acceptable excipients are well known in the art, such as those in *Remington's Pharmaceutical Sciences*, 17th ed., Mack Publishing Company, Easton, Pa., 1985.

The terms "condition," "disorder," and "disease" relate to any unhealthy or abnormal state.

"Treat," "treating," or "treatment" of a disease includes:

(1) preventing the disease, i.e. causing the clinical symptoms of the disease not to develop in a mammal that may be exposed to or predisposed to the disease but does not yet experience or display symptoms of the disease;

(2) inhibiting the disease, i.e., arresting, controlling, slowing, stopping, or reducing the development of the disease or its clinical symptoms; or (3) relieving the disease, i.e., causing regression of the disease or its clinical symptoms or improvement of the disease or its clinical symptoms The terms "treat," "treating," and "treatment," do not necessarily indicate a total elimination of any or all symptoms or a cure of the disease.

As used herein the terms "patient" and "subject" includes humans and non-human animals, for example, mammals, such as mice, rats, guinea pigs, dogs, cats, rabbits, cows, horses, sheep, goats, and pigs. The term also includes birds, fish, reptiles, amphibians, and the like. It is understood that a more particular patient is a human. Also, more particular patients and subjects are non-human mammals, such as mice, rats, and dogs.

A "therapeutically effective amount" means the amount of a compound of Formula (I) or Formula (IA) or a pharmaceutically acceptable salt thereof that, when administered in single or multiple doses, to a mammal for treating a disease, is sufficient to effect such treatment for the disease. The "therapeutically effective amount" will vary depending on the compound, the disease and its severity and the age, weight, etc., of the mammal to be treated, the degree of or involvement or the severity of the condition, disorder, or disease, the response of the individual patient; the particular compound administered; the mode of administration; the bioavailability characteristics of the preparation administered; the dose regimen selected; the use of concomitant medication; and other relevant circumstances.

The term "disease treatable by administration of a 5HT3 receptor antagonist" includes emesis, migraine, substance abuse and addiction, neurodegenerative and psychiatric disorders such as anxiety and depression, eating disorders, schizophrenia, cognitive dysfunction associated with schizophrenia, Parkinson's disease, Huntington's Chorea, presenile dementias and Alzheimer's disease, and pain; GI disorders such as dyspepsia, gastroesophagal reflux disease, and irritable bowel syndrome; and immunological disorders and inflammation such as atherosclerosis, tendomyopathies and fibromyalgia. In a particular embodiment the disease is cognitive dysfunction associated with schizophrenia also known as cognitive impairment associated with schizophrenia.

Representative compounds of the Invention are shown in Table I below:

| Cpd. No. | | —Z—R$^1$ | Salt | Name | MW Calcd. | MS Obs. (M + 1)$^+$ |
|---|---|---|---|---|---|---|
| 1 | | | TFA | (1R,3R,5S)-8-methyl-8-azabicyclo[3.2.1]octan-3-yl 5-fluoro-1-(2,2,2-trifluoroethyl)-1H-indole-3-carboxylate; 2,2,2-trifluoroacetate | 384.3679 | 385.2 |

-continued

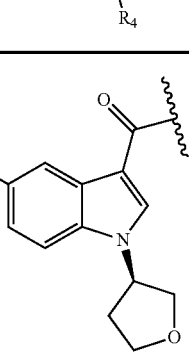

| Cpd. No. | | —Z—R¹ | Salt | Name | MW Calcd. | MS Obs. (M + 1)⁺ |
|---|---|---|---|---|---|---|
| 2 | 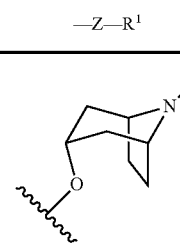 | 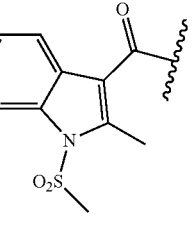 | TFA | (1R,3R,5S)-8-methyl-8-azabicyclo[3.2.1]octan-3-yl 5-fluoro-1-((R)-tetrahydrafuran-3-yl)-1H-indole-3-carboxylate; 2,2,2-trifluoroacetate | 372.4332 | 373.1 |
| 3 | 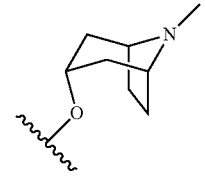 [SMILES: *OC1CC2CCC(C1)N2C] | 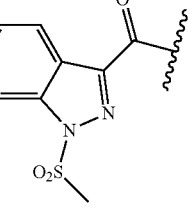 | TFA | (1R,3R,5S)-8-methyl-8-azabicyclo[3.2.1]octan-3-yl 2-methyl-1-(methylsulfonyl)-1H-indole-3-carboxylate; 2,2,2-trifluoroacetate | 376.4698 | 377.25 |
| 4 | 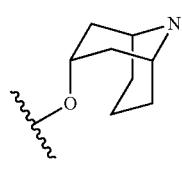 | 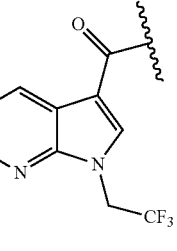 | TFA | (1R,3R,5S)-9-methyl-9-azabicyclo[3.3.1]nonan-3-yl 1-(methylsulfonyl)-1H-indazole-3-carboxylate, 2,2,2-trifluoroacetate | 377.4579 | 378.2 |
| 5 | 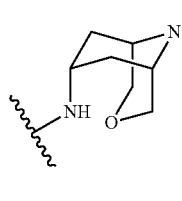 | 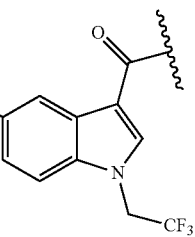 | TFA | N-((1R,5S,7S)-9-methyl-3-oxa-9-azabicyclo[3.3.1]nonan-7-yl)-1-(2,2,2-trifluoroethyl)-1H-pyrrolo[2,3-b]pyridine-3-carboxamide, 2,2,2-trifluoroacetate | 382.3802 | 383.3 |
| 6 | 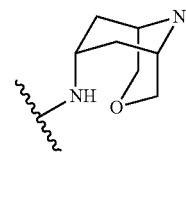 |  | TFA | N-((1R,5S,7S)-3-oxa-9-azabicyclo[3.3.1]nonan-7-yl)-5-fluoro-1-(2,2,2-trifluoroethyl)-1H-indole-3-carboxamide, 2,2,2-trifluoroacetate | 385.356 | 386.2 |

-continued

| Cpd. No. | (structure) | —Z—R¹ | Salt | Name | MW Calcd. | MS Obs. (M + 1)⁺ |
|---|---|---|---|---|---|---|
| 7 | | | TFA | 1-(2,2-difluoroethyl)-N-((1R,3R,5S)-9-methyl-9-azabicyclo[3.3.1]nonan-3-yl)-1H-indazole-3-carboxamide, 2,2,2-trifluoroacetate | 362.4169 | 363.3 |
| 8 | | | | N-((1R,5S,7S)-9-methyl-3-oxa-9-azabicyclo[3.3.1]nonan-7-yl)-1-(2,2,2-trifluoroethyl-1H-indole-3-carboxamide | 381.3921 | 382.2 |
| 9 | | | TFA | (1R,5S,7S)-3-oxa-9-azabicyclo[3.3.1]nonan-7-yl 1-(isopropylsulfonyl)-1H-indole-3-carboxylate, 2,2,2-trifluoroacetate | 392.4693 | 393.2 |
| 10 | | | TFA | 1-(isopropylsulfonyl)-N-((1R,5S,7S)-9-methyl-3-oxa-9-azabicyclo[3.3.1]nonan-7-yl)-1H-indole-3-carboxamide, 2,2,2-trifluoroacetate | 405.5111 | 406.2 |
| 12 | | | TFA | 1-(2-fluoroethyl)-N-((1R,3R,5S)-9-methyl-9-azabicyclo[3.3.1]-nonan-3-yl)-1H-indazole-3-carboxamide, 2,2,2-trifluoroacetate | 344.4264 | 345.3 |

-continued

| Cpd. No. | | —Z—R¹ | Salt | Name | MW Calcd. | MS Obs. (M + 1)⁺ |
|---|---|---|---|---|---|---|
| 13 | | | TFA | (1R,3R,5S)-8-methyl-8-azabicyclo[3.2.1]octan-3-yl 2-chloro-1-(methylsulfonyl)-1H-indole-3-carboxylate, 2,2,2-trifluoroacetate | 396.8883 | 397.2 |
| 14 | | | TFA | (1R,3R,5S)-8-azabicyclo[3.2.1]octan-3-yl 1-(2,2,2-trifluoroethyl)-1H-indole-3-carboxylate, 2,2,2-trifluoroacetate | 352.3509 | 353.2 |
| 15 | | | TFA | (1R,3R,5S)-8-methyl-8-azabicyclo[3.2.1]octan-3-yl 1-(2-fluoroethyl)-2-methyl-1H-indole-3-carboxylate, 2,2,2-trifluoroacetate | 344.4231 | 345.3 |
| 16 | | | TFA | (1R,3R,5S)-9-methyl-9-azabicyclo[3.3.1]nonan-3-yl 1-(2-fluoroethyl)-1H-indazole-3-carboxylate, 2,2,2-trifluoroacetate; 2,2,2-trifluoroacetate | 345.4112 | 346.2 |
| 17 | | | TFA | (1R,3R,5S)-8-methyl-8-azabicyclo[3.2.1]octan-3-yl 1-(2,2,2-trifluomethyl)-1H-indazole-3-carboxylate, 2,2,2-trifluoroacetate | 367.3655 | 368.2 |

-continued

| Cpd. No. | R4 structure | —Z—R¹ | Salt | Name | MW Calcd. | MS Obs. (M + 1)⁺ |
|---|---|---|---|---|---|---|
| 18 | 5-fluoro-1-(methylsulfonyl)-1H-indole-3-carbonyl | (1R,3R,5S)-8-methyl-8-azabicyclo[3.2.1]octan-3-yl-NH— | TFA | 5-fluoro-N-((1R,3R,5S)-8-methyl-8-azabicyclo[3.2.1]octan-3-yl)-1-(methylsulfonyl)-1H-indole-3-carboxamide, 2,2,2-trifluoroacetate | 379.449 | 380.2 |
| 19 | 5-fluoro-1-(methylsulfonyl)-1H-indole-3-carbonyl | (1R,5S,7S)-3-oxa-9-azabicyclo[3.3.1]nonan-7-yl—O— | TFA | (1R,5S,7S)-3-oxa-9-azabicyclo[3.3.1]nonan-7-yl 5-fluoro-1-(methylsulfonyl)-1H-indole-3-carboxylate, 2,2,2-trifluoroacetate | 382.4066 | 383.2 |
| 20 | 1-(2,2-difluoroethyl)-1H-indazole-3-carbonyl | (1R,5S,7S)-9-methyl-3-oxa-9-azabicyclo[3.3.1]nonan-7-yl-NH— | TFA | 1-(2,2-difluoroethyl)-N-((1R,5S,7S)-9-methyl-3-oxa-9-azabicyclo[3.3.1]nonan-7-yl)-1H-indazole-3-carboxamide, 2,2,2-trifluoroacetate | 364.3897 | 365.3 |
| 21 | 1-(2,2-difluoroethyl)-1H-indole-3-carbonyl | (1R,5S,7S)-9-methyl-3-oxa-9-azabicyclo[3.3.1]nonan-7-yl-NH— | TFA | 1-(2,2-difluoroethyl)-N-((1R,5S,7S)-9-methyl-3-oxa-9-azabicyclo[3.3.1]nonan-7-yl)-1H-indole-3-carboxamide, 2,2,2-trifluoroacetate | 363.4016 | 364.2 |
| 22 | 1-((S)-1,2,2,2-tetrafluoroethyl)-1H-pyrrolo[2,3-b]pyridine-3-carbonyl | (1R,5S,7S)-9-methyl-3-oxa-9-azabicyclo[3.3.1]nonan-7-yl-NH— |  | N-((1R,5S,7S)-9-methyl-3-oxa-9-azabicyclo[3.3.1]nonan-7-yl)-((S)-1,2,2,2-tetrafluoroethyl)-1H-pyrrolo[2,3-b]pyridine-3-carboxamide | 400.3706 | 401 |

-continued

| Cpd. No. | [structure] R4 | —Z—R¹ | Salt | Name | MW Calcd. | MS Obs. (M + 1)⁺ |
|---|---|---|---|---|---|---|
| 24 | 5-fluoro, N-CF3CH2 pyrrolo[2,3-b]pyridine ketone | bicyclic amine with CD3, NH, O | TFA | 5-fluoro-1-(2,2,2-trifluoroethyl)-N-((1R,5S,7S)-9-methyl-d₃-3-oxa-9-azabicyclo[3.3.1]nonan-7-yl)-1H-pyrrolo[2,3-b]pyridine-3-carboxamide, 2,2,2-trifluoroacetate | 403.3891 | 404.2 |
| 25 | 1-(pyrimidin-2-yl)indole-3-carbonyl | 3-oxa-9-azabicyclo[3.3.1]nonan-7-yl with NH | TFA | (1R,5S,7S)-3-oxa-9-azabicyclo[3.3.1]nonan-7-yl 1-(pyrimidin-2-yl)-1H-indole-3-carboxylate, 2,2,2-trifluoroacetate | 364.3978 | 365.2 |
| 26 | 1-(methylsulfonyl)indole-3-carbonyl | 8-methyl-8-azabicyclo[3.2.1]octan-3-yl ether | TFA | (1R,3R,5S)-8-methyl-8-azabicyclo[3.2.1]octan-3-yl 1-(methylsulfonyl)-1H-indole-3-carboxylate 2,2,2-trifluoroacetatea | 362.4433 | 363.2 |
| 27 | 5-fluoro-1-(2,2-difluoroethyl)indole-3-carbonyl | 8-methyl-8-azabicyclo[3.2.1]octan-3-yl ether | TFA | (1R,3R,5S)-8-methyl-8-azabicyclo[3.2.1]octan-3-yl 1-(2,2-difluoroethyl)-5-fluoro-1H-indole-3-carboxylate, 2,2,2-trifluoroacetate | 366.3774 | 367 |
| 28 | 2,3-dihydrooxazolo[3,2-a]indole-9-carbonyl | 8-methyl-8-azabicyclo[3.2.1]octan-3-yl ether | TFA | (1R,3R,5S)-8-methyl-8-azabicyclo[3.2.1]octan-3-yl 2,3-dihydrooxazolo[3,2-a]indole-9-carboxylate, 2,2,2-trifluoroacetate | 326.3896 | 327.25 |

-continued

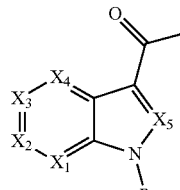

| Cpd. No. | [structure] | —Z—R¹ | Salt | Name | MW Calcd. | MS Obs. (M + 1)⁺ |
|---|---|---|---|---|---|---|
| 29 | | | TFA | (1R,3R,5S)-8-methyl-8-azabicyclo[3.2.1]octan-3-yl 5-fluoro-1-(tetrahydrofuran-3-yl)-1H-indole-3-carboxylate, 2,2,2-trifluoroacetate | 372.4332 | 373.25 |
| 30 | | | TFA | (1R,3R,5S)-9-methyl-9-azabicyclo[3.1.1]nonan-3-yl 2-chloro-1-(2-fluoroethyl)-1H-indole-3-carboxylate, 2,2,2-trifluoroacetate | 378.8682 | 379.2 |
| 31 | | | TFA | (1R,5S,7S)-3-oxa-9-azabicyclo[3.3.1]nonan-7-yl 1-(2,2-difluoroethyl)-5-fluoro-1H-indole-3-carboxylate, 2,2,2-trifluoroacetate | 368.3503 | 369.2 |
| 32 | | | TFA | (1R,5S,7S)-9-methyl-3-oxa-9-azabicyclo[3.3.1]nonan-7-yl 5-fluoro-1-(2,2,2-trifluoroethyl)-1H-indole-3-carboxylate, 2,2,2-trifluoroacetate | 400.3673 | 401.15 |
| 33 | | | TFA | (1R,5S,7S)-9-(2-fluoroethyl)-3-oxa-9-azabicyclo[3.3.1]nonan-7-yl 1-(2,2-difluoroethyl)-5-fluoro-1H-indole-3-carboxylate, 2,2,2-trifluoroacetate | 414.3939 | 415.2 |

-continued

| Cpd. No. | R4 | —Z—R¹ | Salt | Name | MW Calcd. | MS Obs. (M + 1)+ |
|---|---|---|---|---|---|---|
| 34 | | | TFA | (1R,3R,5S)-9-methyl-9-azabicyclo[3.3.1]nonan-7-yl 5-fluoro-1-(methylsulfonyl)-1H-indole-3-carboxylate, 2,2,2-trifluoroacetate | 394.4603 | 395.2 |
| 35 | | | TFA | 5-fluoro-N-((1R,5S,7S)-9-methyl-3-oxa-9-azabicyclo[3.3.1]nonan-7-yl)-1-(2,2,2-trifluoroethyl)-1H-indole-3-carboxylate, 2,2,2-trifluoroacetate | 399.3825 | 400.25 |
| 36 | | | TFA | 5-fluoro-N-((1R,5S,7S)-9-methyl-3-oxa-9-azabicyclo[3.3.1]nonan-7-yl)-1-(methylsulfonyl)-1H-indole-3-carboxylate, 2,2,2-trifluoroacetate | 395.4484 | 396.2 |
| 37 | | | TFA | quinuclidin-4-yl 5-fluoro-1-(methylsulfonyl)-1H-indole-3-carboxylate, 2,2,2-trifluoroacetate | 366.4072 | 367.2 |
| 38 | | | TFA | N-((1R,5S,7S)-3-oxa-9-azabicyclo[3.3.1]nonan-7-yl)-1-(2,2,2-trifluoroethyl)-1H-pyrrolo[2,3-b]pyridine-3-carboxamide, 2,2,2-trifluoroacetate | 368.3536 | 369.2 |

-continued

| Cpd. No. | R4 | —Z—R1 | Salt | Name | MW Calcd. | MS Obs. (M + 1)+ |
|---|---|---|---|---|---|---|
| 39 | | | TFA | N-((1R,5S,7S)-3-oxa-9-azabicyclo[3.3.1]nonan-7-yl)-1-(2,2-difluoroethyl)-5-fluoro-1H-pyrrolo[2,3-b]pyridine-3-carboxamide, 2,2,2-trifluoroacetate | 368.3536 | 369.2 |
| 40 | | | TFA | (1R,3R,5S)-8-methyl-8-azabicyclo[3.2.1]octan-3-yl 1-(2,2-difluoroethyl)-1H-indole-3-carboxylate, 2,2,2-trifluoroacetate | 348.387 | 349.3 |
| 41 | | | TFA | (1R,3R,5S)-8-methyl-8-azabicyclo[3.2.1]octan-3-yl 1-(2,2,2-trifluoroethyl)-1H-pyrrolo[2,3-b]pyridine-3-carboxylate, 2,2,2-trifluoroacetate | 367.3655 | 368.3 |
| 42 | | | TFA | (1R,3R,5S)-8-methyl-8-azabicyclo[3.2.1]octan-3-yl 1-(tetrahydrofuran-3-yl)-1H-indole-3-carboxylate, 2,2,2-trifluoroacetate | 354.4427 | 355.3 |
| 43 | | | TFA | (1R,3R,5S)-8-methyl-8-azabicyclo[3.2.1]octan-3-yl 2-chloro-1-(2,2-difluoroethyl)-1H-indole-3-carboxylate, 2,2,2-trifluoroacetate | 382.832 | 383.2 |

-continued

| Cpd. No. | (structure) | —Z—R¹ | Salt | Name | MW Calcd. | MS Obs. (M + 1)⁺ |
|---|---|---|---|---|---|---|
| 44 | | | TFA | (1R,3R,5S)-8-methyl-8-azabicyclo[3.2.1]octan-3-yl 2-chloro-1-(2,2,2-trifluoroethyl)-1H-indole-3-carboxylate, 2,2,2-trifluoroacetate | 400.8225 | 401.2 |
| 45 | | | TFA | (1R,3R,5S)-8-azabicyclo[3.2.1]octan-3-yl 1-(2,2-difluoroethyl)-1H-indole-3-carboxylate, 2,2,2-trifluoroacetate | 334.3604 | 335.25 |
| 46 | | | TFA | N-((1R,3R,5S)-9-methyl-9-azabicyclo[3.3.1]nonan-3-yl)-1-(methylsulfonyl)-1H-indazole-3-carboxamide, 2,2,2-trifluoroacetate | 376.4732 | 377.3 |
| 47 | | | TFA | (1R,5S,7S)-9-methyl-3-oxa-9-azabicyclo[3.3.1]nonan-7-yl 1-(methylsulfonyl)-1H-indole-3-carboxylate, 2,2,2-trifluoroacetate | 378.4427 | 379.15 |
| 48 | | | | (1R,5S,7S)-9-methyl-3-oxa-9-azabicyclo[3.3.1]nonan-7-yl 1-(2,2-difluoroethyl)-1H-pyrrolo[2,3-b]pyridine-3-carboxylate | 365.3745 | 366.2 |

-continued

| Cpd. No. | R4 | —Z—R¹ | Salt | Name | MW Calcd. | MS Obs. (M + 1)⁺ |
|---|---|---|---|---|---|---|
| 49 | 7-azaindole with N-CH₂CF₃, 3-C(O)- | 9-methyl-3-oxa-9-azabicyclo[3.3.1]nonan-7-yl-O- | TFA | (1R,5S,7S)-9-methyl-3-oxa-9-azabicyclo[3.3.1]nonan-7-yl 1-(2,2,2-trifluoroethyl)-1H-pyrrolo[2,3-b]pyridine-3-carboxylate, 2,2,2-trifluoroacetate | 383.3649 | 384.2 |
| 50 | 5-fluoroindole with N-CH₂CF₃, 3-C(O)- | 9-(2-fluoroethyl)-3-oxa-9-azabicyclo[3.3.1]nonan-7-yl-O- | TFA | (1R,5S,7S)-9-(2-fluoroethyl)-3-oxa-9-azabicyclo[3.3.1]nonan-7-yl 5-fluoro-1-(2,2,2-trifluoroethyl)-1H-indole-3-carboxylate, 2,2,2-trifluoroacetate | 432.3844 | 433.25 |
| 51 | 7-azaindole with N-CH₂CH₂F, 3-C(O)- | 9-methyl-3-oxa-9-azabicyclo[3.3.1]nonan-7-yl-O- | TFA | (1R,5S,7S)-9-methyl-3-oxa-9-azabicyclo[3.3.1]nonan-7-yl 1-(2-fluoroethyl)-1H-indole-3-carboxylate, 2,2,2-trifluoroacetate | 346.3959 | 347.3 |
| 52 | 5-fluoro-7-azaindole with N-CH₂CF₃, 3-C(O)- | 9-methyl-3-oxa-9-azabicyclo[3.3.1]nonan-7-yl-NH- | TFA | 5-fluoro-N-((1R,5S,7S)-9-methyl-3-oxa-9-azabicyclo[3.3.1]-nonan-7-yl)-1-(2,2,2-trifluoroethyl)-1H-pyrrolo[2,3-b]pyridine-3-carboxamide, 2,2,2-trifluoroacetate | 400.3706 | 401.2 |
| 53 | 5-fluoro-7-azaindole with N-CHFCHF₂ (1,1,2,2-tetrafluoroethyl), 3-C(O)- | 9-methyl-3-oxa-9-azabicyclo[3.3.1]nonan-7-yl-NH- | TFA | 5-fluoro-N-((1R,5S,7S)-9-methyl-3-oxa-9-azabicyclo[3.3.1]-nonan-7-yl)-1-(1,1,2,2-tetrafluoroethyl)-1H-pyrrolo[2,3-b]pyridine-3-carboxamide, 2,2,2-trifluoroacetate | 418.3611 | 419.15 |

| Cpd. No. | R4 structure | —Z—R¹ | Salt | Name | MW Calcd. | MS Obs. (M + 1)+ |
|---|---|---|---|---|---|---|
| 54 | 5-fluoro-1-(isopropylsulfonyl)-1H-indol-3-yl ketone | 3-oxa-9-azabicyclo[3.3.1]nonan-7-yl-oxy (NH) | TFA | (1R,5S,7S)-3-oxa-9-azabicyclo[3.3.1]nonan-7-yl 5-fluoro-1-(isopropylsulfonyl)-1H-indole-3-carboxylate, 2,2,2-trifluoroacetate | 410.4597 | 411.15 |
| 55 | 2-chloro-1-(2-fluoroethyl)-1H-indol-3-yl ketone | 8-methyl-8-azabicyclo[3.2.1]octan-3-yl-oxy | TFA | (1R,3R,5S)-8-methyl-8-azabicyclo[3.2.1]octan-3-yl 2-chloro-1-(2-fluoroethyl)-1H-indole-3-carboxylate, 2,2,2-trifluoroacetate | 364.8416 | 365.2 |
| 56 | 1-(2-fluoroethyl)-1H-indol-3-yl ketone | 8-methyl-8-azabicyclo[3.2.1]octan-3-yl-oxy | TFA | (1R,3R,5S)-8-methyl-8-azabicyclo[3.2.1]octan-3-yl 1-(2-fluoroethyl)-1H-indole-3-carboxylate, 2,2,2-trifluoroacetate | 330.3965 | 331.2 |
| 57 | 1-(2-fluoroethyl)-1H-indazol-3-yl ketone | 8-methyl-8-azabicyclo[3.2.1]octan-3-yl-oxy | TFA | (1R,3R,5S)-8-methyl-8-azabicyclo[3.2.1]octan-3-yl 1-(2-fluoroethyl)-1H-indazole-3-carboxylate, 2,2,2-trifluoroacetate | 331.3846 | 332.3 |
| 58 | 1-(2,2-difluoroethyl)-5-fluoro-1H-indol-3-yl ketone | 9-methyl-3-oxa-9-azabicyclo[3.3.1]nonan-7-yl-oxy | TFA | (1R,5S,7S)-9-methyl-3-oxa-9-azabicyclo[3.3.1]nonan-7-yl 1-(2,2-difluoroethyl)-5-fluoro-1H-indole-3-carboxylate, 2,2,2-trifluoroacetate | 382.3769 | 383.2 |

-continued

| Cpd. No. | R4 | —Z—R¹ | Salt | Name | MW Calcd. | MS Obs. (M + 1)⁺ |
|---|---|---|---|---|---|---|
| 59 | 5-fluoro-1-(2,2,2-trifluoroethyl)indol-3-yl ketone | 3-oxa-9-azabicyclo[3.3.1]nonan-7-yloxy (NH) | TFA | (1R,5S,7S)-3-oxa-9-azabicyclo[3.3.1]nonan-7-yl 5-fluoro-1-(2,2,2-trifluoroethyl)-1H-indole-3-carboxylate, 2,2,2-trifluoroacetate | 386.3407 | 387.2 |
| 60 | 5-fluoro-1-(2,2-difluoroethyl)indol-3-yl ketone | 9-methyl-9-azabicyclo[3.3.1]nonan-3-yloxy | TFA | (1R,3R,5S)-9-methyl-9-azabicyclo[3.3.1]nonan-3-yl 1-(2,2-difluoroethyl)-5-fluoro-1H-indole-3-carboxylate, 2,2,2-trifluoroacetate | 380.404 | 381.2 |
| 61 | 1-(2,2-difluoroethyl)pyrrolo[2,3-b]pyridin-3-yl ketone | 9-methyl-9-azabicyclo[3.3.1]nonan-3-yloxy | TFA | (1R,3R,5S)-9-methyl-9-azabicyclo[3.3.1]nonan-3-yl 1-(2,2-difluoroethyl)-1H-pyrrolo[2,3-b]pyridine-3-carboxylate, 2,2,2-trifluoroacetate | 363.4016 | 364.3 |
| 62 | 1-(methylsulfonyl)indazol-3-yl ketone | 8-methyl-8-azabicyclo[3.2.1]octan-3-ylamino | TFA | N-((1R,3R,5S)-8-methyl-8-azabicyclo[3.2.1]octan-3-yl)-1-(methylsulfonyl)-1H-indazole-3-carboxamide, 2,2,2-trifluoroacetate | 362.4466 | 363.2 |
| 63 | 5-fluoro-1-(2,2-difluoroethyl)indol-3-yl ketone | 9-methyl-3-oxa-9-azabicyclo[3.3.1]nonan-7-ylamino | TFA | 1-(2,2-difluoroethyl)-5-fluoro-N-((1R,5S,7S)-9-methyl-3-oxa-9-azabicyclo[3.3.1]nonan-7-yl)-1H-indole-3-carboxamide, 2,2,2-trifluoroacetate | 381.3921 | 382.25 |

-continued

| Cpd. No. | [core structure] | —Z—R¹ | Salt | Name | MW Calcd. | MS Obs. (M+1)⁺ |
|---|---|---|---|---|---|---|
| 64 | | | TFA | 1-(2,2-difluoroethyl)-N-((1R,5S,7S)-9-methyl-3-oxa-9-azabicyclo[3.3.1]nonan-7-yl)-1H-pyrrolo[2,3-b]pyridine-3-carboxamide, 2,2,2-trifluoroacetate | 364.3897 | 365.3 |
| 65 | | | TFA | N-((1R,5S,7S)-3-oxa-9-azabicyclo[3.3.1]nonan-7-yl)-1-(2,2-difluoroethyl)-1H-indazole-3-carboxamide, 2,2,2-trifluoroacetate | 350.3631 | 351.2 |
| 66 | | | TFA | 1-(2,2-difluoroethyl)-N-((1R,5S,7S)-9-methyl-3-oxa-9-azabicyclo[3.3.1]nonan-7-yl)-1H-pyrazolo[3,4-b]pyridine-3-carboxamide, 2,2,2-trifluoroacetate | 365.3777 | 366.25 |
| 67 | | | TFA | (R)-1-(2,2-difluoroethyl)-N-(quinuclidin-3-yl)-1H-pyrrolo[2,3-b]pyridine-3-carboxamide, 2,2,2-trifluoroacetate | 334.3637 | 335.25 |
| 68 | | | TFA | 1-(2,2-difluoroethyl)-5-fluoro-N-((1R,5S,7S)-9-methyl-3-oxa-9-azabicyclo[3.3.1]nonan-7-yl)-1H-pyrrolo[2,3-b]pyridine-3-carboxamide, 2,2,2-trifluoroacetate | 382.3802 | 383.25 |

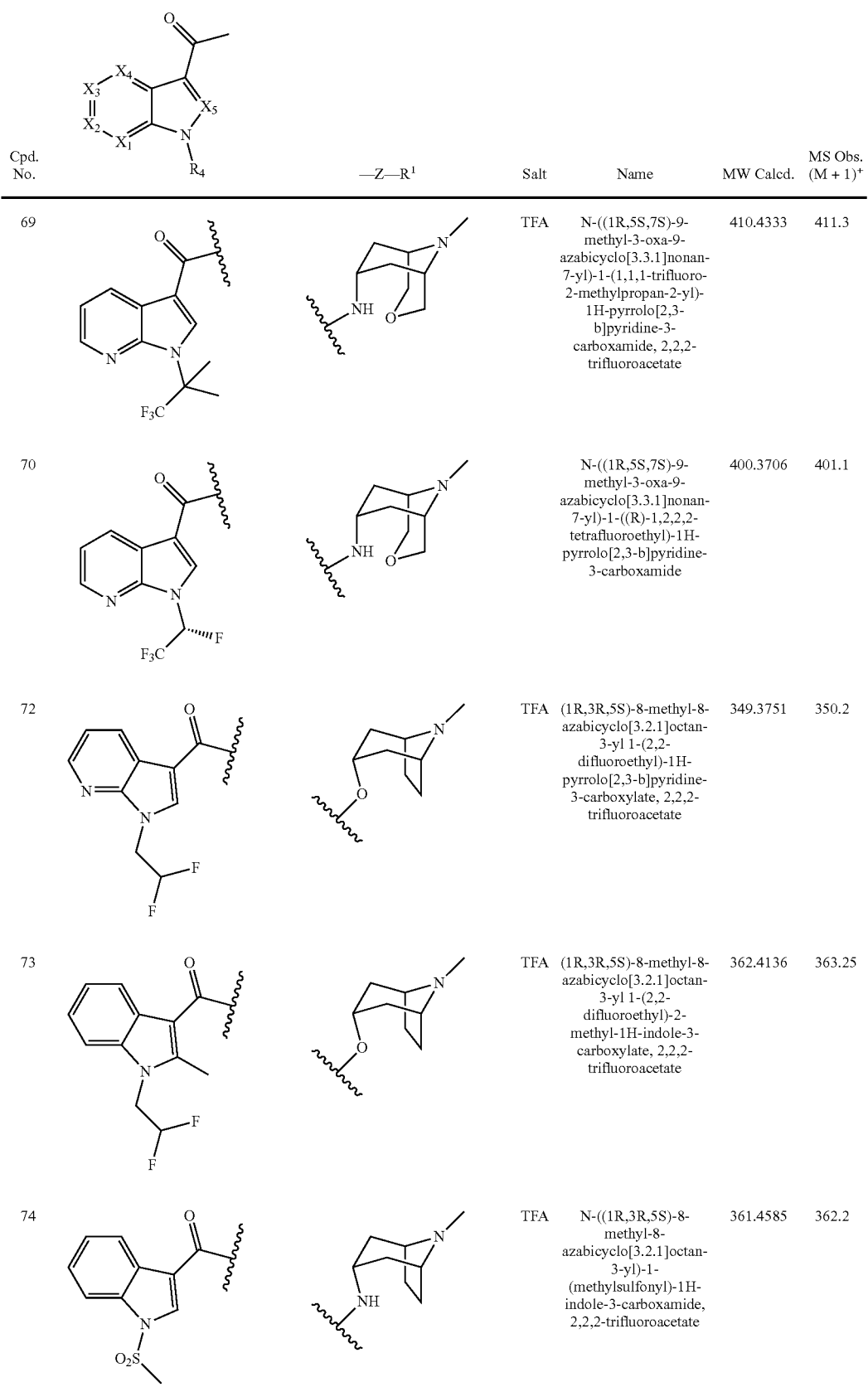

| Cpd. No. | | —Z—R¹ | Salt | Name | MW Calcd. | MS Obs. (M + 1)⁺ |
|---|---|---|---|---|---|---|
| 69 | | | TFA | N-((1R,5S,7S)-9-methyl-3-oxa-9-azabicyclo[3.3.1]nonan-7-yl)-1-(1,1,1-trifluoro-2-methylpropan-2-yl)-1H-pyrrolo[2,3-b]pyridine-3-carboxamide, 2,2,2-trifluoroacetate | 410.4333 | 411.3 |
| 70 | | | | N-((1R,5S,7S)-9-methyl-3-oxa-9-azabicyclo[3.3.1]nonan-7-yl)-1-((R)-1,2,2,2-tetrafluoroethyl)-1H-pyrrolo[2,3-b]pyridine-3-carboxamide | 400.3706 | 401.1 |
| 72 | | | TFA | (1R,3R,5S)-8-methyl-8-azabicyclo[3.2.1]octan-3-yl 1-(2,2-difluoroethyl)-1H-pyrrolo[2,3-b]pyridine-3-carboxylate, 2,2,2-trifluoroacetate | 349.3751 | 350.2 |
| 73 | | | TFA | (1R,3R,5S)-8-methyl-8-azabicyclo[3.2.1]octan-3-yl 1-(2,2-difluoroethyl)-2-methyl-1H-indole-3-carboxylate, 2,2,2-trifluoroacetate | 362.4136 | 363.25 |
| 74 | | | TFA | N-((1R,3R,5S)-8-methyl-8-azabicyclo[3.2.1]octan-3-yl)-1-(methylsulfonyl)-1H-indole-3-carboxamide, 2,2,2-trifluoroacetate | 361.4585 | 362.2 |

-continued

| Cpd. No. | R4 structure | —Z—R¹ | Salt | Name | MW Calcd. | MS Obs. (M + 1)⁺ |
|---|---|---|---|---|---|---|
| 75 | 5-fluoro-indole with 2,2-difluoroethyl on N, 3-acyl | 8-methyl-8-azabicyclo[3.2.1]octan-3-yl-NH | TFA | 1-(2,2-difluoroethyl)-5-fluoro-N-((1R,3R,5S)-8-methyl-8-azabicyclo[3.2.1]octan-3-yl)-1H-indole-3-carboxamide, 2,2,2-trifluoroacetate | 365.3927 | 366.2 |
| 76 | pyrrolo[2,3-b]pyridine with 2,2-difluoroethyl on N, 3-acyl | 8-methyl-8-azabicyclo[3.2.1]octan-3-yl-NH | TFA | 1-(2,2-difluoroethyl)-N-((1R,3R,5S)-8-methyl-8-azabicyclo[3.2.1]octan-3-yl)-1H-pyrrolo[2,3-b]pyridine-3-carboxamide, 2,2,2-trifluoroacetate | 348.3903 | 349.25 |
| 77 | pyrrolo[2,3-b]pyridine with 2,2-difluoroethyl on N, 3-acyl | 9-methyl-9-azabicyclo[3.3.1]nonan-3-yl-NH | TFA | 1-(2,2-difluoroethyl)-N-((1R,3R,5S)-9-methyl-9-azabicyclo[3.3.1]nonan-3-yl)-1H-pyrrolo[2,3-b]pyridine-3-carboxamide, 2,2,2-trifluoroacetate | 362.4169 | 363.3 |
| 78 | 5-fluoro-indole with methylsulfonyl on N, 3-acyl | 3-oxa-9-azabicyclo[3.3.1]nonan-7-yl-NH | TFA | N-((1R,5S,7S)-3-oxa-9-azabicyclo[3.3.1]nonan-7-yl)-5-fluoro-1-(methylsulfonyl)-1H-indole-3-carboxamide, 2,2,2-trifluoroacetate | 381.4218 | 382.2 |
| 79 | indole with 2-fluoroethyl on N, 3-acyl | 9-methyl-3-oxa-9-azabicyclo[3.3.1]nonan-7-yl-NH | TFA | 1-(2-fluoroethyl)-N-((1R,5S,7S)-9-methyl-3-oxa-9-azabicyclo-[3.3.1]nonan-7-yl)-1H-indole-3-carboxamide, 2,2,2-trifluoroacetate | 345.4112 | 346.3 |

-continued

| Cpd. No. | (structure) | —Z—R¹ | Salt | Name | MW Calcd. | MS Obs. (M + 1)⁺ |
|---|---|---|---|---|---|---|
| 80 | | | TFA | N-((1R,5S,7S)-9-methyl-3-oxa-9-azabicyclo[3.3.1]nonan-7-yl)-1-(1,1,2,2-tetrafluoroethyl)-1H-pyrrolo[2,3-b]pyridine-3-carboxamide, 2,2,2-trifluoroacetate | 400.3706 | 401.2 |
| 81 | | | TFA | N-((1R,5S,7S)-9-methyl-3-oxa-9-azabicyclo[3.3.1]nonan-7-yl)-1-(1,2,2,2-tetrafluoroethyl)-1H-pyrrolo[2,3-b]pyridine-3-carboxamide, 2,2,2-trifluoroacetate | 400.3706 | 401.2 |
| 82 | | | TFA | N-((1R,5S,7S)-3-oxa-9-azabicyclo[3.3.1]nonan-7-yl)-1-(2,2-difluoroethyl)-1H-pyrrolo[2,3-b]pyridine-3-carboxamide, 2,2,2-trifluoroacetate | 350.3631 | 351.2 |
| 83 | | | TFA | (1R,3R,5S)-8-methyl-8-azabicyclo[3.2.1]octan-3-yl 1-((R)-tetrahydrofuran-3-yl)-1H-indole-3-carboxylate, 2,2,2-trifluoroacetate | 354.4427 | 354.9 |
| 84 | | | TFA | (1R,3R,5S)-8-methyl-8-azabicyclo[3.2.1]octan-3-yl 2,3,4,5-tetrahydro-[1,3]oxazepino[3,2-a]indole-11-carboxylate, 2,2,2-trifluoroacetate | 354.4427 | 355.25 |

-continued

| Cpd. No. | [structure] | —Z—R¹ | Salt | Name | MW Calcd. | MS Obs. (M + 1)⁺ |
|---|---|---|---|---|---|---|
| 85 | | | TFA | (1R,3R,5S)-8-methyl-8-azabicyclo[3.2.1]octan-3-yl 3,4-dihydro-2H-[1,3]oxazino[3,2-a]indole-10-carboxylate, 2,2,2-trifluoroacetate | 340.4162 | 341.3 |
| 86 | | | TFA | (1R,3R,5S)-8-methyl-8-azabicyclo[3.2.1]octan-3-yl 5-fluoro-1-(methylsulfonyl)-1H-indole-3-carboxylate, 2,2,2-trifluoroacetate | 380.4337 | 381.2 |
| 87 | | | TFA | (1R,3R,5S)-9-methyl-9-azabicyclo[3.3.1]nonan-3-yl 1-(2-fluoroethyl)-1H-indole-3-carboxylate, 2,2,2-trifluoroacetate | 344.4231 | 345.3 |
| 88 | | | TFA | (1R,3R,5S)-9-methyl-9-azabicyclo[3.3.1]nonan-3-yl 1-(2-fluoroethyl)-2-methyl-1H-indole-3-carboxylate, 2,2,2-trifluoroacetate | 358.4497 | 359.3 |
| 89 | | | TFA | (1R,3R,5S)-9-methyl-9-azabicyclo[3.3.1]nonan-3-yl 5-fluoro-1-(2,2,2-trifluoroethyl)-1H-indole-3-carboxylate, 2,2,2-trifluoroacetate | 398.3945 | 399.2 |

-continued

| Cpd. No. | [structure] | —Z—R¹ | Salt | Name | MW Calcd. | MS Obs. (M + 1)⁺ |
|---|---|---|---|---|---|---|
| 90 | | | TFA | 1-(2,2-difluoroethyl)-N-((1R,3R,5S)-8-methyl-8-azabicyclo-[3.2.1]octan-3-yl)-1H-indazole-3-carboxamide, 2,2,2-trifluoroacetate | 348.3903 | 349.25 |
| 91 | | | TFA | (1S,5R,6S)-4-oxa-1-azabicyclo[3.3.1]nonan-6-yl 1-(2,2-difluoroethyl)-5-fluoro-1H-indole-3-carboxylate, 2,2,2-trifluoroacetate | 368.3503 | 369.25 |
| 93 | | | TFA | 5-fluoro-1-(isopropylsulfonyl)-N-((1R,5S,7S)-9-methyl-3-oxa-9-azabicyclo[3.3.1]nonan-7-yl)-1H-indole-3-carboxamide, 2,2,2-trifluoroacetate | 423.5016 | 424.2 |
| 95 | | | TFA | (1R,3R,5S)-8-methyl-8-azabicyclo[3.2.1]octan-3-yl 1-(2,2,2-trifluoroethyl)-1H-indole-3-carboxylate, 2,2,2-trifluoroacetate | 366.3774 | 367.2 |
| 96 | | | TFA | (1R,3R,5S)-8-methyl-8-azabicyclo[3.2.1]octan-3-yl 1-((S)-tetrahydrofuran-3-yl)-1H-indole-3-carboxylate, 2,2,2-trifluoroacetate | 354.4427 | 354.9 |

| Cpd. No. | [structure] | —Z—R¹ | Salt | Name | MW Calcd. | MS Obs. (M + 1)⁺ |
|---|---|---|---|---|---|---|
| 97 | | | | (1R,3R,5S)-8-methyl-8-azabicyclo[3.2.1]octan-3-yl 5-fluoro-1-((S)-tetrahydrofuran-3-yl)-1H-indole-3-carboxylate | 372.4332 | 373.1 |
| 98 | | | TFA | 1-(2,2-difluoroethyl)-5-fluoro-N-((1R,3R,5S)-9-methyl-9-azabicyclo[3.3.1]nonan-3-yl)-1H-indole-3-carboxamide, 2,2,2-trifluoroacetate | 379.4193 | 380.2 |
| 99 | | | TFA | (1R,5S,7S)-9-methyl-3-oxa-9-azabicyclo[3.3.1]nonan-7-yl 5-fluoro-1-(methylsulfonyl)-1H-indole-3-carboxylate, 2,2,2-trifluoroacetate | 396.4331 | 397.15 |
| 100 | | | TFA | 5-fluoro-N-((1R,3R,5S)-9-methyl-9-azabicyclo[3.3.1]nonan-3-yl)-1-(methylsulfonyl)-1H-indole-3-carboxamide, 2,2,2-trifluoroacetate | 393.4756 | 394.2 |
| 101 | | | TFA | (1R,5S,7S)-3-oxa-9-azabicyclo[3.3.1]nonan-7-yl 1-(2,2-difluoroethyl)-1H-pyrrolo[2,3-b]pyridine-3-carboxylate, 2,2,2-trifluoroacetate | 351.3479 | 352.2 |

-continued

| Cpd. No. | —Z—R¹ | Salt | Name | MW Calcd. | MS Obs. (M + 1)⁺ |
|---|---|---|---|---|---|
| 102 | | TFA | N-((1R,3R,5S)-8-methyl-8-azabicyclo[3.2.1]octan-3-yl)-1-(2,2,2-trifluoroethyl)-1H-pyrrolo[2,3-b]pyridine-3-carboxamide, 2,2,2-trifluoroacetate | 366.3807 | 367.2 |
| 103 | | TFA | (1R,3R,5S)-9-methyl-9-azabicyclo[3.3.1]nonan-3-yl 1-(2,2,2-trifluoroethyl)-1H-pyrrolo[2,3-b]pyridine-3-carboxylate, 2,2,2-trifluoroacetate | 381.3921 | 382.2 |
| 104 | | TFA | 1-(2,2-difluoroethyl)-N-((1R,5S,7S)-9-(trifluoromethyl)-3-oxa-9-azabicyclo[3.3.1]nonan-7-yl)-1H-pyrrolo[2,3-b]pyridine-3-carboxamide, 2,2,2-trifluoroacetate | 418.3611 | 419.2 |
| 105 | | TFA | N-((1R,5S,7S)-3-oxa-9-azabicyclo[3.3.1]nonan-7-yl)-5-fluoro-1-(2,2,2-trifluoroethyl)-1H-pyrrolo[2,3-b]pyridine-3-carboxamide, 2,2,2-trifluoroacetate | 386.344 | 387.2 |
| 107 | | TFA | N-((1R,5S,7S)-9-methyl-3-oxa-9-azabicyclo[3.3.1]nonan-7-yl)-1-(pyrimidin-2-yl)-1H-indole-3-carboxamide, 2,2,2-trifluoroacetate | 377.4396 | 378.2 |

-continued

| Cpd. No. | (core structure) | —Z—R¹ | Salt | Name | MW Calcd. | MS Obs. (M+1)⁺ |
|---|---|---|---|---|---|---|
| 108 | 1-(2,2-difluoropropyl)-7-azaindole-3-acyl | (1R,5S,7S)-9-methyl-3-oxa-9-azabicyclo[3.3.1]nonan-7-ylamino | TFA | 1-(2,2-difluoropropyl)-N-((1R,5S,7S)-9-methyl-3-oxa-9-azabicyclo[3.3.1]nonan-7-yl)-1H-pyrrolo[2,3-b]pyridine-3-carboxamide, 2,2,2-trifluoroacetate | 378.4163 | 379.2 |
| 109 | 5-fluoro-1-(2,2-difluoroethyl)-7-azaindole-3-acyl | (1R,5S,7S)-9-methyl-d₃-3-oxa-9-azabicyclo[3.3.1]nonan-7-ylamino |  | 1(2,2-difluoroethyl)-5-fluoro-N-((1R,5S,7S)-9-methyl-d₃-3-oxa-9-azabicyclo[3.3.1]nonan-7-yl)-1H-pyrrolo[2,3-b]pyridine-3-carboxamide | 385.3986 | 386.3 |
| 110 | 1-(methylsulfonyl)-indole-3-acyl | (1R,5S,7S)-9-methyl-d₃-3-oxa-9-azabicyclo[3.3.1]nonan-7-ylamino | TFA | N-((1R,5S,7S)-9-methyl-d₃-3-oxa-9-azabicyclo[3.3.1]nonan-7-yl)-1-(methylsulfonyl)-1H-indole-3-carboxamide, 2,2,2-trifluoroacetate | 380.48 | 381.25 |
| 111 | 1-(isopropylsulfonyl)-indole-3-acyl | (1R,5S,7S)-9-methyl-d₃-3-oxa-9-azabicyclo[3.3.1]nonan-7-ylamino | TFA | N-((1R,5S,7S)-9-methyl-d₃-3-oxa-9-azabicyclo[3.3.1]nonan-7-yl)-1-(isopropylsulfonyl)-1H-indole-3-carboxamide, 2,2,2-trifluoroacetate | 408.53 | 409.3 |
| 112 | 1-(2,2,2-trifluoroethyl)-indole-3-acyl | (1R,5S,7S)-9-methyl-d₃-3-oxa-9-azabicyclo[3.3.1]nonan-7-ylamino | TFA | 1-(2,2,2-trifluoroethyl)-5-fluoro-N-((1R,5S,7S)-9-methyl-d₃-3-oxa-9-azabicyclo[3.3.1]nonan-7-yl)-1H-indole-3-carboxamide, 2,2,2-trifluoroacetate | 384.41 | 385.2 |

-continued

| Cpd. No. | (structure with X1-X5, R4) | —Z—R¹ | Salt | Name | MW Calcd. | MS Obs. (M + 1)+ |
|---|---|---|---|---|---|---|
| 113 | | | TFA | 1-(2,2-difluoroethyl)-5-fluoro-N-((1R,5S,7S)-9-methyl-d₃-3-oxa-9-azabicyclo[3.3.1]nonan-7-yl)-1H-indole-3-carboxamide, 2,2,2-trifluoroacetate | 366.42 | 367.3 |
| 116 | | | TFA | (S)-1-(2,2-difluoroethyl)-N-(quinuclidin-3-yl)-1H-pyrrolo[2,3-b]pyridine-3-carboxamide, 2,2,2-trifluoroacetate | 334.36 | 335.20 |
| 117 | | | TFA | N-((1R,5S,7S)-9-methyl-3-oxa-9-azabicyclo[3.3.1]nonan-7-yl)-1-(pyridazin-3-yl)-1H-indole-3-carboxamide, 2,2,2-trifluoroacetate | 377.44 | 378.25 |
| 118 | | | TFA | N-((1R,5S,7S)-9-methyl-3-oxa-9-azabicyclo[3.3.1]nonan-7-yl)-1-(thiazol-2-yl)-1H-indole-3-carboxamide, 2,2,2-trifluoroacetate | 382.48 | 383.2 |
| 119 | | | TFA | N-((1R,5S,7S)-9-methyl-3-oxa-9-azabicyclo[3.3.1]nonan-7-yl)-1-(thiazol-5-yl)-1H-indole-3-carboxamide, 2,2,2-trifluoroacetate | 382.48 | 383.2 |

-continued

| Cpd. No. | Structure | —Z—R¹ | Salt | Name | MW Calcd. | MS Obs. (M + 1)⁺ |
|---|---|---|---|---|---|---|
| 120 | indole-pyrimidin-5-yl ketone | 9-methyl-3-oxa-9-azabicyclo[3.3.1]nonan-7-yl NH | TFA | N-((1R,5S,7S)-9-methyl-3-oxa-9-azabicyclo[3.3.1]nonan-7-yl)-1-(pyrimidin-5-yl)-1H-indole-3-carboxamide, 2,2,2-trifluoroacetate | 377.44 | 378.25 |
| 122 | indole-pyrimidin-2-yl ketone | 9-methyl-d₃-3-oxa-9-azabicyclo[3.3.1]nonan-7-yl NH | TFA | N-((1R,5S,7S)-9-methyl-d₃-3-oxa-9-azabicyclo[3.3.1]nonan-7-yl)-1-(pyrimidin-2-yl)-1H-indole-3-carboxamide, 2,2,2-trifluoroacetate | 380.46 | 381.25 |
| 123 | indole-pyridazin-3-yl ketone | 9-methyl-d₃-3-oxa-9-azabicyclo[3.3.1]nonan-7-yl NH | TFA | N-((1R,5S,7S)-9-methyl-d₃-3-oxa-9-azabicyclo[3.3.1]nonan-7-yl)-1-(pyridazin-3-yl)-1H-indole-3-carboxamide, 2,2,2-trifluoroacetate | 380.46 | 381.3 |
| 126 | indazole-CH₂CF₃ ketone | 9-methyl-d₃-3-oxa-9-azabicyclo[3.3.1]nonan-7-yl NH | TFA | N-((1R,5S,7S)-9-methyl-d₃-3-oxa-9-azabicyclo[3.3.1]nonan-7-yl)-1-(2,2,2-trifluoroethyl)-1H-indazole-3-carboxamide, 2,2,2-trifluoroacetate | 385.4 | 386.25 |
| 127 | indole-CH₂CH₂F ketone | 9-methyl-d₃-3-oxa-9-azabicyclo[3.3.1]nonan-7-yl NH | TFA | 1-(2-fluoroethyl)-N-((1R,5S,7S)-9-methyl-d₃-3-oxa-9-azabicyclo[3.3.1]nonan-7-yl)-1H-indole-3-carboxamide, 2,2,2-trifluoroacetate | 348.43 | 349.3 |

-continued

| Cpd. No. | R4 structure | —Z—R¹ | Salt | Name | MW Calcd. | MS Obs. (M + 1)+ |
|---|---|---|---|---|---|---|
| 128 | 1-(thiazol-2-yl)-indol-3-yl ketone | 3-oxa-9-azabicyclo[3.3.1]nonan-7-yl-O- (NH) | TFA | (1R,5S,7S)-3-oxa-9-azabicyclo[3.3.1]nonan-7-yl 1-(thiazol-2-yl)-1H-indole-3-carboxamide, 2,2,2-trifluoroacetate | 369.44 | 370.2 |
| 129 | 1-(pyrazin-2-yl)-indol-3-yl ketone | 9-methyl-3-oxa-9-azabicyclo[3.3.1]nonan-7-yl-NH | TFA | N-((1R,5S,7S)-9-methyl-3-oxa-9-azabicyclo[3.3.1]nonan-7-yl)-1-(pyrazin-2-yl)-1H-indole-3-carboxamide, di-2,2,2-trifluoroacetate | 377.44 | 378.3 |
| 130 | 1-(pyrazin-2-yl)-indol-3-yl ketone | 9-CD₃-3-oxa-9-azabicyclo[3.3.1]nonan-7-yl-NH | | N-((1R,5S,7S)-9-methyl-d₃-3-oxa-9-azabicyclo[3.3.1]nonan-7-yl)-1-(pyrazin-2-yl)-1H-indole-3-carboxamide | 380.46 | 381.3 |
| 131 | 1-(isopropylsulfonyl)-indol-3-yl ketone | 3-oxa-9-azabicyclo[3.3.1]nonan-7-yl-O- (NH) | TFA | (1R,5S,7S)-3-oxa-9-azabicyclo[3.3.1]nonan-7-yl 1-(isopropylsulfonyl)-1H-indole-3-carboxylate, 2,2,2-trifluoroacetate | 392.4693 | 393.2 |
| 132 | 1-(methylsulfonyl)-indol-3-yl ketone | 3-oxa-9-azabicyclo[3.3.1]nonan-7-yl-O- (NH) | TFA | (1R,5S,7S)-3-oxa-9-azabicyclo[3.3.1]nonan-7-yl 5-fluoro-1-(methylsulfonyl)-1H-indole-3-carboxylate, 2,2,2-trifluoroacetate | 364.42 | 365.2 |

| Cpd. No. | R4 structure | —Z—R¹ | Salt | Name | MW Calcd. | MS Obs. (M + 1)⁺ |
|---|---|---|---|---|---|---|
| 133 | 1-(ethylsulfonyl)-1H-indol-3-yl acetyl | 3-oxa-9-azabicyclo[3.3.1]nonan-7-yl (NH) | TFA | (1R,5S,7S)-3-oxa-9-azabicyclo[3.3.1]nonan-7-yl 1-(ethylsulfonyl)-1H-indole-3-carboxylate, 2,2,2-trifluoroacetate | 378.44 | 379.2 |
| 134 | 1-(cyclopropylsulfonyl)-1H-indol-3-yl acetyl | 3-oxa-9-azabicyclo[3.3.1]nonan-7-yl (NH) | TFA | (1R,5S,7S)-3-oxa-9-azabicyclo[3.3.1]nonan-7-yl 1-(cyclopropylsulfonyl)-1H-indole-3-carboxylate, 2,2,2-trifluoroacetate | 390.45 | 391.2 |
| 135 | 1-(isobutylsulfonyl)-1H-indol-3-yl acetyl | 3-oxa-9-azabicyclo[3.3.1]nonan-7-yl (NH) | TFA | (1R,5S,7S)-3-oxa-9-azabicyclo[3.3.1]nonan-7-yl 1-(isobutylsulfonyl)-1H-indole-3-carboxylate, 2,2,2-trifluoroacetate | 406.5 | 407.2 |
| 136 | 1-(pyridazin-3-yl)-1H-indol-3-yl acetyl | 3-oxa-9-azabicyclo[3.3.1]nonan-7-yl (NH) | TFA | (1R,5S,7s)-3-oxa-9-azabicyclo[3.3.1]nonan-7-yl 1-(pyridazin-3-yl)-1H-indole-3-carboxylate, 2,2,2-trifluoroacetic acid salt | 364.398 | 365.20 |
| 137 | 1-(6-fluoropyridazin-3-yl)-1H-indol-3-yl acetyl | 9-methyl-3-oxa-9-azabicyclo[3.3.1]nonan-7-yl | TFA | (1R,5S,7s)-9-methyl-3-oxa-9-azabicyclo[3.3.1]nonan-7-yl 1-(6-fluoropyridazin-3-yl)-1H-indole-3-carboxylate | 396.415 | 397.20 |

-continued

| Cpd. No. | R4 structure | —Z—R¹ | Salt | Name | MW Calcd. | MS Obs. (M + 1)+ |
|---|---|---|---|---|---|---|
| 141 | indole with N-pyrazin-2-yl, 3-acetyl | 3-oxa-9-azabicyclo[3.3.1]nonan-7-yl-O- (NH) | TFA | (1R,5S,7s)-3-oxa-9-azabicyclo[3.3.1]nonan-7-yl 1-(pyrazin-2-yl)-1H-indole-3-carboxylate, 2,2,2-trifluoroacetic acid salt | 364.398 | 365.20 |
| 142 | 7-fluoropyrrolo[2,3-c]pyridine with N-CH2CN, 3-acetyl | 9-methyl-3-oxa-9-azabicyclo[3.3.1]nonan-7-yl-O- | TFA | (1R,5S,7s)-9-methyl-3-oxa-9-azabicyclo[3.3.1]nonan-7-yl 1-(cyanomethyl)-7-fluoro-1H-pyrrolo[2,3-c]pyridine-3-carboxylate, 2,2,2-trifluoroacetic acid salt | 358.367 | 359.15 |
| 143 | indole with N-isothiazol-4-yl, 3-acetyl | 3-oxa-9-azabicyclo[3.3.1]nonan-7-yl-O- (NH) | TFA | (1R,5S,7s)-3-oxa-9-azabicyclo[3.3.1]nonan-7-yl 1-(isothiazol-4-yl)-1H-indole-3-carboxylate, 2,2,2-trifluoroacetic acid salt | 369.437 | 370.15 |
| 144 | indole with N-isothiazol-4-yl, 3-acetyl | 9-methyl-3-oxa-9-azabicyclo[3.3.1]nonan-7-yl-NH- | TFA | 1-(isothiazol-4-yl)-N-((1R,5S,7s)-9-methyl-3-oxa-9-azabicyclo[3.3.1]nonan-7-yl)-1H-indole-3-carboxamide, 2,2,2-trifluoroacetic acid salt | 382.479 | 383.20 |
| 145 | indole with N-isothiazol-3-yl, 3-acetyl | 3-oxa-9-azabicyclo[3.3.1]nonan-7-yl-O- (NH) | TFA | (1R,5S,7s)-3-oxa-9-azabicyclo[3.3.1]nonan-7-yl 1-(isothiazol-3-yl)-1H-indole-3-carboxamide, 2,2,2-trifluoroacetic acid salt | 369.437 | 370.20 |

-continued

| Cpd. No. | [structure] | —Z—R¹ | Salt | Name | MW Calcd. | MS Obs. (M + 1)⁺ |
|---|---|---|---|---|---|---|
| 146 | | | TFA | N-((1R,5S,7s)-9-methyl-3-oxa-9-azabicyclo[3.3.1]nonan-7-yl)-1-(thiazol-2-yl)-1H-pyrrolo[2,3-b]pyridine-3-carboxamide, 2,2,2-trifluoroacetic acid salt | 383.467 | 384.20 |
| 147 | | | TFA | N-((1R,5S,7s)-9-methyl-3-oxa-9-azabicyclo[3.3.1]nonan-7-yl)-1-(thiazol-4-yl)-1H-pyrrolo[2,3-b]pyridine-3-carboxamide, 2,2,2-trifluoroacetic acid salt | 383.467 | 384.25 |
| 148 | | | TFA | N-((1R,5S,7s)-9-methyl-3-oxa-9-azabicyclo[3.3.1]nonan-7-yl)-1-(thiazol-5-yl)-1H-pyrrolo[2,3-b]pyridine-3-carboxamide, 2,2,2-trifluoroacetic acid salt | 383.467 | 384.20 |
| 153 | | | TFA | 1-(isothiazol-3-yl)-N-((1R,5S,7s)-9-methyl-3-oxa-9-azabicyclo[3.3.1]nonan-7-yl)-1H-indole-3-carboxamide, 2,2,2-trifluoroacetic acid salt | 382.479 | 383.20 |
| 154 | | | TFA | 1-(1-methyl-1H-imidazol-5-yl)-N-((1R,5S,7s)-9-methyl-3-oxa-9-azabicyclo[3.3.1]nonan-7-yl)-1H-indole-3-carboxamide | 379.456 | 380.20 |

-continued

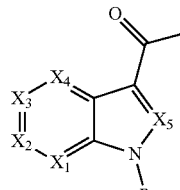

| Cpd. No. | R4 | —Z—R¹ | Salt | Name | MW Calcd. | MS Obs. (M + 1)⁺ |
|---|---|---|---|---|---|---|
| 155 | 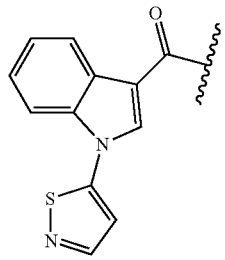 [SMILES: *C(=O)c1cn(-c2ccns2)c2ccccc12] |  | TFA | (1R,5S,7s)-3-oxa-9-azabicyclo[3.3.1]nonan-7-yl 1-(isothiazol-5-yl)-1H-indole-3-carboxamide, 2,2,2-trifluoroacetic acid salt | 369.497 | 370.10 |
| 158 | 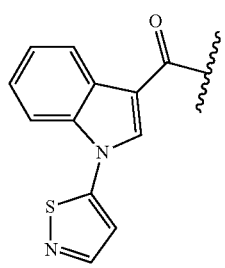 [SMILES: *C(=O)c1cn(-c2ccns2)c2ccccc12] |  | TFA | 1-(isothiazol-5-yl)-N-((1R,5S,7s)-9-methyl-3-oxa-9-azabicyclo[3.3.1]nonan-7-yl)-1H-indole-3-carboxamide, 2,2,2-trifluoroacetic acid salt | 382.479 | 383.20 |
| 159 | 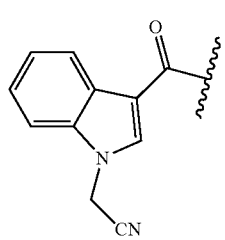 [SMILES: *C(=O)c1cn(CC#N)c2ccccc12] |  | TFA | 1-(cyanomethyl)-N-((1R,5S,7s)-9-methyl-3-oxa-9-azabicyclo[3.3.1]nonan-7-yl)-1H-indole-3-carboxamide, 2,2,2-trifluoroacetic acid salt | 338.404 | 339.20 |
| 160 | 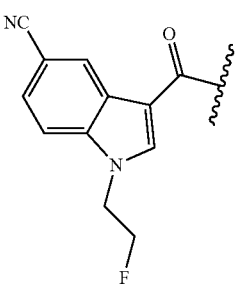 [SMILES: *C(=O)c1cn(CCF)c2ccc(C#N)cc12] |  | TFA | (1R,5S,7s)-9-methyl-3-oxa-9-azabicyclo[3.3.1]nonan-7-yl 5-cyano-1-(2-fluoroethyl)-1H-indole-3-carboxylate, 2,2,2-trifluoroacetic acid salt | 371.405 | 372.30 |
| 161 | 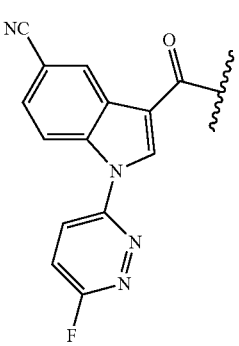 [SMILES: *C(=O)c1cn(-c2ccc(F)nn2)c2ccc(C#N)cc12] |  | TFA | 1R,5S,7s)-9-methyl-3-oxa-9-azabicyclo[3.3.1]nonan-7-yl 5-cyano-1-(6-fluoropyridazin-3-yl)-1H-indole-3-carboxylate | 421.424 | 423.25 |

| Cpd. No. | Structure | —Z—R¹ | Salt | Name | MW Calcd. | MS Obs. (M+1)⁺ |
|---|---|---|---|---|---|---|
| 162 | 5-fluoro-7-azaindole with N-thiazol-2-yl | oxa-azabicyclic NH | TFA | 5-fluoro-N-((1R,5S,7s)-9-methyl-3-oxa-9-azabicyclo[3.3.1]nonan-7-yl)-1-(thiazol-2-yl)-1H-pyrrolo[2,3-b]pyridine-3-carboxamide, 2,2,2-trifluoroacetic acid salt | 401.458 | 402.20 |
| 163 | 5-fluoro-7-azaindole with N-thiazol-4-yl | oxa-azabicyclic NH | TFA | 5-fluoro-N-((1R,5S,7s)-9-methyl-3-oxa-9-azabicyclo[3.3.1]nonan-7-yl)-1-(thiazol-4-yl)-1H-pyrrolo[2,3-b]pyridine-3-carboxamide, 2,2,2-trifluoroacetic acid salt | 401.458 | 402.15 |
| 164 | 5-fluoro-7-azaindole with N-thiazol-5-yl | oxa-azabicyclic NH | TFA | 5-fluoro-N-((1R,5S,7s)-9-methyl-3-oxa-9-azabicyclo[3.3.1]nonan-7-yl)-1-(thiazol-5-yl)-1H-pyrrolo[2,3-b]pyridine-3-carboxamide, 2,2,2-trifluoroacetic acid salt | 401.458 | 402.20 |
| 165 | indazole with N-thiazol-5-yl | oxa-azabicyclic NH | TFA | N-((1R,5S,7s)-9-methyl-3-oxa-9-azabicyclo[3.3.1]nonan-7-yl)-1-(thiazol-5-yl)-1H-indazole-3-carboxamide, 2,2,2-trifluoroacetic acid salt | 383.467 | 384.20 |
| 168 | indole with N-(1-methyl-2-oxo-1,2-dihydropyridin-4-yl) | oxa-azabicyclic O-linked | TFA | 1R,5S,7s)-3-oxa-9-azabicyclo[3.3.1]nonan-7-yl 1-(1-methyl-2-oxo-1,2-dihydropyridin-4-yl)-1H-indole-3-carboxylate, 2,2,2-trifluoroacetic acid salt | 393.436 | 374.25 |

-continued

| Cpd. No. | [structure] | —Z—R¹ | Salt | Name | MW Calcd. | MS Obs. (M + 1)⁺ |
|---|---|---|---|---|---|---|
| 169 | | | TFA | (1R,5S,7s)-9-methyl-3-oxa-9-azabicyclo[3.3.1]nonan-7-yl 1-(6-hydroxypyridazin-3-yl)-1H-indole-3-carboxylate, 2,2,2-trifluoroacetic acid salt | 394.424 | 395.20 |
| 171 | | | TFA | (1R,5S,7s)-3-oxa-9-azabicyclo[3.3.1]nonan-7-yl 1-(2-cyanophenyl)-1H-indole-3-carboxylate, 2,2,2-trifluoroacetic acid salt | 387.431 | 388.20 |
| 172 | | | TFA | (1R,5S,7s)-3-oxa-9-azabicyclo[3.3.1]nonan-7-yl 1-(3-cyanophenyl)-1H-indole-3-carboxylate, 2,2,2-trifluoroacetic acid salt | 387.431 | 388.20 |
| 174 | | | TFA | N-((1R,5S,7s)-9-methyl-3-oxa-9-azabicyclo[3.3.1]nonan-7-yl)-1-phenyl-1H-indole-3-carboxamide, 2,2,2-trifluoroacetic acid salt | 375.464 | 376.25 |

-continued

| Cpd. No. | [structure] | —Z—R¹ | Salt | Name | MW Calcd. | MS Obs. (M + 1)⁺ |
|---|---|---|---|---|---|---|
| 177 | | | TFA | (1R,5S,7s)-3-oxa-9-azabicyclo[3.3.1]nonan-7-yl 1-(oxazol-2-yl)-1H-indole-3-carboxylate, 2,2,2-trifluoroacetic acid salt | 353.372 | 354.20 |
| 178 | | | TFA | N-((1R,5S,7s)-9-methyl-3-oxa-9-azabicyclo[3.3.1]nonan-7-yl)-1-(oxazol-2-yl)-indole-3-carboxamide, 2,2,2-trifluoroacetic acid salt | 366.414 | 367.30 |
| 180 | | | TFA | (1R,5S,7s)-3-oxa-9-azabicyclo[3.3.1]nonan-7-yl 1-(4-cyanophenyl)-1H-indole-3-carboxylate, 2,2,2-trifluoroacetic acid salt | 387.431 | 388.20 |
| 181 | | | TFA | (1R,5S,7S)-9-methyl-3-oxa-9-azabicyclo[3.3.1]nonan-7-yl 1-(pyrazin-3-yl)-1H-indole-3-carboxylate | 378.42 | 379.30 |
| 182 | | | TFA | (1R,5S,7S)-9-methyl-3-oxa-9-azabicyclo[3.3.1]nonan-7-yl 1-(isothiazol-3-yl)-1H-indole-3-carboxylate | 383.46 | 384.3 |

-continued

| Cpd. No. | [core structure] | —Z—R¹ | Salt | Name | MW Calcd. | MS Obs. (M + 1)⁺ |
|---|---|---|---|---|---|---|
| 183 | 1-(thiazol-5-yl)-1H-indol-3-yl ketone | 9-methyl-3-oxa-9-azabicyclo[3.3.1]nonan-7-yl oxy | TFA | (1R,5S,7S)-9-methyl-3-oxa-9-azabicyclo[3.3.1]nonan-7-yl 1-(thiazol-5-yl)-1H-indole-3-carboxylate | 383.46 | 384.25 |
| 184 | 1-(5-fluoropyrazin-2-yl)-1H-indol-3-yl ketone | 9-methyl-3-oxa-9-azabicyclo[3.3.1]nonan-7-yl oxy | TFA | (1R,5S,7S)-9-methyl-3-oxa-9-azabicyclo[3.3.1]nonan-7-yl 1-(5-fluoropyrazin-2-yl)-1H-indole-3-carboxylate | 396.42 | 397.20 |
| 185 | 1-(isothiazol-4-yl)-1H-indol-3-yl ketone | N-methyl-3-oxa-9-azabicyclo[3.3.1]nonan-7-amine | TFA | N-((1R,5S,7S)-3-oxa-9-azabicyclo[3.3.1]nonan-7-yl)-1-(isothiazol-4-yl)-N-methyl-1H-indole-3-carboxamide | 382.48 | 383.30 |
| 186 | 1-(isothiazol-4-yl)-1H-indol-3-yl ketone | N,9-dimethyl-3-oxa-9-azabicyclo[3.3.1]nonan-7-amine | TFA | 1-(isothiazol-4-yl)-N-methyl-N-((1R,5S,7S)-9-methyl-3-oxa-9-azabicyclo[3.3.1]nonan-7-yl)-1H-indole-3-carboxamide | 396.51 | 397.30 |
| 187 | 1-(cyanomethyl)-1H-indol-3-yl ketone | 3-oxa-9-azabicyclo[3.3.1]nonan-7-yl oxy | TFA | (1R,5S,7S)-3-oxa-9-azabicyclo[3.3.1]nonan-7-yl 1-(cyanomethyl)-1H-indole-3-carboxylate | 325.36 | 326.20 |

| Cpd. No. | R₄ | —Z—R¹ | Salt | Name | MW Calcd. | MS Obs. (M+1)⁺ |
|---|---|---|---|---|---|---|
| 188 | indole N-substituted with pyrimidin-2-yl | 9-methyl-3-oxa-9-azabicyclo[3.3.1]nonan-7-yl, O-linked | TFA | (1R,5S,7S)-9-methyl-3-oxa-9-azabicyclo[3.3.1]nonan-7-yl 1-(pyrimidin-2-yl)-1H-indole-3-carboxylate | 378.42 | 379.30 |
| 189 | indole N-substituted with pyrimidin-5-yl | 9-methyl-3-oxa-9-azabicyclo[3.3.1]nonan-7-yl, O-linked | TFA | (1R,5S,7S)-9-methyl-3-oxa-9-azabicyclo[3.3.1]nonan-7-yl 1-(pyrimidin-5-yl)-1H-indole-3-carboxylate | 378.42 | 379.30 |
| 190 | indole N-substituted with pyridazin-4-yl | 9-methyl-3-oxa-9-azabicyclo[3.3.1]nonan-7-yl, NH-linked | TFA | N-((1R,5S,7S)-9-methyl-3-oxa-9-azabicyclo[3.3.1]nonan-7-yl)-1-(pyridazin-4-yl)-1H-indole-3-carboxamide | 377.44 | 378.40 |

Embodiments
Compounds of Formula (I)
Embodiment (A)

In one embodiment, the compound of Formula (I) or a pharmaceutically acceptable salt thereof, as defined in the Summary is where $R_4$ is heteroaryl selected from the group consisting of furanyl, pyrrolyl, imidazolyl, oxazolyl, isoxazolyl, oxadiazolyl, thiazolyl, isothiazolyl, thiadiazolyl, triazolyl, tetrazolyl, pyrazinyl, pyridazinyl, pyrimidyl, azepinyl, diazepinyl, quinolyl, isoquinolyl, quinolizidine, benzofuranyl, benzothienyl, indolyl, isoindolyl, indazolyl, benzimidazolyl, benzisothiazolyl, benzisoxazolyl, benzoxadiazolyl, benzoxazolyl, benzothiazolyl, benzothiadiazolyl, benzotriazolyl, benzopyrazinyl, benzopyrazidinyl, benzoazepinyl, benzodiazepinyl, imidazopyridyl, pyrazolopyridyl, pyrrolopyridyl, quinazolyl, purinyl, furopyridyl, and thienopyridyl; each optionally substituted with one or two substituents independently selected from $C_{1-6}$ alkyl, $C_{1-6}$ haloalkyl, $C_{1-6}$ haloalkoxy, $C_{1-6}$ alkoxy, hydroxy, cyano, or halo.

Embodiment (B)

In another embodiment, the compound of Formula (I) or a pharmaceutically acceptable salt thereof as defined in the Summary is where $R_4$ is heteroaryl selected from the group consisting of furanyl, pyrrolyl, imidazolyl, oxazolyl, isoxazolyl, oxadiazolyl, thiazolyl, isothiazolyl, thiadiazolyl, triazolyl, tetrazolyl, pyrazinyl, pyridazinyl, and pyrimidyl; each optionally substituted with one or two substituents independently selected from $C_{1-6}$ alkyl, $C_{1-6}$ haloalkyl, $C_{1-6}$ haloalkoxy, $C_{1-6}$ alkoxy, hydroxy, cyano, or halo.

Embodiment (C)

In another embodiment, the compound of Formula (I) or a pharmaceutically acceptable salt thereof as defined in the Summary is where $R_4$ is heteroaryl selected from the group consisting of quinolyl, isoquinolyl, quinolizidine, benzofuranyl, benzothienyl, indolyl, isoindolyl, indazolyl, benzimidazolyl, benzisothiazolyl, benzisoxazolyl, benzoxadiazolyl, benzoxazolyl, benzothiazolyl, benzothiadiazolyl, benzotriazolyl, benzopyrazinyl, benzopyrazidinyl, benzoazepinyl, benzodiazepinyl, imidazopyridyl, pyrazolopyridyl, pyrrolopyridyl, quinazolyl, purinyl, furopyridyl, and thienopyridyl; each optionally substituted with one or two substituents independently selected from $C_{1-6}$ alkyl, $C_{1-6}$ haloalkyl, $C_{1-6}$ haloalkoxy, $C_{1-6}$ alkoxy, hydroxy, cyano, or halo.

Embodiment (D)

In another embodiment, the compound of Formula (I) or a pharmaceutically acceptable salt thereof as defined in the Summary is where $R_4$ is pyrimidinyl, pyridazinyl, isothiazolyl, thiazolyl, oxazolyl, isoxazolyl, or furanyl; each optionally substituted with one or two substituents independently selected from $C_{1-6}$ alkyl, $C_{1-6}$ haloalkyl, $C_{1-6}$ haloalkoxy, $C_{1-6}$ alkoxy, or halo.

Within this embodiment, in another group of compounds, $R_4$ is heteroaryl oxazolyl optionally substituted with one or two substituents independently selected from $C_{1-6}$ alkyl, $C_{1-6}$ haloalkyl, $C_{1-6}$ haloalkoxy, $C_{1-6}$ alkoxy, hydroxy, cyano, or halo.

Within this embodiment, in another group of compounds $R_4$ is pyrimidinyl optionally substituted with one or two substituents independently selected from $C_{1-6}$ alkyl, $C_{1-6}$ haloalkyl, $C_{1-6}$ haloalkoxy, cyano, $C_{1-6}$ alkoxy, or halo.

Within this embodiment, in another group of compounds $R_4$ is pyridazinyl optionally substituted with one or two substituent(s), preferably one substituent, independently selected from methyl, ethyl, isopropyl, difluoromethyl, 2-fluoroethyl, trifluoromethyl, cyano, or fluoro.

Within this embodiment, in another group of compounds $R_4$ thiazolyl optionally substituted with one or two substituents independently selected from $C_{1-6}$ alkyl, $C_{1-6}$ haloalkyl, $C_{1-6}$ haloalkoxy, cyano, $C_{1-6}$ alkoxy, or halo.

Within this embodiment, in another group of compounds $R_4$ is pyrimidin-2-yl, pyridazin-3-yl, 6-fluoropyridazin-3-yl, pyrazin-2-yl, thiazol-2-yl, thiazol-5-yl, isothiazol-3-yl, isothiazol-4-yl, 1-methyl-1H-imidazol-5-yl, oxazol-2-yl, or pyrimidin-5-yl.

Embodiment (E)

In one embodiment, the compound of Formula (I) or a pharmaceutically acceptable salt thereof as defined in the Summary and embodiments (A), (B), (C), and (D) above and embodiments contained therein, is where Z is O.

Embodiment (F)

In one embodiment, the compound of Formula (I) or a pharmaceutically acceptable salt thereof as defined in the Summary and embodiments (A), (B), (C), and (D) above and embodiments contained therein, is where Z is $NR_a$. Within this embodiment, in another group of compounds $R_a$ is hydrogen. Within this embodiment, in another group of compounds $R_a$ is methyl.

Embodiment (G)

In one embodiment within embodiment G, the compound of Formula (I) or a pharmaceutically acceptable salt thereof as defined in the Summary and embodiments (A), (B), (C), (D), (E), and (F) above and embodiments contained therein, is where $R_1$ is a ring of formula (a)
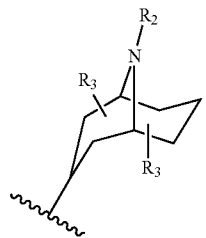

(d)
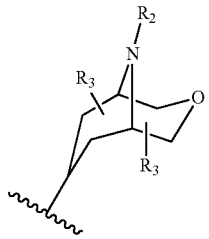

(e)
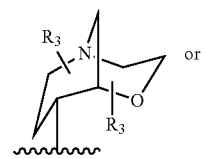

(f)
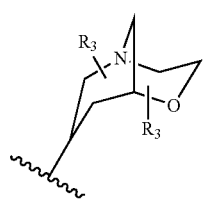

or (g)
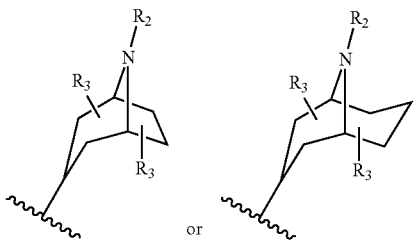

(a) Within groups in embodiment (G), in one group of compounds $R_1$ is a ring of formula (a) or (d). Within (a), in one embodiment, $R_1$ is a ring of formula

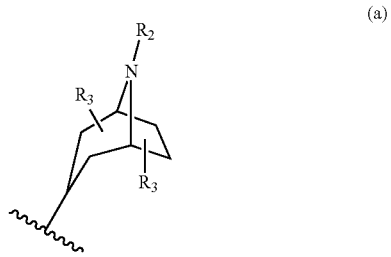

or (b) Within groups in embodiment (G), in another group of compounds $R_1$ is a ring of formula (e), (f) or (g). Within (b), in one group of compounds $R_1$ is a ring of formula (e). Within (b), in one group of compounds $R_1$ is a ring of formula (f) or (g). Within (b), in one group of compounds $R_1$ is a ring of formula

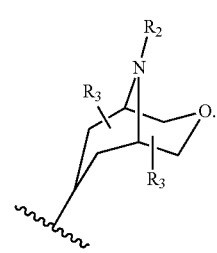

(i) Within groups in embodiment (G) and embodiments contained therein i.e., (a) and (b) and groups contained therein, in one group of compounds each $R_3$ is independently hydrogen or methyl. Within these groups of compounds in one group of compounds each $R_3$ is hydrogen.

(ii) Within groups in embodiment (G) and embodiments contained therein i.e., (a) and (b) and groups contained therein, in one group of compounds each $R_3$ is independently hydrogen or methyl and $R_2$ is hydrogen. Within these groups of compounds in one group of compounds $R_2$ is hydrogen and each $R_3$ is hydrogen.

(iii) Within groups in embodiment (G) and embodiments contained therein i.e., (a) and (b) and groups contained therein, in one group of compounds each $R_3$ is independently hydrogen or methyl and $R_2$ is $C_{1-6}$ alkyl. Within these groups of compounds in one group of compounds $R_2$ is methyl, ethyl, or propyl and each $R_3$ is hydrogen. Within these groups of compounds in one group of compounds $R_2$ is methyl and each $R_3$ is hydrogen.

(iv) Within groups in embodiment (G) and embodiments contained therein i.e., (a) and (b) and groups contained therein, in one group of compounds each $R_3$ is independently hydrogen or methyl and $R_2$ is $C_{1-6}$ haloalkyl. Within these groups of compounds in one group of compounds each $R_2$ is trifluoromethyl, 2-fluoroethyl, or 2,2,2-trifluoroethyl and each $R_3$ is hydrogen. Within these groups of compounds in one group of compounds $R_2$ is trifluoromethyl and each $R_3$ is hydrogen.

(v) Within groups in embodiment (G) and embodiments contained therein i.e., (a) and (b) and groups contained therein, in one group of compounds each $R_3$ is independently hydrogen or methyl.

Embodiment (H)

In another embodiment, the compound of Formula (I) or a pharmaceutically acceptable salt thereof as defined in the Summary and embodiments (A), (B), (C), (D), (E), and (F) above and embodiments contained therein, is where $R_1$ is a ring of formula

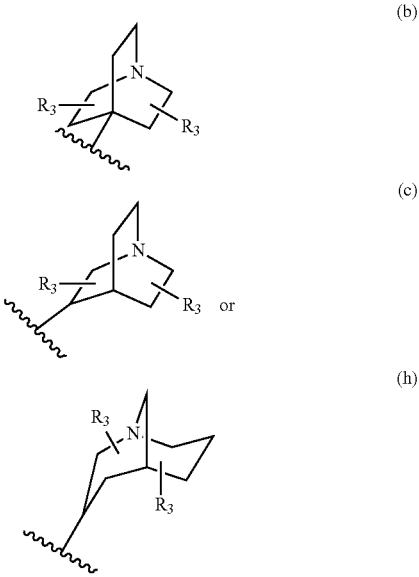

(a1) Within groups in embodiment (H), in one group of compounds $R_1$ is a ring of formula (c) or (h). Within this embodiment, in one group of compounds the stereochemistry at the chiral carbon is (R) or (S).

(b1) Within groups in embodiment (H), in one group of compounds $R^1$ is a ring of formula (b).

(vi) Within groups in embodiment (H) and embodiments contained therein i.e., (a1) and (b1) and groups contained therein, in one group of compounds each $R_3$ is independently hydrogen or methyl. Within these groups of compounds in one group of compounds each $R_3$ is hydrogen.

Embodiment I

In another embodiment, the compound of Formula (I) or a pharmaceutically acceptable salt thereof as defined in the Summary and embodiments (A), (B), (C), (D), (E), (F), (G), and (H) above and groups contained therein, in one group of compounds, each of $X_1$, $X_2$, $X_3$, and $X_4$ is $CR_5$ and $X_5$ is N or $CR_6$. Within this embodiment, in another group of compounds each $R_5$ is hydrogen.

(c1) Within the groups in embodiment I, in one group of compounds, $X_5$ is N.

(d1) Within the groups in embodiment I, in another group of compounds $X_5$ is $CR_6$. Within these groups of compounds, in one group of compounds $X_5$ is $CR_6$ and $R_6$ is hydrogen.

Within the groups in embodiment I, in another group of compounds one of $R_5$ is fluoro, or cyano. Within this group of compounds, in another group the $R_5$ cyano is located at C-5 position, the nitrogen atom substituted with $R_4$ being position 1. Within this group of compounds, in another group of compounds in another group the $R_5$ fluoro is located at C-5 position, the nitrogen atom substituted with $R^4$ being position 1.

Embodiment J

In another embodiment, the compound of Formula (I) or a pharmaceutically acceptable salt thereof as defined in the Summary and embodiments (A), (B), (C), (D), (E), (F), and (G), and (H) above and groups is where one of $X_1$, $X_2$, $X_3$, or $X_4$ is N and $X_5$ is N or $CR_6$. Within these groups of compounds in one group of compounds $X_1$ is N.

(e1) Within the groups in embodiment J, in one group of compounds $X_5$ is N.

(f1) Within the groups in embodiment J, in another group of compounds $X_5$ is $CR_6$ and $R_6$ is hydrogen.

Within the groups in embodiment J, in one group of compounds each $R_5$ is hydrogen.

Within the groups in embodiment J, (e1) and (f1), in another group of compounds one of $R_5$ is fluoro, or cyano. Within this group of compounds, in another group the $R_5$ cyano is located at C-5 position, the nitrogen atom substituted with $R_4$ being position 1. Within this group of compounds, in another group of compounds in another group the $R_5$ fluoro is located at C-5 position, the nitrogen atom substituted with $R_4$ being position 1.

Embodiment K

In another embodiment, the compound of Formula (I) or a pharmaceutically acceptable salt thereof as defined in the Summary and embodiments (E), (F), (G), and (H) above and groups contained therein, in one group of compounds each of $X_1$-$X_4$ is $CR_5$ or one of $X_1$-$X_4$ is N and $X_5$ is $CR_6$ where $R_6$ together with $R_4$ forms —O—$(CH_2)_2$— or —O—$(CH_2)_3$—.

(g1) Within the groups in embodiment K, in one group of compounds each $X_1$-$X_4$ is $CR_5$.

(h1) Within the groups in embodiment I, in another group of compounds one of $X_1$-$X_4$ is N. Within the groups in embodiment K, (g1) and (h1), in one group of compounds each $R_5$ is hydrogen.

Within these groups of compounds, in one group of compounds $X_1$ is N.

Within the groups in embodiment K, (g1) and (h1), in another group of compounds one of $R_5$ is fluoro, or cyano.

Within this group of compounds, in another group the $R_5$ cyano is located at C-5 position, the nitrogen atom substituted with $R_4$ being position 1. Within this group of compounds, in another group of compounds in another group the $R_5$ fluoro is located at C-5 position, the nitrogen atom substituted with $R_4$ being position 1. Compounds of Formula (IA):

Embodiment (A1)

In one embodiment, the compound of Formula (IA) or a pharmaceutically acceptable salt thereof, as defined in the Summary is where $R_4$ is $C_{1-6}$ haloalkyl. Within this embodiment, in another group of compounds $R_4$ is 2,2,2-trifluoroethyl, 2,2-difluoroethyl, 2-fluoroethyl, 1,2,2,2-tetrafluoroethyl, 1,1,2,2,-tetrafluoroethyl, 1,1,1-trifluoro-2-methylpropan-2-yl, (R)-1,2,2,2-tetrafluoroethyl, (S)-1,2,2,2-tetrafluoroethyl, or 2,2-difluoropropyl. Within this embodiment, in another group of compounds $R_4$ is 2,2-difluoroethyl. Within this embodiment, in another group of compounds $R_4$ is 2,2,2-trifluoroethyl.

Embodiment (B1)

In another embodiment, the compound of Formula (IA) or a pharmaceutically acceptable salt thereof as defined in the Summary is where $R_4$ is $C_{1-6}$ alkylsulfonyl or $C_{3-8}$ cycloalkylsulfonyl. Within this embodiment, in one group of compounds $R_4$ is $C_{1-6}$ alkylsulfonyl, preferably methylsulfonyl, ethylsulfonyl, or isopropylsulfonyl. Within this embodiment, in another group of compounds $R_4$ is methylsulfonyl. Within this embodiment, in another group of compounds $R_4$ is isopropylsulfonyl. Within this embodiment, in another group of compounds $R_4$ is $C_{3-8}$ cycloalkylsulfonyl.

Embodiment (C1)

In another embodiment, the compound of Formula (IA) or a pharmaceutically acceptable salt thereof as defined in the Summary is where $R_4$ is $C_{3-6}$ heterocycloalkyl optionally substituted with one or two substituents independently selected from $C_{1-6}$ alkyl, $C_{1-6}$ alkoxy, $C_{1-6}$ haloalkoxy, $C_{1-6}$ alkylsulfonyl, or halo. Within this embodiment, in one group of compounds $R_4$ is tetrahydrofuranyl, pyrrolidinyl, azetidinyl, or piperidinyl. Within this embodiment, in one group of compounds $R_4$ is RS, R, or S tetrahydrofuran-3-yl.

Embodiment (D1)

In another embodiment, the compound of Formula (IA) or a pharmaceutically acceptable salt thereof as defined in the Summary is where $R_4$ is $C_{3-6}$ oxoheterocycloalkyl optionally substituted with one or two substituents independently selected from $C_{1-6}$ alkyl, $C_{1-6}$ alkoxy, $C_{1-6}$ haloalkoxy, $C_{1-6}$ alkylsulfonyl, or halo.

Embodiment (E1)

In another embodiment, the compound of Formula (IA) or a pharmaceutically acceptable salt thereof as defined in the Summary is where $R_4$ is $C_{1-6}$ cyanoalkyl. Within this embodiment, in one group of compounds $R_4$ is cyanomethyl or 2-cyanoethyl.

Embodiment (F1)

In another embodiment, the compound of Formula (IA) or a pharmaceutically acceptable salt thereof as defined in the Summary is where $R_4$ is $C_{3-6}$ oxoheterocycloalkyl optionally substituted with one or two substituents independently selected from $C_{1-6}$ alkyl, $C_{1-6}$ alkoxy, $C_{1-6}$ haloalkoxy, $C_{1-6}$ alkylsulfonyl, or halo.

Within this embodiment, in one group of compounds $R_4$ is 1-methyl-2-oxo-1,2-dihydropyridin-4-yl, 1-methyl-2-oxo-1,2-dihydropyridin-5-yl, or 1-methyl-2-oxo-1,2-dihydropyridin-6-yl.

Embodiment (G1)

In another embodiment, the compound of Formula (IA) or a pharmaceutically acceptable salt thereof as defined in the Summary is where $R_4$ is phenyl optionally substituted with one, two, or three substituents independently selected from $C_{1-6}$ alkyl, $C_{1-6}$ haloalkyl, $C_{1-6}$ haloalkoxy, $C_{1-6}$ alkoxy, hydroxyl, cyano, or halo. Within this embodiment, in one group of compounds $R^4$ is phenyl optionally substituted with one, two, or three substituents independently selected from methyl, cyano, fluoro, chloro, hydroxyl, trifluoromethoxy or cyano.

Embodiment (H1)

In one embodiment, the compound of Formula (IA) or a pharmaceutically acceptable salt thereof as defined in the Summary and embodiments (A1), (B1), (C1), (D1), (E1), (F1), and (G1) above and embodiments contained therein, is where Z is O.

Embodiment (I1)

In one embodiment, the compound of Formula (IA) or a pharmaceutically acceptable salt thereof as defined in the Summary and embodiments (A1), (B1), (C1), (D1), (E1), (F1), and (G1) above and embodiments contained therein, is where Z is $NR_a$. Within this embodiment, in another group of compounds $R_a$ is hydrogen. Within this embodiment, in another group of compounds $R_a$ is methyl.

Embodiment (J1)

In one embodiment within embodiment J1, the compound of Formula (IA) or a pharmaceutically acceptable salt thereof as defined in the Summary and embodiments (A1), (B1), (C1), (D1), (E1), (F1), (G1), and (H1) above and embodiments contained therein, is where $R^1$ is as disclosed in Embodiment G and groups (a), (b), and (i)-(v) above.

Embodiment (K1)

In one embodiment within embodiment K1, the compound of Formula (IA) or a pharmaceutically acceptable salt thereof as defined in the Summary and embodiments (A1), (B1), (C1), (D1), (E1), (F1), (G1), and (H1) above and embodiments contained therein, is where $R_1$ is as disclosed in Embodiment H and groups (a1), (b1), and (vi) above, including groups contained therein.

Embodiment (L1)

In one embodiment within embodiment J1, the compound of Formula (IA) or a pharmaceutically acceptable salt thereof as defined in the Summary and embodiments (A1), (B1), (C1), (D1), (E1), (F1), (G1) (H1), (I1), (J1), and (K1) above and embodiments contained therein, $X_1$-$X_4$ and $X_5$ are as disclosed in Embodiment I and groups (e1), (d1) and groups contained therein above, including groups contained therein.

Embodiment (M1)

In one embodiment within embodiment M1, the compound of Formula (IA) or a pharmaceutically acceptable salt thereof as defined in the Summary and embodiments (A1), (B1), (C1), (D1), (E1), (F1), (G1) (H1), (I1), (J1) and (K1) above and embodiments contained therein, $X_1$-$X_4$ and $X_5$ are as in Embodiment J and groups (e1), (f1) including groups contained therein above.

Embodiment (N1)

In one embodiment within embodiment M1, the compound of Formula (IA) or a pharmaceutically acceptable salt thereof as defined in the Summary and embodiments (A1), (B1), (C1), (D1), (E1), (F1), (G1) (H1), (I1), (J1) and (K1) above and embodiments contained therein, $X_1$-$X_4$ and $X_5$ are as disclosed in Embodiment K and groups (f1), (h1) including groups contained therein above.

General Synthetic Scheme

Compounds of this invention can be made by the methods depicted in the reaction schemes shown below and other methods known in the art.

The starting materials and reagents used in preparing these compounds are either available from commercial suppliers such as Aldrich Chemical Co., (Milwaukee, Wis.), Bachem (Torrance, Calif.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), March's Advanced Organic Chemistry, (John Wiley and Sons, 4th Edition) and Larock's Comprehensive Organic Transformations (VCH Publishers Inc., 1989). These schemes are merely illustrative of some methods by which the compounds of this invention can be synthesized, and various modifications to these schemes can be made and will be suggested to one skilled in the art having referred to this disclosure. The starting materials and the intermediates, and the final products of the reaction may be isolated and purified if desired using conventional techniques, including but not limited to filtration, distillation, crystallization, chromatography and the like. Such materials may be characterized using conventional means, including physical constants and spectral data.

Unless specified to the contrary, the reactions described herein take place at atmospheric pressure over a temperature range from about −78° C. to about 150° C., more preferably from about 0° C. to about 12° C. and most preferably at about room (or ambient) temperature, e.g., about 20° C.

Compounds of Formula (I) can be prepared as illustrated and described in Scheme A below.

cycloalkysulfonyl halide in the presence of a suitable based such as triethylamine, pyridine, and the like, in a suitable organic solvent such as THF, DMF, and the like. When $R_4$ is heteroaryl, the C—N bond can either be formed by reacting heteroaryl halide with a compound of formula 1 by displacement of halide or by reacting heteroarylboronic acid with compound 1 under Chan-Lam coupling conditions. Compounds of formula 1, $R_4LG$, wherein LG is a leaving group such as sulfonate or halo, and $R_4B(OH)_2$, or ester thereof, are either commercially available or they can be prepared by methods well known in the art. For example 5-fluoro-2-methylindole-3-carboxylic acid ethyl ester, 4,5-difluoro-2-methylindole-3-carboxylic acid ethyl ester, 1H-indole-3-carboxylic acid, 5-methoxy-, methyl ester, 5-fluoro-1H-indole-3-carboxylic acid methyl ester, ethyl 5-methyl-1H-indole-3-carboxylate, 4,5-difluoro-2-methylindole-3-carboxylic acid ethyl ester, 5-cyano-2-methyl-1H-indole-3-carboxylic acid methyl ester, 1H-indazole-3-carboxylic acid, 5-cyano-6-fluoro-, methyl ester, 1H-indazole-3-carboxylic acid, 5-cyano-, methyl ester, 1H-indazole-3-carboxylic acid, 5-methoxy-, ethyl ester, 1H-indazole-3-carboxylic acid, 5-methyl-, ethyl ester, 1H-indazole-3-carboxylic acid, 5-fluoro-, ethyl ester, 1H-pyrazolo[3,4-b]pyridine-3-carboxylic acid, 5-fluoro-, methyl ester, 1H-pyrrolo[2,3-b]pyridine-3-carboxylic acid, 5-methyl-, methyl ester, 1H-pyrrolo[2,3-b]pyridine-3-carboxylic acid, 5-fluoro-, methyl ester, $CH_3I$, methylsulfonyl chloride, ethylsulfonyl chloride, isopropylsulfonyl Scheme A

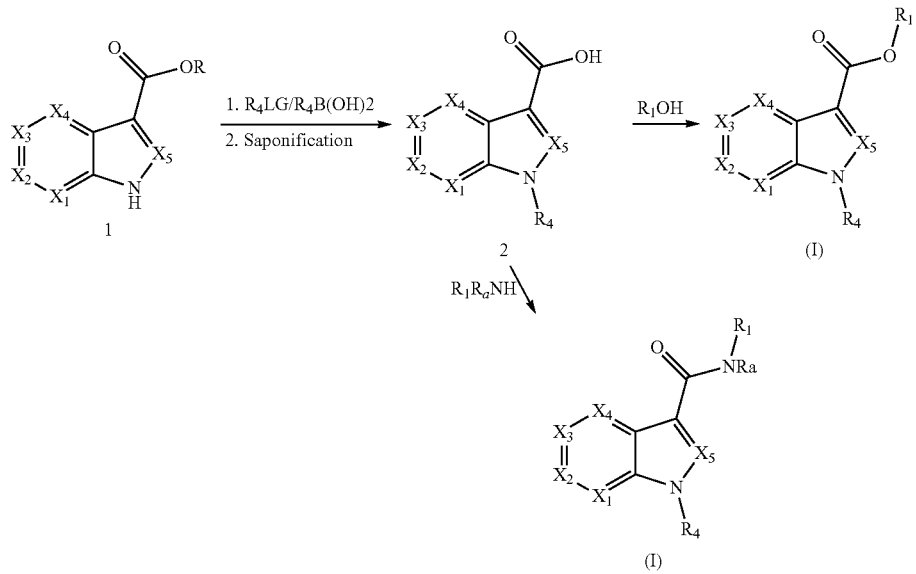

Step 1 involves formation of the C—N bond between $R_4$ and N-1 nitrogen of the compound of formula 1 where R is an acid protecting group such as $C_{1-6}$ alkyl. The reaction conditions utilized is based on the nature of the $R_4$ group. When $R_4$ is $C_{1-6}$ haloalkyl the reaction is carried out by heating compound 1 with an $C_{1-6}$ alkyl halide respectively or $C_{1-6}$ alkyl mesylate under standard alkylation reaction conditions e.g., in the presence of a base such as potassium carbonate, cesium carbonate, and the like, in a suitable organic solvent such as DMF, and the like. When $R_4$ is $C_{1-6}$ alkylsulfonyl or $C_{3-8}$ cycloalkylsulfonyl, the reaction is carried out by reacting compound 1 with $C_{1-6}$ alkylsulfonyl halide or $C_{3-8}$ chloride, cyclopropylsulfonyl chloride, 2-bromo-2,2,2-trifluoroethane, and 2-bromo-2,2-difluoroethane are commercially available.

Hydrolysis of the ester group under basic aqueous conditions provides the corresponding compound of formula 2. Compound 2 is then converted to a compound of Formula (I) where Z is $NR_a$ or O or nitrogen protected derivative thereof, by forming an activated acid derivative of compound 2, followed by reaction with $R_1R_aNH$ or $R_1OH$ where $R_1$ is as defined in the Summary or nitrogen protected derivative thereof. For example, the activated acid derivative can be mixed anhydride such as with a mixture of TFAA and TFA in toluene or CDI or Boc$_2$O; or acid halide such as with oxalyl chloride, thionyl chloride; or under standard using standard peptide coupling reagents such as HATU in the presence of a base such as N,N-diisopropylethylamine, and a solvent, such as DMF and the like. When nitrogen protected derivative of R$_1$R$_a$NH or R$_1$OH are used, removal of the protecting group provides the compound of Formula (I). Amines and alcohols of formula R$_1$R$_a$NH or R$_1$OH or nitrogen protected derivative thereof are either commercially available or they can be prepared by methods known in the art e.g., (1S,5R,6S)-4-oxa-1-azabicyclo[3.3.1]nonan-6-ol can be prepared as described in Journal of Medicinal Chemistry, 1993, 36, 683-689.

Alternatively, compound of Formula I can be synthesized by first coupling the acid derivative of compound 1 (R is H) with R$_1$R$_a$NH or R$_1$OH as described above, followed by formation of N—C bond as described in Step 1 of Scheme A above.

Detailed descriptions of synthesis of compounds of Formula (I) via above procedures are provided in Working Examples below.

Utility

5HT3 receptors are known to be expressed in the central nervous system in regions involving vomiting reflex, processing of pain, cognition and anxiety control and play a role in the pathogenesis of diseases such as emesis, migraine, drug addiction, and neurodegenerative and psychiatric disorders such as anxiety and depression (see Hewlett et al., 2003 *J. Clin. Psychiatry* 64, 1025-1030; Kelley et al., 2003a, *Eur J. Pharmacol.*, 461, 19-25; Haus et al., 2000 *Scand J Rheumatol Suppl* 113, 55-58; and Faris et al., 2006 *J affect Disorder* 92, 79-90), eating disorders (Hammer et al., 1990 *Am J Physiol* 259, R627-R636, and Jiang & Gietzen 1994 *Pharmacol Biochem Behav* 47, 59-63), schizophrenia (see Hermann et al. 1996 *Biochem Biophys Res Commun* 225, 957-960; Sirota et al., 2000 *Am J Psychiatry* 157, 287-289; Adler et al., 2005 *Am J Psychiatry* 162, 386-388; Koike et al., Levkovitz et al, 2005 *Schizophr Res* 76, 67-72), cognitive dysfunction associated with schizophrenia (see Zhang et al., 2006 *Schizophr Res* 88, 102-110; Akhondzadeh et al., 2009 *Schizophr Res* 107, 206-212), cognitive dysfunction associated with Parkinson's disease, Huntington's Chorea, presenile dementias and Alzheimer's disease (see Costall and Naylor 2004 *CNS Neurol Disord* 3, 27-37) substance abuse and addiction (see Johnson et al., 2002 *Psycho-pharmacology* (Berl) 160, 408-413; Johnson, 2004 *CNS Drugs* 18, 1105-1118; Dawes et al., 2005 *Addict Behav* 30, 1630-1637, Johnson 2006 *Drug Alcohol Depend* 84, 256-263), and pain (see Kayser et al, 2007 *Pain* 130, 235; Glaum et al., 1998 *Neurosci Lett* 95, 313-317; Schworer & Ramadori 1993 *Clin Investig* 71, 659; Thompson and Lummis 2007 *Exp Opin Ther Targets*, 11, 527-540). In addition, 5HT3 receptors are expressed in the GI tract and hence may play a role in GI disorders such as dyspepsia, gastroesophagal reflux disease and irritable bowel syndrome (see Graeff 1997 *Psychiatr Clin North Am* 20, 723; Thompson and Lummis 2007 *Exp Opin Ther Targets*, 11, 527-540; Barnes et al. 2009 *Neuropharmacology* 56, 273). Expression of the 5HT3A subunit has also been discovered extraneuronally in immune cells such as monocyes, chondrocytes, T-cells, synovial tissue and platelets (Fiebich et al., 2004 *Scan J Rheumatol Suppl*, 9-11, Stratz et al., 2008 *Thromb Haemost* 99, 784) and of 5HT3A, C-E within the lamina propia in the epithelium of the gut mucose (Kapeller et al., *J Comp Neuro.*, 2008; 509: 356-371) thus suggesting they may be involved in immunological and inflammatory diseases like atherosclerosis, tendomyopathies and fibromyalgia.

Testing

The 5HT3 inhibitory activity of the compounds of the present invention can be tested using the in vitro assay and in vivo assay described in Biological Example 1 and 2 below.

Administration and Pharmaceutical Composition

In general, the compounds of this invention will be administered in a therapeutically effective amount by any of the accepted modes of administration for agents that serve similar utilities. Therapeutically effective amounts of compounds of Formula (I) may range from about 0.01 to about 75 mg per kg patient body weight per day, which can be administered in single or multiple doses. Preferably, the dosage level will be about 0.01 to about 10 mg/kg per day; more preferably about 0.5 to about 5 mg/kg per day or 0.1-2 mg/kg/day. For oral administration, the compositions are preferably provided in the form of tablets containing about 0.5 to about 200 milligrams of the active ingredient, from about 0.5, 1.0, 5.0, 10, 15, 20, 25, 50, 75, 100, 150, or 200 milligrams of the active ingredient. The actual amount of the compound of this invention, i.e., the active ingredient, will depend upon numerous factors such as the severity of the disease to be treated, the age and relative health of the subject, the potency of the compound utilized, the route and form of administration, and other factors. Although these dosages are based on an average human subject having a mass of about 60 kg to about 70 kg, the physician will be able to determine the appropriate dose for a patient (e.g., an infant) whose mass falls outside of this weight range.

In general, compounds of this invention will be administered as pharmaceutical compositions by any one of the following routes: oral, systemic (e.g., transdermal, intranasal or by suppository), or parenteral (e.g., intramuscular, intravenous or subcutaneous) administration. The preferred manner of administration is oral using a convenient daily dosage regimen, which can be adjusted according to the degree of affliction. Compositions can take the form of tablets, pills, capsules, semisolids, powders, sustained release formulations, solutions, suspensions, elixirs, aerosols, or any other appropriate compositions.

The choice of formulation depends on various factors such as the mode of drug administration (e.g., for oral administration, formulations in the form of tablets, pills or capsules are preferred) and the bioavailability of the drug substance. Recently, pharmaceutical formulations have been developed especially for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from 10 to 1,000 nm in which the active material is supported on a crosslinked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

The compositions are comprised of in general, a compound of formula (I) in combination with at least one pharmaceutically acceptable excipient. Acceptable excipients are non-toxic in the amount used, aid administration, and do not adversely affect the therapeutic benefit of the compound of formula (I). Such excipient may be any solid, liquid, semisolid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose, and glycols.

Compressed gases may be used to disperse a compound of this invention in aerosol form. Inert gases suitable for this purpose are nitrogen, carbon dioxide, etc.

Other suitable pharmaceutical excipients and their formulations are described in Remington's Pharmaceutical Sciences, edited by E. W. Martin (Mack Publishing Company, 18th ed., 1990).

The level of the compound in a formulation can vary within the full range employed by those skilled in the art. Typically, the formulation will contain, on a weight percent (wt %) basis, from about 0.01-99.99 wt % of a compound of formula (I) based on the total formulation, with the balance being one or more suitable pharmaceutical excipients. Preferably, the compound is present at a level of about 1-80 wt %.

The compounds of the present invention may be used in combination with one or more other drugs in the treatment of diseases or conditions for which compounds of the present invention or the other drugs may have utility, where the combination of the drugs together are safer or more effective than either drug alone. Such other drug(s) may be administered, by a route and in an amount commonly used therefore, contemporaneously or sequentially with a compound of the present invention. When a compound of the present invention is used contemporaneously with one or more other drugs, a pharmaceutical composition in unit dosage form containing such other drugs and the compound of the present invention can be used. However, the combination therapy may also include therapies in which the compound of the present invention and one or more other drugs are administered on different overlapping schedules. It is also contemplated that when used in combination with one or more other active ingredients, the compounds of the present invention and the other active ingredients may be used in lower doses than when each is used singly.

Accordingly, the pharmaceutical compositions of the present invention also include those that contain one or more other active ingredients, in addition to a compound of the present invention.

The above combinations include combinations of a compound of the present invention not only with one other active compound, but also with two or more other active compounds. Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefore, contemporaneously or sequentially with a compound of the present invention. Accordingly, the pharmaceutical compositions of the present invention also include those that also contain one or more other active ingredients, in addition to a compound of the present invention. The weight ratio of the compound of the present invention to the second active ingredient may be varied and will depend upon the effective dose of each ingredient. Generally, an effective dose of each will be used.

In one embodiment, the compound of the present invention may be administered in combination with anti-Alzheimer's agents, beta-secretase inhibitors, gamma-secretase inhibitors, HMG-CoA reductase inhibitors, NSAID's including ibuprofen, vitamin E, and anti-amyloid antibodies. In another embodiment, the compound of the present invention may be administered in combination with sedatives, hypnotics, anxiolytics, antipsychotics, antianxiety agents, cyclopyrrolones, imidazopyridines, pyrazolopyrimidines, minor tranquilizers, melatonin agonists and antagonists, melatonergic agents, benzodiazepines, barbiturates, mGlu2/3 agonists, 5HT-2 antagonists, PDE10 antagonists, GlyT1 inhibitors, and the like, such as: adinazolam, allobarbital, alonimid, alprazolam, amisulpride, amitriptyline, amobarbital, amoxapine, aripiprazole, bentazepam, benzoctamine, brotizolam, bupropion, busprione, butabarbital, butalbital, capuride, carbocloral, chloral betaine, chloral hydrate, clomipramine, clonazepam, cloperidone, clorazepate, chlordiazepoxide, clorethate, chlorpromazine, clozapine, cyprazepam, desipramine, dexclamol, diazepam, dichloralphenazone, divalproex, diphenhydramine, doxepin, estazolam, ethchlorvynol, etomidate, fenobam, flunitrazepam, flupentixol, fluphenazine, flurazepam, fluvoxamine, fluoxetine, fosazepam, glutethimide, halazepam, haloperidol, hydroxyzine, imipramine, lithium, lorazepam, lormetazepam, maprotiline, mecloqualone, melatonin, mephobarbital, meprobamate, methaqualone, midaflur, midazolam, nefazodone, nisobamate, nitrazopam, nortriptyline, olanzapine, oxazepam, paraldehyde, paroxetine, pentobarbital, perlapine, perphenazine, phenelzine, phenobarbital, prazepam, promethazine, propofol, protriptyline, quazepam, quetiapine, reclazepam, risperidone, roletamide, secobarbital, sertraline, suproclone, temazepam, thioridazine, thiothixene, tracazolate, kanylcypromaine, trazodone, triazolam, trepipam, tricetamide, triclofos, trifluoperazine, trimetozine, trimipramine, uldazepam, venlafaxine, zaleplon, ziprasidone, zolazepam, zolpidem, [4-(3-fluoro-5-trifluoromethylpyridin-2-yl)piperazin-1-yl][5-methanesulfonyl-2-((S)-2,2,2-trifluoro-1-methylethoxy)phenyl]methanone (RG1678), glyt1 inhibitors disclosed in U.S. Pat. No. 7,538,114, Table 1 in column 14, and salts thereof, and combinations thereof.

In another embodiment, the compound of the present invention may be administered in combination with levodopa (with or without a selective extracerebral decarboxylase inhibitor such as carbidopa or benserazide), anticholinergics such as biperiden (optionally as its hydrochloride or lactate salt) and trihexyphenidyl (benzhexol) hydrochloride, COMT inhibitors such as entacapone, MOA-B inhibitors, antioxidants, A2a adenosine receptor antagonists, cholinergic agonists, NMDA receptor antagonists, serotonin receptor antagonists and dopamine receptor agonists such as alentemol, bromocriptine, fenoldopam, lisuride, naxagolide, pergolide and pramipexole. It will be appreciated that the dopamine agonist may be in the form of a pharmaceutically acceptable salt, for example, alentemol hydrobromide, bromocriptine mesylate, fenoldopam mesylate, naxagolide hydrochloride and pergolide mesylate. Lisuride and pramipexol are commonly used in a non-salt form.

In another embodiment, the compound of the present invention may be administered in combination with a compound from the phenothiazine, thioxanthene, heterocyclic dibenzazepine, butyrophenone, diphenylbutylpiperidine and indolone classes of neuroleptic agent. Suitable examples of phenothiazines include chlorpromazine, mesoridazine, thioridazine, acetophenazine, fluphenazine, perphenazine and trifluoperazine. Suitable examples of thioxanthenes include chlorprothixene and thiothixene. An example of a dibenzazepine is clozapine. An example of a butyrophenone is haloperidol. An example of a diphenylbutylpiperidine is pimozide. An example of an indolone is molindolone. Other neuroleptic agents include loxapine, sulpiride and risperidone. It will be appreciated that the neuroleptic agents when used in combination with the subject compound may be in the form of a pharmaceutically acceptable salt, for example, chlorpromazine hydrochloride, mesoridazine besylate, thioridazine hydrochloride, acetophenazine maleate, fluphenazine hydrochloride, flurphenazine enathate, fluphenazine decanoate, trifluoperazine hydrochloride, thiothixene hydrochloride, haloperidol decanoate, loxapine succinate and molindone hydrochloride. Perphenazine, chlorprothixene, clozapine, haloperidol, pimozide and risperidone are commonly used in a non-salt form. Thus, the compound of the present invention may be administered in combination with acetophenazine, alentemol, aripiprazole, amisulpride, benzhexol, bromocriptine, biperiden, chlorpromazine, chlorprothixene, clozapine, diazepam, fenoldopam, fluphenazine, haloperidol, levodopa, levodopa with benserazide, levodopa with carbidopa, lisuride, loxapine, mesoridazine, molindolone, naxagolide, olanzapine, pergolide, perphenazine, pimozide, pramipexole, quetiapine, risperidone, sulpiride, tetrabenazine, trihexyphenidyl, thioridazine, thiothixene, trifluoperazine or ziprasidone.

In another embodiment, the compound of the present invention may be administered in combination with an antidepressant or anti-anxiety agent, including norepinephrine reuptake inhibitors (including tertiary amine tricyclics and secondary amine tricyclics), selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRls), corticotropin releasing factor (CRF) antagonists, adrenoreceptor antagonists, neurokinin-1 receptor antagonists, atypical antidepressants, benzodiazopines, 5HTA agonists or antagonists, especially 5HTA partial agonists, and corticotropin releasing factor (CRF) antagonists. Specific agents include: amitriptyline, clomipramine, doxepin, imipramine and trimipramine; amoxapine, desipramine, maprotiline, nortriptyline and protriptyline; fluoxetine, fluvoxamine, paroxetine and sertraline; isocarboxazid, phenelzine, tranylcypromine and selegiline; moclobemide, venlafaxine; duloxetine; aprepitant; bupropion, lithium, nefazodone, trazodone and viloxazine; alprazolam, chlordiazepoxide, clonazepam, chlorazepate, diazopam, halazepam, lorazepam, oxazopam and prazepam; buspirone, flesinoxan, gepirone and ipsapirone, and pharmaceutically acceptable salts thereof.

EXAMPLES

The following preparations of compounds of Formula (I) are given to enable those skilled in the art to more clearly understand and to practice the present invention. They should not be considered as limiting the scope of the invention, but merely as being illustrative and representative thereof.

Synthetic Procedures

Reference 1

Synthesis of (1R,5S,7S)-tert-butyl 7-hydroxy-3-oxa-9-azabicyclo[3.3.1]nonane-9-carboxylate

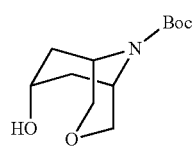

Sodium borohydride (259 mg, 6.84 mmol) was added portion-wise to a solution of (1R,5S)-tert-butyl 7-oxo-3-oxa-9-azabicyclo[3.3.1]nonane-9-carboxylate (550 mg, 2.279 mmol) in MeOH (4559 µl) at 0° C. After 5 min, the reaction mixture was allowed to warm to RT then stirred for 30 min. The mixture was concentrated under reduced pressure, dissolved in EtOAc and washed with brine. The combined organic layers were dried over anhydrous $Na_2SO_4$, filtered and concentrated under reduced pressure to afford the title compound as a white solid, which was used without further purification.

Reference 2

Synthesis of (1R,5S,7S)-9-methyl-$d_3$-oxa-9-azabicyclo[3.3.1]nonan-7-amine

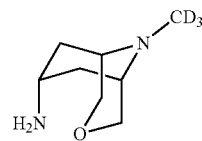

Step 1: (1R,5S)-9-Methyl-$d_3$-oxa-9-azabicyclo[3.3.1]nonan-7-one

To a solution of sodium dihydrogenphosphate hydrate (22.30 g, 162 mmol) and 2-hydroxypropane-1,2,3-tricarboxylic acid (4.90 g, 25.5 mmol) in water (Volume: 506 ml) was added in turn methyl-$d_3$-amine hydrogen chloride (5 g, 70.9 mmol) and 3-oxopentanedioic acid (11.91 g, 82 mmol). The pH was adjusted to 4.6 with a 10% aqueous solution of NaOH. A solution of 2,2'-oxydiacetaldehyde (3.62 g, 35.4 mmol) in 8 mL MeOH was added at RT and the resulting mixture was stirred at RT for 3 days. 10% aqueous NaOH was used to basify the reaction solution, and extracted with DCM (100 mL). Purification with column chromatography ($SiO_2$; DCM/MeOH) gave the title compound as a white solid.

Step 2: (1R,5S)-9-methyl-$d_3$-3-oxa-9-azabicyclo[3.3.1]nonan-7-one oxime

A solution of (1R,5S)-9-methy-$d_3$-oxa-9-azabicyclo[3.3.1]nonan-7-one (1.65 g, 10.43 mmol), hydroxylamine hydrochloride (0.761 g, 10.95 mmol) and pyridine (0.843 ml, 10.43 mmol) in EtOH (Volume: 52.1 ml) was heated at 75° C. for 3 h. After 0.2 mL of triethylamine was added to the reaction solution, the solvent was removed. Purification by column chromatography ($SiO_2$; DCM/MeOH) gave the title compound as a white solid.

Step 3: (1R,5S,7S)-9-Methyl-$d_3$-oxa-9-azabicyclo[3.3.1]nonan-7-amine

Sulfuric acid (1.108 ml, 20.78 mmol) was added dropwise over 15 min to a well-stirred solution of aluminum(III) lithium hydride (1.0 M in THF, 41.6 ml, 41.6 mmol) in THF (Volume: 41.6 ml) at 0° C. The mixture was stirred for another hour at 0° C. and then (1R,5S)-9-methyl-d3-3-oxa-9-azabicyclo[3.3.1]nonan-7-one oxime (1.8 g, 10.39 mmol) was added portionwise at 0° C. The reaction mixture was heated under reflux (80° C.) for 1.5 h. To the well-stirred reaction mixture, 1.58 mL of water, 2.37 mL of 10 M NaOH and 3.95 mL of water were subsequently added at 0° C. The resultant suspension was filtered through a pad of Celite and washed with THF. The combined organic phase was concentrated under reduced pressure to afford the title compound as a pale-yellow oil, which was used without further purification.

Reference 3

Synthesis of (1R,5S,7S)-9-(trifluoromethyl)-3-oxa-9-azabicyclo[3.3.1]nonan-7-amine 2,2,2-trifluoroacetate

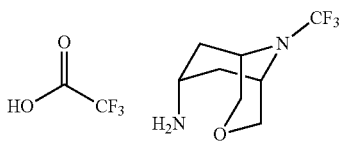 [SMILES: O=C(O)C(F)(F)F ; NC1CC2COCC(C1)N2C(F)(F)F]

Step 1: Benzyl (1R,5S,7S)-3-oxa-9-azabicyclo[3.3.1]nonan-7-ylcarbamate

Benzyl chloroformate (330 µl, 2.319 mmol) was added to a solution of (1R,5S,7S)-tert-butyl 7-amino-3-oxa-9-azabicyclo[3.3.1]nonane-9-carboxylate 2,2,2-trifluoroacetate (751.3 mg, 2.108 mmol) and triethylamine (619 µl, 4.43 mmol) in DCM (10 ml) at RT. After 14 h, trifluoroacetic acid (2.4 mL, 31.6 mmol) was added to the reaction mixture. After 15 min, the mixture was concentrated, dissolved with DMF, filtered, and purified by HPLC followed by neutralization ($K_2CO_3$) to afford the title compound as a colorless oil.

Step 2: Benzyl ((1R,5S,7S)-9-(trifluoromethyl)-3-oxa-9-azabicyclo[3.3.1]nonan-7-yl)carbamate A solution of benzyl (1R,5S,7S)-3-oxa-9-azabicyclo[3.3.1]nonan-7-ylcarbamate (27 mg, 0.098 mmol) and dibromodifluoromethane (18.06 µl, 0.195 mmol) in DMSO (489 µl) was treated with tetrakis(dimethylamino)ethylene (50.1 µl, 0.215 mmol), dropwise at 0° C. The mixture slowly warmed to RT overnight then was poured into a 1:1 mixture of $NaHCO_3/Na_2S_2O_3$ and extracted twice with $Et_2O$. The combined extracts were concentrated and purified by prep-TLC to give the title compound as a yellow oil.

Step 3: (1R,5S,7S)-9-(Trifluoromethyl)-3-oxa-9-azabicyclo[3.3.1]nonan-7-amine 2,2,2-trifluoroacetate In a vial containing benzyl ((1R,5S,7S)-9-(trifluoromethyl)-3-oxa-9-azabicyclo[3.3.1]nonan-7-yl)carbamate (10 mg, 0.029 mmol), palladium on carbon (10 wt %, 1.020 mg, 9.58 µmol), and TFA (4.47 µl, 0.058 mmol) in MeOH (Volume: 145 µl) was purged with hydrogen gas and left under 1 atm $H_2$ atmosphere for 2 h. Filtration through a pad of Celite/$MgSO_4$ (1:1) followed by concentration gave the title compound as a colorless film, which was used without further purification.

Reference 4

Synthesis of (1S,5R,6S)-4-oxa-1-azabicyclo[3.3.1]nonan-6-ol; (1R,5S,6R)-4-oxa-1-azabicyclo[3.3.1]nonan-6-ol

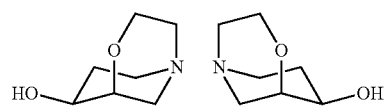

Step 1: Ethyl 4-(3-ethoxy-3-oxopropyl)morpholine-2-carboxylate

A mixture of ethyl morpholine-2-carboxylate (3 g, 18.85 mmol) and ethyl acrylate (5 ml, 18.85 mmol) was heated at 100° C. for 14 h. The reaction was cooled to RT then diluted with $Et_2O$ and extracted with aqueous 3M HCl. The combined aqueous layers were basified by solid $K_2CO_3$ and extracted with DCM. The combined organic layers were dried over anhydrous $Na_2SO_4$, filtered and concentrated under reduced pressure to afford the title compound as a pale-yellow oil, which was used without further purification.

Step 2: (1S,5R)-4-Oxa-1-azabicyclo[3.3.1]nonan-6-one (1R,5S)-4-Oxa-1-azabicyclo[3.3.1]nonan-6-one A solution of ethyl 4-(3-ethoxy-3-oxopropyl)morpholine-2-carboxylate (3.07 g, 11.84 mmol) in toluene (8 ml) was added to a suspension of potassium 2-methylpropan-2-olate (3.65 g, 32.6 mmol) in toluene (39.5 ml) at 120° C. After being stirred at 120° C. for 3 h, the reaction mixture was cooled to RT and extracted with water (20 mL). The aqueous layer was treated with conc. HCl (20 ml, 240 mmol) then heated at 110° C. for 14 h. The reaction mixture was cooled to RT then concentrated under reduced pressure. The resulting solid was taken up in saturated aq. $K_2CO_3$ and extracted with DCM. The combined organic layers were dried over anhydrous $Na_2SO_4$, filtered and concentrated under reduced pressure to afford the title compounds as a brown oil, which was used without further purification.

Step 3: (1S,5R,6S)-4-Oxa-1-azabicyclo[3.3.1]nonan-6-ol; (1R,5S,6R)-4-Oxa-1-azabicyclo[3.3.1]nonan-6-ol Sodium borohydride (53.6 mg, 1.417 mmol) was added to a solution of (1S,5R)-4-oxa-1-azabicyclo[3.3.1]nonan-6-one and (1R,5S)-4-oxa-1-azabicyclo[3.3.1]nonan-6-one (100 mg, 0.708 mmol) in MeOH (3542 µl) at 0° C. The reaction mixture was stirred at RT for 30 min, then concentrated under reduced pressure. The residue was taken up in EtOAc and washed with brine. The organic layer was dried over anhydrous $Na_2SO_4$, filtered and concentrated under reduced pressure to afford the title compounds as a yellow oil, which was used without further purification Reference 5

Synthesis of 1-(pyrimidin-5-yl)-1H-indole-3-carboxylic acid

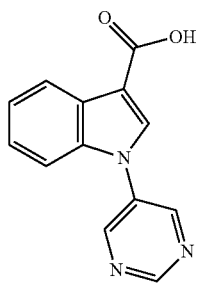 [SMILES: O=C(O)c1cn(-c2cncnc2)c2ccccc12]

Step 1: Methyl 1-(pyrimidin-5-yl)-1H-indole-3-carboxylate

To a vial containing methyl 1H-indole-3-carboxylate (471 mg, 2.69 mmol), pyrimidin-5-ylboronic acid (1.0 g, 8.07 mmol), copper (II) acetate (635 mg, 3.5 mmol), 4 Å molecular sieves (4 g) and 1,10-phenanthroline (970 mg, 5.38 mmol) were added DCM (10.7 ml) and triethylamine (0.375 ml, 2.69 mmol). The mixture was stirred at RT for 7 days then filtered through a pad of Celite (washed with MeOH). Evaporation and purification by HPLC (after dilution with DMF and filtration) afforded the title compound as a tan solid.

Step 2: 1-(pyrimidin-5-yl)-1H-indole-3-carboxylic acid

To a solution of methyl 1-(pyrimidin-5-yl)-1H-indole-3-carboxylate (16 mg, 0.063 mmol) in water MeOH (316 µl) was added 2M KOH (158 µl, 0.316 mmol). The mixture was heated at 80° C. for 4 h then neutralized with 1M HCl. The precipitate was collected by filtration to afford the title compound as a white solid, which was used without further purification.

Proceeding as described above 1-(pyrimidin-5-yl)-1H-indole-3-carboxylic acid was prepared.

Reference 6

Synthesis of 1-(pyrimidin-2-yl)-1H-indole-3-carboxylic acid

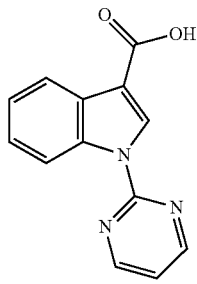 [SMILES: O=C(O)c1cn(-c2ncccn2)c2ccccc12]

Step 1: methyl 1-(pyrimidin-2-yl)-1H-indole-3-carboxylate

To a suspension of sodium hydride (46 mg, 1.142 mmol, 60% dispersion in mineral oil) in DMF (1.1 mL) was added methyl 1H-indole-3-carboxylate (200 mg, 1.142 mmol) and 2-chloropyrimidine (131 mg, 1.142 mmol). The resulting suspension was stirred at RT for 1 h. The reaction mixture was diluted with DMF, filtered, and purified by HPLC to afford the title compound as a white-pink solid.

Step 2: 1-(pyrimidin-2-yl)-1H-indole-3-carboxylic acid

The title compound was synthesized by utilizing similar conditions as described in Reference 5, Step 2.

Proceeding as described above, 1-(pyrazin-2-yl)-1H-indole-3-carboxylic acid was synthesized.

Reference 7

Synthesis of 1-(thiazol-2-yl)-1H-indole-3-carboxylic acid

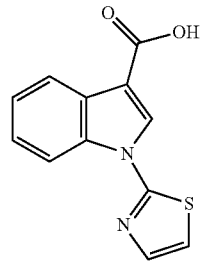 [SMILES: O=C(O)c1cn(-c2nccs2)c2ccccc12]

Step 1: Methyl 1-(thiazol-2-yl)-1H-indole-3-carboxylate

To a solution of methyl 1H-indole-3-carboxylate (200 mg, 1.142 mmol) in NMP (Volume: 1142 µl) were added 2-bromothiazole (206 µl, 2.283 mmol) and cesium carbonate (1116 mg, 3.42 mmol) at RT. The mixture was heated at 110° C. for 2 h, then diluted with DMF, filtered and purified by HPLC to afford the title compound as a brown solid.

Step 2: 1-(Thiazol-2-yl)-1H-indole-3-carboxylic acid

The title compound was synthesized by utilizing similar conditions as described in Reference 5, Step 2.

Proceeding as described above, 1-(pyridazin-3-yl)-1H-indole-3-carboxylic acid; and 1-(thiazol-5-yl)-1H-indole-3-carboxylic acid was synthesized.

Reference 8

Synthesis of 1-(1,1,1-trifluoro-2-methylpropan-2-yl)-1H-pyrrolo[2,3-b]pyridine-3-carboxylic acid

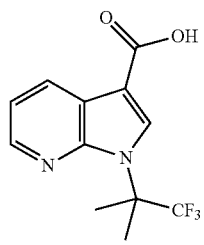 [SMILES: CC(C)(n1cc(C(=O)O)c2cccnc21)C(F)(F)F]

Step 1: 2-(((1,1,1-Trifluoro-2-methylpropan-2-yl) amino)methylene)succinonitrile A solution of ethyl formate (330 mg, 4.46 mmol) and succinonitrile (300 mg, 3.75 mmol) in toluene (1561 µl) was added dropwise to a suspension of sodium methanolate (215 mg, 3.97 mmol) in toluene (1561 µl) at 0° C. After being stirred at RT for 3 h, the reaction mixture was treated with 1,1,1-trifluoro-2-methylpropan-2-amine (486 mg, 3.82 mmol) and acetic acid (255 µl, 4.46 mmol) then heated at 120° C. for 3 h. After being cooled to RT, the reaction mixture was washed with brine, then dried over anhydrous $Na_2SO_4$, filtered and concentrated under reduced pressure to afford the title compound as a brown oil, which was used without further purification.

Step 2: 5-Amino-1-(1,1,1-trifluoro-2-methylpropan-2-yl)-1H-pyrrole-3-carbonitrile A solution of 2-(((1,1,1-trifluoro-2-methylpropan-2-yl) amino)methylene)-succinonitrile (187.2 mg, 0.862 mmol) in EtOH (539 µl) was added to a solution of KOH (87 mg, 1.551 mmol) in water (539 µl) at RT. After being stirred at RT for 4 h, the reaction mixture was concentrated under reduced pressure. The residual brown solid was taken up in water and sonicated. The resulting precipitate was collected by filtration, dissolved in EtOAc, washed with brine, dried over anhydrous $Na_2SO_4$, filtered and concentrated under reduced pressure to afford the title compound as a brown solid, which was used without further purification.

Step 3: 1-(1,1,1-Trifluoro-2-methylpropan-2-yl)-1H-pyrrolo[2,3-b]pyridine-3-carbonitrile 4-Methylbenzenesulfonic acid (10.57 mg, 0.061 mmol) was added in one portion to a solution of 5-amino-1-(1,1,1-trifluoro-2-methylpropan-2-yl)-1H-pyrrole-3-carbonitrile (133.3 mg, 0.614 mmol) and 1,1,3,3-tetramethoxypropane (111 µl, 0.675 mmol) in toluene (1227 µl) at RT. The mixture was heated at 100° C. for 1 h and purified directly by HPLC to afford the title compound as a brown solid.

Step 4: 1-(1,1,1-Trifluoro-2-methylpropan-2-yl)-1H-pyrrolo[2,3-b]pyridine-3-carboxylic acid KOH (174 mg, 3.11 mmol) was added to a solution of 1-(1,1,1-trifluoro-2-methylpropan-2-yl)-1H-pyrrolo[2,3-b]pyridine-3-carbonitrile (78.7 mg, 0.311 mmol) in 1:1:1 THF/MeOH/water (621 µl) at RT. After being stirred at 100° C. for 4 h, the reaction mixture was acidified (pH=2-3) by conc. HCl and the resulting suspension was extracted with EtOAc. The combined organic layers were concentrated to afford the title compound as a brown foam, which was used without further purification.

Reference 9

Synthesis of 1-(methylsulfonyl)-1H-indazole-3-carboxylic acid

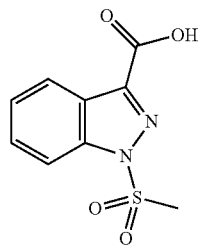 [SMILES: CS(=O)(=O)n1nc(C(=O)O)c2ccccc21]

Methanesulfonyl chloride (48.1 µl, 0.617 mmol) was added to a solution of 1H-indazole-3-carboxylic acid (100 mg, 0.617 mmol) and triethylamine (86 µl, 0.617 mmol) in THF (1542 µl) and the mixture was stirred for 1 h. The reaction was then poured into water and extracted twice with EtOAc. The combined organic layers were filtered through $MgSO_4$ and concentrated to give the title compound as a white solid, which was used without further purification.

Reference 10

Synthesis of 5-fluoro-1-(methylsulfonyl)-1H-indole-3-carboxylic acid

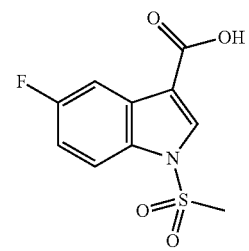 [SMILES: CS(=O)(=O)n1cc(C(=O)O)c2cc(F)ccc21]

Step 1: tert-Butyl 5-fluoro-1-(methylsulfonyl)-1H-indole-3-carboxylate

To a solution of tert-butyl 5-fluoro-1H-indole-3-carboxylate (500 mg, 2.125 mmol) and triethylamine (1721 mg, 17.00 mmol) in THF (5 ml) was added methanesulfonyl chloride (0.658 ml, 8.50 mmol). The mixture was stirred at RT for 2 h. The reaction mixture was then poured into water and extracted twice with $Et_2O$. The organic extracts were combined, filtered through $MgSO_4$, concentrated, and purified by column chromatography ($SiO_2$; EtOAc/hex) to afford the title compound as a white solid.

Step 2: 5-Fluoro-1-(methylsulfonyl)-1H-indole-3-carboxylic acid

A mixture of tert-butyl 5-fluoro-1-(methylsulfonyl)-1H-indole-3-carboxylate (150 mg, 0.479 mmol) and conc. HCl (0.2 ml, 2.394 mmol) in EtOAc (10 ml) was stirred at RT for 2 h. The mixture was then partially concentrated, and the resulting precipitate was collected by filtration, washed with EtOAc and dried in vacuo to afford the title compound as a white solid, which was used without further purification.

Reference 11

Synthesis of 5-fluoro-1-(isopropylsulfonyl)-1H-indole-3-carboxylic acid

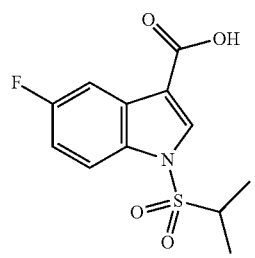 [SMILES: CC(C)S(=O)(=O)n1cc(C(=O)O)c2cc(F)ccc21]

Step 1: Methyl 1-(isopropylsulfonyl)-1H-indole-3-carboxylate

To a solution of methyl 1H-indole-3-carboxylate (0.234 g, 1.336 mmol) in THF (6.68 ml) was added sodium bis(trimethylsilyl)amide (2.67 ml, 2.67 mmol) at RT. After 30 min, propane-2-sulfonyl chloride (0.3 ml, 2.67 mmol) was added and the mixture was stirred for 2 h. The reaction mixture was then poured into brine and extracted twice with EtOAc. The combined extracts were filtered through $MgSO_4$ and concentrated to give the title compound as a brown solid, which was used without further purification.

Step 2: 5-Fluoro-1-(isopropylsulfonyl)-1H-indole-3-carboxylic acid

The title compound was synthesized by utilizing similar conditions as described in Reference 5, Step 2.

Proceeding as described above, 1-(isopropylsulfonyl)-1H-indole-3-carboxylic acid was synthesized.

Reference 12

Synthesis of (1R,5S,7s)-9-methyl-3-oxa-9-azabicyclo[3.3.1]nonan-7-yl 1H-indole-3-carboxylate

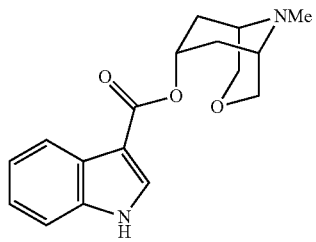 [SMILES: CN1C2COCC1CC(OC(=O)c1c[nH]c3ccccc13)C2]

To a solution of 1H-indole-3-carboxylic acid (250 mg, 1.551 mmol) in PhMe (5171 μl) was added TFAA (219 μl, 1.551 mmol) then TFA (1293 μl). The mixture was stirred for 30 min then commercially available (1R,5S,7s)-9-methyl-3-oxa-9-azabicyclo[3.3.1]nonan-7-(203 mg, 1.293 mmol) was added. The reaction mixture stirred at RT for 1 h then was poured into aq $NaHCO_3$ and stirred until pH=7 and bubbling stopped. The reaction mixture was extracted with EtOAc and dried over $MgSO_4$. Purification by ISCO (0-20% MeOH/DCM) yielded the title compound as a pink solid.

Reference 13

Synthesis of (1R,5S,7s)-tert-butyl 7-((1H-indole-3-carbonyl)oxy)-3-oxa-9-azabicyclo[3.3.1]nonane-9-carboxylate

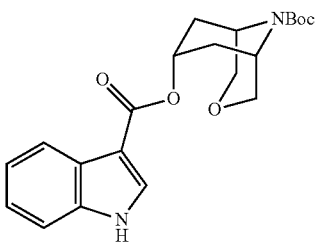 [SMILES: CC(C)(C)OC(=O)N1C2COCC1CC(OC(=O)c1c[nH]c3ccccc13)C2]

Step 1: (1R,5S,7s)-9-benzyl-3-oxa-9-azabicyclo[3.3.1]nonan-7-ol

Sodium borohydride (24.54 g, 649 mmol) was added portionwise over 30 min to a suspension of (1R,5S)-9-benzyl-3-oxa-9-azabicyclo[3.3.1]nonan-7-one (50 g, 216 mmol) in MeOH (540 ml) and THF (540 ml) at 0° C. The mixture was allowed to gradually warm to RT over 1 h. After an additional hour at RT, the mixture was concentrated and the white residue was partitioned between ethyl acetate and brine. The combined organic layers were dried over $Na_2SO_4$, filtered and concentrated under reduced pressure to afford the title compound as a white solid, which was used without further purification.

Step 2: (1R,5S,7s)-9-benzyl-3-oxa-9-azabicyclo[3.3.1]nonan-7-ol 2,2,2-Trifluoroacetic anhydride (34.5 ml, 244 mmol) and TFA (123 ml) were subsequently added to a solution of 1H-indole-3-carboxylic acid (39.4 g, 244 mmol) in toluene (987 ml) at RT. After 30 min, (1R,5S,7s)-9-benzyl-3-oxa-9-azabicyclo[3.3.1]nonan-7-ol (51.8 g, 222 mmol) was added to the mixture in one portion at RT. After 2 h, the mixture was concentrated under reduced pressure to the half of the original volume. Then, 800 mL of 10% $Na_2CO_3$ (aq) was added. The mixture was concentrated under reduced pressure until most of the organic solvent was removed. The product was extracted with ethyl acetate and the combined organic layers were washed with brine, dried over $Na_2SO_4$, filtered and concentrated under reduced pressure. The residual dark purple solid was triturated with $Et_2O$/EtOAc (4:1) to yield the title compound as a white-pink solid.

Step 3: (1R,5S,7s)-3-oxa-9-azabicyclo[3.3.1]nonan-7-yl 1H-indole-3-carboxylate, hydrogen chloride salt A suspension of (1R,5S,7s)-9-benzyl-3-oxa-9-azabicyclo[3.3.1]nonan-7-yl 1H-indole-3-carboxylate (2 g, 5.31 mmol) and palladium on carbon (200 mg, 1.879 mmol, 10 wt %) in EtOH (4.43 ml), THF (4.43 ml) and 3N HCl (4.43 ml) was stirred at RT under a hydrogen atmosphere (balloon) for 14 h. Then, the mixture was filtered through a pad of Celite and the filtrate was concentrated under reduced pressure to afford the title compound as a pink solid, which was used without further purification.

Step 4: (1R,5S,7s)-tert-butyl 7-((1H-indole-3-carbonyl)oxy)-3-oxa-9-azabicyclo[3.3.1]nonane-9-carboxylate Di-tert-butyl dicarbonate (1.275 g, 5.84 mmol) was added in one portion to a suspension of (1R,5S,7s)-3-oxa-9-azabicyclo[3.3.1]nonan-7-yl 1H-indole-3-carboxylate hydrochloride (1.714 g, 5.31 mmol) and triethylamine (1.628 ml, 11.68 mmol) in THF (26.6 ml) at RT. After 1 h, the mixture was partitioned between sat. $NH_4Cl$ (aq) and ethyl acetate. The aqueous layer was extracted with ethyl acetate and combined organic layers were washed with brine, dried over anhydrous $Na_2SO_4$, filtered and concentrated under reduced pressure to afford the title compound as a pale-brown oil, which was used without further purification.

Reference 14

Synthesis of 1-phenyl-1H-indole-3-carboxylic acid

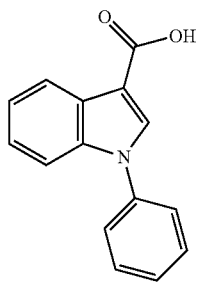 [SMILES: O=C(O)c1cn(-c2ccccc2)c2ccccc12]

Step 1: methyl 1-phenyl-1H-indole-3-carboxylate

A 5 mL screwtop vial containing methyl 1H-indole-3-carboxylate (100 mg, 0.571 mmol) and potassium phosphate (254 mg, 1.199 mmol) was degassed and purged with nitrogen after the addition of each of the following in sequential order: PhMe (1142 µl), bromobenzene (59.7 µl, 0.571 mmol), (1R,2R)—N1,N2-dimethylcyclohexane-1,2-diamine (54.4 µl, 0.342 mmol), and copper(I) iodide (32.6 mg, 0.171 mmol). The vial was sealed, wrapped in aluminum foil, and heated to 110° C. for 24 h. Concentration on silica gel and ISCO purification (20% EtOAc/hexanes) gave the title compound as a white solid.

Step 2: 1-phenyl-1H-indole-3-carboxylic acid

To a solution of methyl 1-phenyl-1H-indole-3-carboxylate (108 mg, 0.430 mmol) in MeOH (1433 µl) was added aq KOH (1074 µl, 2.149 mmol, 2 M). The mixture was heated at 90° C. for 1 h then the MeOH was removed under reduced pressure. The residual aqueous layer was acidified with 1M HCl then extracted with EtOAc. The combined organic layers were dried over anhydrous MgSO$_4$, filtered, and concentrated to afford the title compound as a white solid, which was used without further purification.

The following carboxylic acids were prepared by a similar procedure:
1-(isothiazol-4-yl)-1H-indole-3-carboxylic acid; 1-(isothiazol-3-yl)-1H-indole-3-carboxylic acid; 1-(isothiazol-5-yl)-1H-indole-3-carboxylic acid; and 1-(oxazol-2-yl)-1H-indole-3-carboxylic acid.

Reference 15

Synthesis of 1-(1-methyl-1H-imidazol-5-yl)-1H-indole-3-carboxylic acid

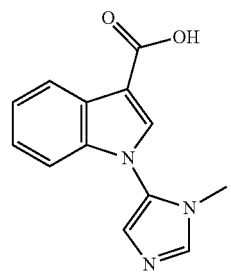 [SMILES: Cn1cncc1-n1cc(C(=O)O)c2ccccc21]

Step 1: methyl 1-(1-methyl-1H-imidazol-5-yl)-1H-indole-3-carboxylate

A solution of methyl 1H-indole-3-carboxylate (300 mg, 1.712 mmol) and 5-bromo-1-methyl-1H-imidazole (303 mg, 1.884 mmol) in toluene (3425 µl) was treated with (1R,2R)—N1,N2-dimethylcyclohexane-1,2-diamine (82 µl, 0.514 mmol), potassium phosphate (763 mg, 3.60 mmol) and copper(I) iodide (98 mg, 0.514 mmol) and the resulting reaction mixture stirred at 110° C. overnight. HPLC purification afforded the title compound as a yellow solid.

Step 2: 1-(1-methyl-1H-imidazol-5-yl)-1H-indole-3-carboxylic acid

A solution of methyl 1-(1-methyl-1H-imidazol-5-yl)-1H-indole-3-carboxylate (40 mg, 0.157 mmol) in THF (1567 µl) was treated with potassium trimethylsilanolate (223 mg, 1.567 mmol) in one portion at RT and the resulting reaction mixture stirred overnight. ISCO purification (10% MeOH/DCM) afforded the title compound as a white solid.

Reference 17

Synthesis of 1-(thiazol-2-yl)-1H-pyrrolo[2,3-b]pyridine-3-carboxylic acid

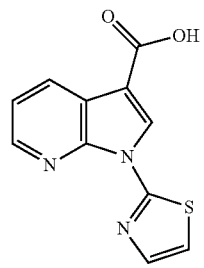 [SMILES: O=C(O)c1cn(-c2nccs2)c2ncccc12]

Step 1: methyl 1-(thiazol-2-yl)-1H-pyrrolo[2,3-b]pyridine-3-carboxylate

A mixture of methyl 1H-pyrrolo[2,3-b]pyridine-3-carboxylate (200 mg, 1.135 mmol), 2-bromothiazole (205 µl, 2.271 mmol) and cesium carbonate (1110 mg, 3.41 mmol) in NMP (1135 µl) was heated at 130° C. for 2 h. The mixture was then purified by HPLC to afford the title compound as a brownish-white solid.

Step 2: 1-(thiazol-2-yl)-1H-pyrrolo[2,3-b]pyridine-3-carboxylic acid

Potassium hydroxide (38.5 mg, 0.687 mmol) was added to a solution of methyl 1-(thiazol-2-yl)-1H-pyrrolo[2,3-b]pyridine-3-carboxylate (35.6 mg, 0.137 mmol) in MeOH (343 µl) and water (343 µl) at RT. The mixture was heated at 100° C. for 2 h. After cooling to RT, the mixture was acidified with 2 N HCl and then concentrated under reduced pressure. The crude mixture was used without further purification.

The following carboxylic acids were prepared by a similar procedure:
1-(thiazol-4-yl)-1H-pyrrolo[2,3-b]pyridine-3-carboxylic acid; 1-(thiazol-5-yl)-1H-pyrrolo[2,3-b]pyridine-3-carboxylic acid; 5-fluoro-1-(thiazol-2-yl)-1H-pyrrolo[2,3-b]pyridine-3-carboxylic acid; 5-fluoro-1-(thiazol-4-yl)-1H- pyrrolo[2,3-b]pyridine-3-carboxylic acid; 5-fluoro-1-(thiazol-5-yl)-1H-pyrrolo[2,3-b]pyridine-3-carboxylic acid and 1-(thiazol-5-yl)-1H-indazole-3-carboxylic acid.

Reference 18 tert-Butyl (1R,5S,7S)-7-(methylamino)-3-oxa-9-azabicyclo[3.3.1]nonane-9-carboxylate

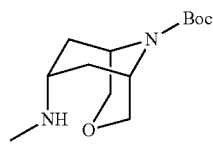 [SMILES: CNC1CC2COCC(C1)N2C(=O)OC(C)(C)C]

In a vial containing (1R,5S,7S)-tert-butyl 7-amino-3-oxa-9-azabicyclo[3.3.1]nonane-9-carboxylate (108.mg, 0.446 mmol) and formaldehyde (39.8 µl, 0.535 mmol) in DCE (Volume: 1114 µl) was added sodium triacetoxyborohydride (132 mg, 0.624 mmol) and stirred for 2 h. The mixture was poured into 10% NaOH, and extracted twice with DCM. The extracts were combined, filtered through MgSO₄, and concentrated to give the title compound.

Example 1

Synthesis of (1R,3R,5S)-8-methyl-8-azabicyclo[3.2.1]octan-3-yl 1-(2,2-difluoroethyl)-1H-pyrrolo[2,3-b]pyridine-3-carboxylate 2,2,2-trifluoroacetate

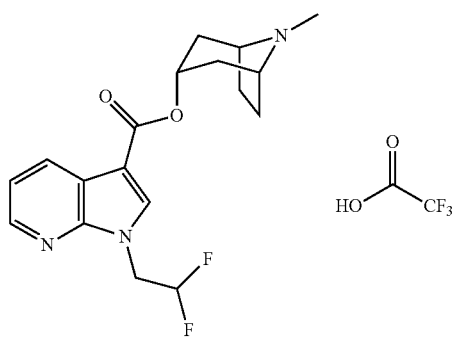 [SMILES: CN1C2CCC1CC(OC(=O)c1cn(CC(F)F)c3ncccc13)C2 ; O=C(O)C(F)(F)F]

Step 1: (1R,3R,5S)-8-methyl-8-azabicyclo[3.2.1]octan-3-yl 1H-pyrrolo[2,3-b]pyridine-3-carboxylate 2,2,2-trifluoroacetate Oxalyl dichloride (318 µl, 3.70 mmol) was added to a solution of 1H-pyrrolo[2,3-b]pyridine-3-carboxylic acid (500 mg, 3.08 mmol) and a drop of DMF in DMC (Volume: 10.0 ml) at 0° C. After 1 h, the mixture was allowed to warm to RT and concentrated under reduced pressure. The residue was redissolved in DCM (Volume: 10.0 ml). (1R,3R,5S)-8-methyl-8-azabicyclo[3.2.1]octan-3-ol (653 mg, 4.63 mmol) and N,N-diisopropylethylamine (1343 µl, 7.71 mmol) were added to the suspension. After being stirred at RT for 14 h, the mixture was diluted with DMF, filtered and purified by HPLC to afford the title compound as a colorless oil.

Step 2: Synthesis of (1R,3R,5S)-8-methyl-8-azabicyclo[3.2.1]octan-3-yl 1-(2,2-difluoroethyl)-1H-pyrrolo[2,3-b]pyridine-3-carboxylate 2,2,2-trifluoroacetate 2-Bromo-1,1-difluoroethane (54.4 mg, 0.376 mmol) was added in one portion to a suspension of (1R,3R,5S)-8-methyl-8-azabicyclo[3.2.1]octan-3-yl 1H-pyrrolo[2,3-b]pyridine-3-carboxylate 2,2,2-trifluoroacetate (50 mg, 0.125 mmol) and $K_2CO_3$ (87 mg, 0.626 mmol) in DMF (Volume: 626 µl) at RT. The mixture was heated at 70° C. for 14 h, cooled to RT, diluted with DMF, filtered, and purified by HPLC to afford the title compound as a colorless oil. MS (ESI, pos. ion) m/z: 350.2 (M+1).

Example 2

Synthesis of N-((1R,3R,5S)-9-methyl-9-azabicyclo[3.3.1]nonan-3-yl)-1-(methylsulfonyl)-1H-indazole-3-carboxamide 2,2,2-trifluoroacetic acid

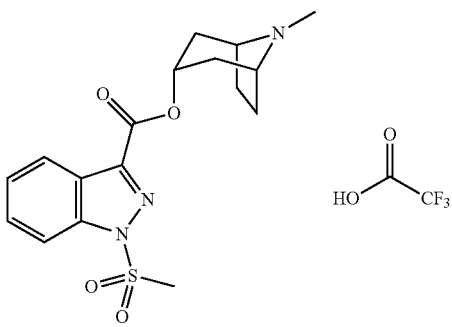 [SMILES: CN1C2CCC1CC(OC(=O)c1nn(S(C)(=O)=O)c3ccccc13)C2 ; O=C(O)C(F)(F)F]

A mixture of 1-(methylsulfonyl)-1H-indazole-3-carboxylic acid (60 mg, 0.250 mmol; see Reference 9 for the synthesis), di-tert-butyl dicarbonate (75 µl, 0.325 mmol), (1R,3R,5S)-9-methyl-9-azabicyclo[3.3.1]nonan-3-ol (38.8 mg, 0.250 mmol), and DMAP (3.05 mg, 0.025 mmol) in THF (1249 µl) was heated to 80° C. overnight. Concentration and HPLC purification (after dilution with DMF and filtration) gave the title compound as a clear oil. MS (ESI, pos. ion) m/z: 378.2 (M+1).

Example 3

Synthesis of quinuclidin-4-yl 5-fluoro-1-(methylsulfonyl)-1H-indole-3-carboxylate 2,2,2-trifluoroacetic acid

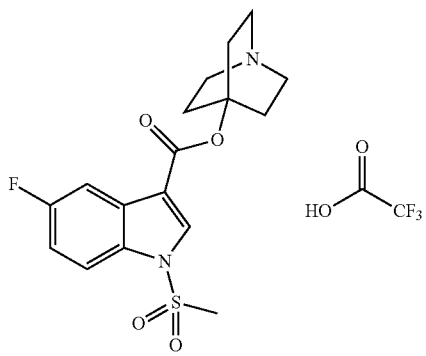 [SMILES: CS(=O)(=O)n1cc(C(=O)OC23CCN(CC2)CC3)c2cc(F)ccc21 ; O=C(O)C(F)(F)F]

In a vial containing 5-fluoro-1-(methylsulfonyl)-1H-indole-3-carboxylic acid (20 mg, 0.078 mmol; see Reference 10 for the synthesis) and trifluoroacetic anhydride (10.98 µl, 0.078 mmol) in toluene (259 µl) was added TFA (64.8 µl). After 30 min, quinuclidin-4-ol (8.24 mg, 0.065 mmol) was added and the mixture was stirred at RT overnight. Direct HPLC purification (after dilution with DMF and filtration) gave the title compound as a clear film. MS (ESI, pos. ion) m/z: 367.2 (M+1).

Compound 181 in Table 1 was synthesized as described in Example 3 above.

Example 4

Synthesis of (1R,3R,5S)-8-methyl-8-azabicyclo[3.2.1]octan-3-yl 2-chloro-1-(2,2-difluoroethyl)-1H-indole-3-carboxylate 2,2,2-trifluoroacetate

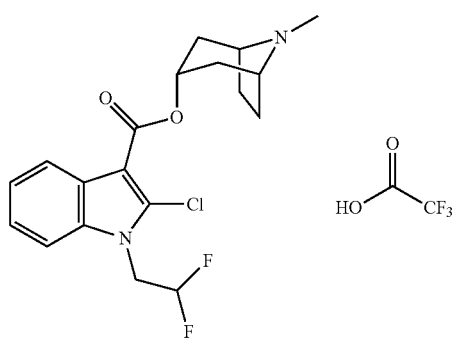 [SMILES: CN1C2CCC1CC(OC(=O)c1c(Cl)n(CC(F)F)c3ccccc13)C2 ; O=C(O)C(F)(F)F]

Step 1: (1R,3R,5S)-8-methyl-8-azabicyclo[3.2.1]octan-3-yl 2-chloro-1H-indole-3-carboxylate 2,2,2-trifluoroacetate The title compound was synthesized by utilizing similar conditions as described in Example 3 above.

Step 2: (1R,3R,5S)-8-methyl-8-azabicyclo[3.2.1]octan-3-yl 2-chloro-1-(2,2-difluoroethyl)-1H-indole-3-carboxylate 2,2,2-trifluoroacetate A solution of (1R,3R,5S)-8-methyl-8-azabicyclo[3.2.1]octan-3-yl 2-chloro-1H-indole-3-carboxylate 2,2,2-trifluoroacetate (23 mg, 0.053 mmol), 2-bromo-1,1-difluoroethane (23.11 mg, 0.159 mmol) and $K_2CO_3$ (36.7 mg, 0.266 mmol) in DMF (266 µl) was heated at 80° C. for 14 h. After cooling to RT, the mixture was diluted with DMF, filtered and purified by HPLC to afford the title compound as a white solid. MS (ESI, pos. ion) m/z: 383.2 (M+1)

Compounds in Table 1 above 1, 2, 15, 27, 40, 56, 83, 88, 95, 96, and 97 were synthesized as described in Example 4 above. Step 1 of compound 41 was carried out as in Example 1, followed by Step 2 of Example 4.

Example 5

Synthesis of (1R,3R,5S)-8-azabicyclo[3.2.1]octan-3-yl 1-(2,2,2-trifluoroethyl)-1H-indole-3-carboxylate 2,2,2-trifluoroacetate

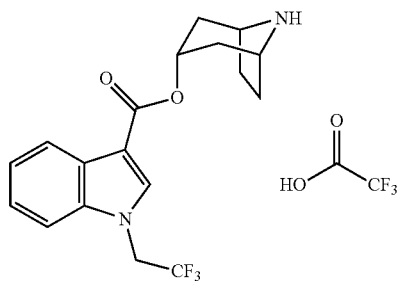 [SMILES: O=C(OC1CC2CCC(C1)N2)c1cn(CC(F)(F)F)c2ccccc12 ; O=C(O)C(F)(F)F]

Steps 1 and 2: (1R,3R,5S)-8-((Benzyloxy)carbonyl)-8-azabicyclo[3.2.1]octan-3-yl 1-(2,2,2-trifluoroethyl)-1H-indole-3-carboxylate (1R,3R,5S)-8-((Benzyloxy)carbonyl)-8-azabicyclo[3.2.1]octan-3-yl 1-(2,2,2-trifluoroethyl)-1H-indole-3-carboxylate (prepared as described in Example 1 above) was convered to the title compound by utilizing a similar procedure as described in Example 4 above.

Step 3: (1R,3R,5S)-8-Azabicyclo[3.2.1]octan-3-yl 1-(2,2,2-trifluoroethyl)-1H-indole-3-carboxylate 2,2,2-trifluoroacetate A suspension of (1R,3R,5S)-8-((benzyloxy)carbonyl)-8-azabicyclo[3.2.1]octan-3-yl 1-(2,2,2-trifluoroethyl)-1H-indole-3-carboxylate (47.7 mg, 0.098 mmol) and palladium on carbon (10 wt %, 5 mg, 4.70 µmol) was stirred under 1 atm $H_2$ atmosphere in EtOH/EtOAc (1:1, Volume: 980 µl) at RT. After 2 h, the mixture was filtered through a pad of Celite and the filtrate was concentrated, diluted with DMF and purified by HPLC to afford the title compound as a colorless oil. MS (ESI, pos. ion) m/z: 353.2 (M+1)

Utilizing a similar procedure as described above compound 45 in Table 1 above was prepared.

Example 6

Synthesis of (1R,3R,5S)-8-methyl-8-azabicyclo[3.2.1]octan-3-yl 2-chloro-1-(methylsulfonyl)-1H-indole-3-carboxylate 2,2,2-trifluoroacetate

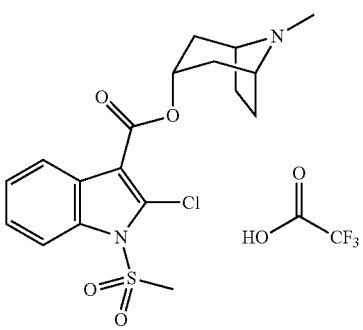 [SMILES: CN1C2CCC1CC(OC(=O)c1c(Cl)n(S(C)(=O)=O)c3ccccc13)C2 ; O=C(O)C(F)(F)F]

Step 1: (1R,3R,5S)-8-Methyl-8-azabicyclo[3.2.1]octan-3-yl 2-chloro-1H-indole-3-carboxylate 2,2,2-trifluoroacetate The title compound was synthesized by similar conditions as described in Example 3 above.

Step 2: (1R,3R,5S)-8-Methyl-8-azabicyclo[3.2.1]octan-3-yl 2-chloro-1-(methylsulfonyl)-1H-indole-3-carboxylate 2,2,2-trifluoroacetate Sodium bis(trimethylsilyl)amide (1.0 M THF, 150 μl, 0.150 mmol) was added to a solution of (1R,3R,5S)-8-methyl-8-azabicyclo[3.2.1]octan-3-yl 2-chloro-1H-indole-3-carboxylate 2,2,2-trifluoroacetate (28.3 mg, 0.065 mmol) in THF (327 μl) at 0° C. After 5 min, methanesulfonyl chloride (6.58 μl, 0.085 mmol) was added and the mixture was stirred at RT for 1 h. The mixture was diluted with DMF, filtered and purified by HPLC to afford the title compound as a colorless film. MS (ESI, pos. ion) m/z: 397.2 (M+1).

Utilizing a similar procedure as described above, compounds 3, 26, 34, 86, and 99 in Table 1 above were prepared.

Example 7

N-((1R,5S,7S)-9-methyl-3-oxa-9-azabicyclo[3.3.1]nonan-7-yl)-1-(1,1,1-trifluoro-2-methylpropan-2-yl)-1H-pyrrolo[2,3-b]pyridine-3-carboxamide 2,2,2-trifluoroacetate

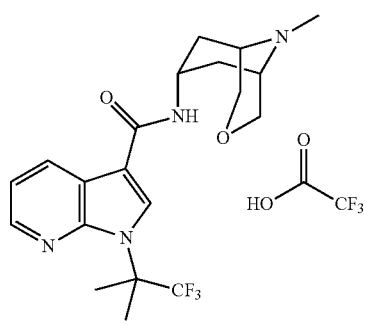

HATU (34.1 mg, 0.090 mmol) was added to a solution of 1-(1,1,1-trifluoro-2-methylpropan-2-yl)-1H-pyrrolo[2,3-b]pyridine-3-carboxylic acid (24.4 mg, 0.090 mmol; see Reference 8 for the synthesis), (1R,5S,7S)-9-methyl-3-oxa-9-azabicyclo[3.3.1]nonan-7-amine (14.00 mg, 0.090 mmol) and N,N-diisopropylethylamine (46.8 μl, 0.269 mmol) in DMF (Volume: 179 μl) at RT. After 20 min, the mixture was diluted with DMF, filtered and purified by HPLC to afford the title compound as a yellow film. MS (ESI, pos. ion) m/z: 411.3 (M+1).

Compounds 10, 36, 46, 69, 71, 92, 93, 94, 107, 111, 114, 117-123 in Table 1 above were synthesized by utilizing a similar procedure as described in Example 7 above using the carboxylic acid intermediate prepared by procedures indicated below:

Compound 69 (Reference 8); 71 (Reference 5); 92 (Reference 6); 94 (Reference 5); 107 (Reference 6); 10 (Reference 11); 36 (Reference 10); 46 (Reference 9); 93 (Reference 11); 111 (Reference 2 for the amine synthesis and Reference 11 for the carboxylic acid synthesis); 114 (Reference 2 for the amine synthesis and Reference 5 for the carboxylic acid synthesis); 117 (Reference 7); 118 (Reference 7); 119 (Reference 7); 120 (Reference 5); 121 (Reference 2 for the amine synthesis and Reference 6 for the carboxylic acid synthesis); 122 (Reference 2 for the amine synthesis and Reference 6 for the carboxylic acid synthesis); 123 (Reference 2 for the amine synthesis and Reference 7 for the carboxylic acid synthesis).

Example 8

Synthesis of 1-(2,2-difluoroethyl)-N-((1R,3R,5S)-8-methyl-8-azabicyclo[3.2.1]octan-3-yl)-1H-indazole-3-carboxamide 2,2,2-trifluoroacetate

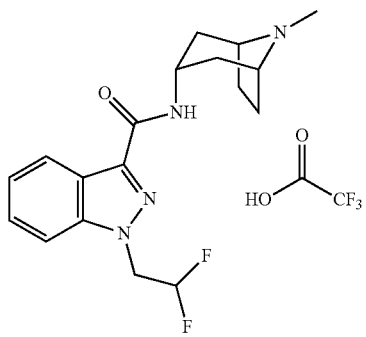

Step 1: N-((1R,3R,5S)-8-Methyl-8-azabicyclo[3.2.1]octan-3-yl)-1H-indazole-3-carboxamide 2,2,2-trifluoroacetate The title compound was synthesized by utilizing similar conditions as described in Example 7.

Step 2: 1-(2,2-Difluoroethyl)-N-((1R,3R,5S)-8-methyl-8-azabicyclo[3.2.1]octan-3-yl)-1H-indazole-3-carboxamide 2,2,2-trifluoroacetate Similar conditions as described in Example 4, Step 2 were utilized to afford the title compound as a colorless film. MS (ESI, pos. ion) m/z: 349.25 (M+1)

Following compounds in Table 1 above were synthesized by utilizing a similar procedure as described in Example 8 above: Compounds 7, 12, 20, 66, 75, and 98.

Example 9

Synthesis of N-((1R,3R,5S)-8-methyl-8-azabicyclo[3.2.1]octan-3-yl)-1-(methylsulfonyl)-1H-indazole-3-carboxamide 2,2,2-trifluoroacetate

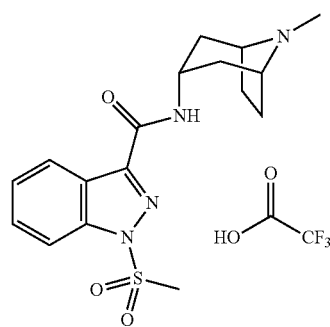

Step 1: N-((1R,3R,5S)-8-Methyl-8-azabicyclo[3.2.1]octan-3-yl)-1H-indazole-3-carboxamide 2,2,2-trifluoroacetate The title compound was synthesized by utilizing similar conditions as described in Example 7 above.

Step 2: N-((1R,3R,5S)-8-Methyl-8-azabicyclo[3.2.1]octan-3-yl)-1-(methylsulfonyl)-1H-indazole-3-carboxamide 2,2,2-trifluoroacetate Similar conditions as described in Example 6, Step 2 were utilized to afford the title compound as a colorless film. MS (ESI, pos. ion) m/z: 363.2 (M+1)

Following compounds in Table 1 above were synthesized by utilizing a similar procedure as described in Example 9 above: Compounds 18, 74, 101, and 110 (azabicyclic intermediate prepared by Reference 2).

Example 10

Synthesis of (1R,3R,5S)-9-methyl-9-azabicyclo[3.3.1]nonan-3-yl 1-(2,2-difluoroethyl)-1H-pyrrolo[2,3-b]pyridine-3-carboxylate 2,2,2-trifluoroacetate

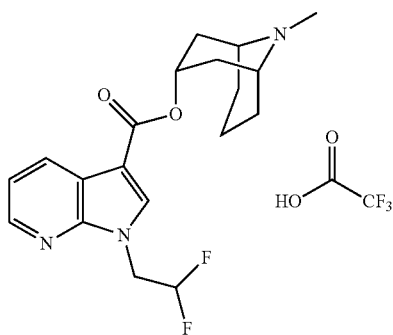 [SMILES: CN1C2CCCC1CC(OC(=O)c1cn(CC(F)F)c3ncccc13)C2 ; O=C(O)C(F)(F)F]

Step 1: Methyl 1-(2,2-difluoroethyl)-1H-pyrrolo[2,3-b]pyridine-3-carboxylate 2-Bromo-1,1-difluoroethane (677 µl, 8.51 mmol) was added to a suspension of methyl 1H-pyrrolo[2,3-b]pyridine-3-carboxylate (500 mg, 2.84 mmol) and $K_2CO_3$ (1177 mg, 8.51 mmol) in DMF (2838 µl) at RT. The mixture was heated at 70° C. for 14 h and purified by column chromatography ($SiO_2$; DCM/MeOH) to afford the title compound as a white solid.

Step 2: 1-(2,2-Difluoroethyl)-1H-pyrrolo[2,3-b]pyridine-3-carboxylic acid

The title compound was synthesized by utilizing similar conditions as described in Reference 5, Step 2.

Step 3: (1R,3R,5S)-9-Methyl-9-azabicyclo[3.3.1]nonan-3-yl 1-(2,2-difluoroethyl)-1H-pyrrolo[2,3-b]pyridine-3-carboxylate 2,2,2-trifluoroacetate CDI (14.34 mg, 0.088 mmol) was added to a solution of 1-(2,2-difluoroethyl)-1H-pyrrolo[2,3-b]pyridine-3-carboxylic acid (20 mg, 0.088 mmol) in DMF (Volume: 442 µl) at RT and the resulting mixture was heated at 60° C. for 1 h. In a separate vial, sodium hydride (4.24 mg, 0.106 mmol) was added to a solution of (1R,3R,5S)-9-methyl-9-azabicyclo[3.3.1]nonan-3-ol (16.47 mg, 0.106 mmol) in DMF (Volume: 442 µl) at RT and the resulting mixture was heated at 60° C. for 1 h. The resulting alkoxide solution was added to the imidazolide solution and the mixture was heated at 70° C. for 2 h. The mixture was diluted with DMF, filtered and purified by HPLC to afford the title compound as a colorless film. MS (ESI, pos. ion) m/z: 364.3 (M+1).

Compounds 16, 57, 91, 103, 17, 60, 116 and 89 in Table 1 above were synthesized by utilizing a similar procedure as described in Example 10 above unless indicated otherwise below:

Compound 16 (Similar conditions as described in Example 2 above were utilized for Step 3);
Compound 57 (Similar conditions as described in Example 2 above were utilized for Step 3);
Compound 91 (Similar conditions as described in Example 3 above were utilized for Step 3);
Compound 103 (Similar conditions as described in Example 3 above were utilized for Step 3);
Compound 17 (Similar conditions as described in Example 2 above were utilized for Step 3);
Compound 60 (Similar conditions as described in Example 3 above were utilized for Step 3); and
Compound 89 (Similar conditions as described in Example 3 above were utilized for Step 3).

Example 11

Synthesis of 1-(2,2-difluoroethyl)-N-((1R,5S,7S)-9-methyl-3-oxa-9-azabicyclo[3.3.1]nonan-7-yl)-1H-pyrrolo[2,3-b]pyridine-3-carboxamide 2,2,2-trifluoroacetate

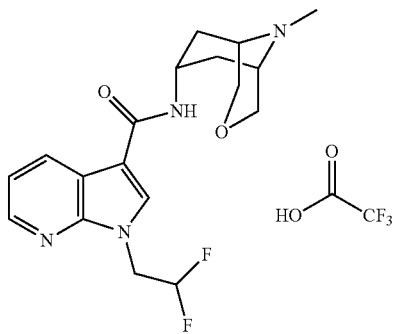 [SMILES: CN1C2COCC1CC(NC(=O)c1cn(CC(F)F)c3ncccc13)C2 ; O=C(O)C(F)(F)F]

Step 1 and 2: 1-(2,2-Difluoroethyl)-1H-pyrrolo[2,3-b]pyridine-3-carboxylic acid The title compound was synthesized by utilizing similar conditions as described in Example 10, Steps 1 and 2.

Step 3: 1-(2,2-Difluoroethyl)-N-((1R,5S,7S)-9-methyl-3-oxa-9-azabicyclo[3.3.1]nonan-7-yl)-1H-pyrrolo[2,3-b]pyridine-3-carboxamide 2,2,2-trifluoroacetate Similar conditions as described in Example 7 were utilized to afford the title compound as a colorless oil. MS (ESI, pos. ion) m/z: 365.3 (M+1)

Following compounds in Table 1 above were synthesized by utilizing a similar procedure as described in Example 11: Compounds 5, 9, 21, 22, 52, 53, 63, 67, 68, 70, 76, 77, 79, 80, 81, 102, 104 (Reference 3 for amine synthesis), 108, 109 (Reference 2 for amine synthesis), 112, 113, 126 and 127 (Reference 2 for amine synthesis).

Example 12

Synthesis of (1R,5S,7S)-3-oxa-9-azabicyclo[3.3.1]nonan-7-yl 1-(2,2-difluoroethyl)-1H-pyrrolo[2,3-b]pyridine-3-carboxylate 2,2,2-trifluoroacetate

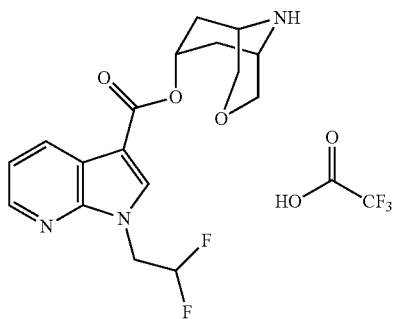 [SMILES: O=C(OC1CC2COCC(C1)N2)c1cn(CC(F)F)c2ncccc12 ; O=C(O)C(F)(F)F]

Step 1: (1R,5S,7S)-tert-Butyl 7-((1-(2,2-difluoroethyl)-1H-pyrrolo[2,3-b]pyridine-3-carbonyl)oxy)-3-oxa-9-azabicyclo[3.3.1]nonane-9-carboxylate The title compound was synthesized by utilizing a similar procedure as described in Example 10 above.

Step 2: (1R,5S,7S)-3-Oxa-9-azabicyclo[3.3.1]nonan-7-yl 1-(2,2-difluoroethyl)-1H-pyrrolo[2,3-b]pyridine-3-carboxylate 2,2,2-trifluoroacetate TFA (325 μl) was added to a solution of (1R,5S,7S)-tert-butyl 7-((1-(2,2-difluoroethyl)-1H-pyrrolo[2,3-b]pyridine-3-carbonyl)oxy)-3-oxa-9-azabicyclo[3.3.1]nonane-9-carboxylate (58.6 mg, 0.130 mmol) in DCM (325 μl) at RT. After 10 min, the reaction mixture was diluted with DMF, filtered and purified by HPLC to afford the title compound as a white solid. MS (ESI, pos. ion) m/z: 352.2 (M+1)

Example 13

Synthesis of (1R,5S,7S)-3-Oxa-9-azabicyclo[3.3.1]nonan-7-yl 1-(2,2-difluoroethyl)-5-fluoro-1H-indole-3-carboxylate 2,2,2-trifluoroacetic acid

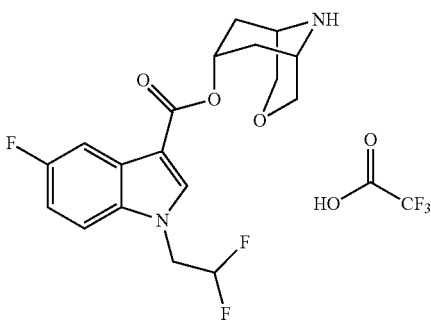 [SMILES: O=C(OC1CC2COCC(C1)N2)c1cn(CC(F)F)c2ccc(F)cc12 ; O=C(O)C(F)(F)F]

Steps 1 and 2: 1-(2,2-Difluoroethyl)-5-fluoro-1H-indole-3-carboxylic acid

The title compound was synthesized by utilizing similar conditions as described in Example 10, Step 1 and 2.

Step 3: (1R,5S,7S)-3-Oxa-9-azabicyclo[3.3.1]nonan-7-yl 1-(2,2-difluoroethyl)-5-fluoro-1H-indole-3-carboxylate 2,2,2-trifluoroacetic acid In a vial containing 1-(2,2-difluoroethyl)-5-fluoro-1H-indole-3-carboxylic acid (100 mg, 0.411 mmol) and trifluoroacetic anhydride (58.1 μl, 0.411 mmol) in toluene (1371 μl) was added TFA (343 μl). The reaction mixture was stirred at RT for 30 min then (1R,5S,7S)-tert-butyl 7-hydroxy-3-oxa-9-azabicyclo[3.3.1]nonane-9-carboxylate (83 mg, 0.343 mmol; see Reference 1 for the synthesis) was added and stirring continued for 2 h. Direct HPLC purification (after dilution with DMF and filtration) gave the title compound as a white solid. MS (ESI, pos. ion) m/z: 369.2 (M+1).

Following compounds in Table 1 above were synthesized by utilizing a similar procedure as described in Example 13 above Compounds 11, 23, 25, 54, 59, and 128 using acid synthesized by the procedure indicated below:

Example 54 (See Reference 11 for the carboxylic acid synthesis)

Example 11 (See Reference 5 for the carboxylic acid synthesis)

Example 23 (See Reference 6 for the carboxylic acid synthesis)

Example 25 (See Reference 6 for the carboxylic acid synthesis)

Example 128 (See Reference 7 for the carboxylic acid synthesis).

Example 14

Synthesis of (1R,5S,7S)-9-methyl-3-oxa-9-azabicyclo[3.3.1]nonan-7-yl 1-(2,2-difluoroethyl)-1H-pyrrolo[2,3-b]pyridine-3-carboxylate 2,2,2-trifluoroacetate

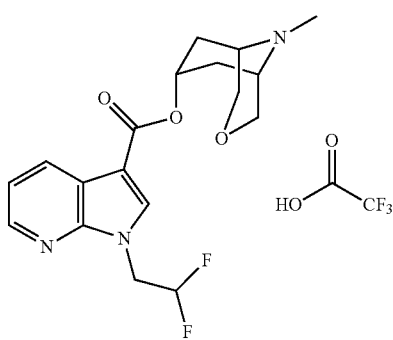 [SMILES: CN1C2COCC1CC(OC(=O)c1cn(CC(F)F)c3ncccc13)C2 ; O=C(O)C(F)(F)F]

Steps 1 and 2: (1R,5S,7S)-3-Oxa-9-azabicyclo[3.3.1]nonan-7-yl 1-(2,2-difluoroethyl)-1H-pyrrolo[2,3-b]pyridine-3-carboxylate The title compound was synthesized by utilizing similar conditions as described in Example 12 above.

Step 3: (1R,5S,7S)-9-Methyl-3-oxa-9-azabicyclo[3.3.1]nonan-7-yl 1-(2,2-difluoroethyl)-1H-pyrrolo[2,3-b]pyridine-3-carboxylate 2,2,2-trifluoroacetate Sodium triacetoxyborohydride (11.44 mg, 0.054 mmol) was added to a solution of (1R,5S,7S)-3-oxa-9-azabicyclo[3.3.1]nonan-7-yl 1-(2,2-difluoroethyl)-1H-pyrrolo[2,3-b]pyridine-3-carboxylate (15.81 mg, 0.045 mmol) and formaldehyde (4.91 mg, 0.054 mmol) in DCM (225 µl) at RT. After 15 min, the reaction mixture was diluted with DMF, filtered and purified by HPLC to afford the title compound as a colorless film. MS (ESI, pos. ion) m/z: 366.2 (M+1).

Compounds 32, 49, and 58 in Table 1 above were synthesized by utilizing a similar procedure as described in Example 14 above.

Example 15

Synthesis of (1R,5S,7S)-9-(2-fluoroethyl)-3-oxa-9-azabicyclo[3.3.1]nonan-7-yl 1-(2,2-difluoroethyl)-5-fluoro-1H-indole-3-carboxylate, 2,2,2-trifluoroacetic acid

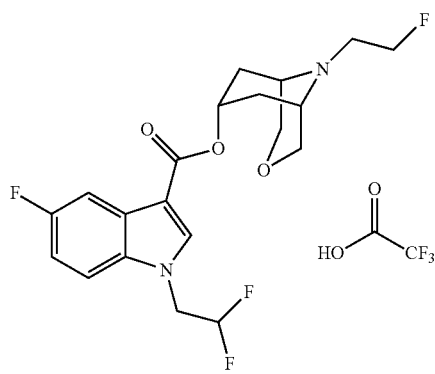 [SMILES: O=C(OC1CC2COCC(C1)N2CCF)c1cn(CC(F)F)c2ccc(F)cc12 ; O=C(O)C(F)(F)F]

Step 1: (1R,5S,7S)-3-Oxa-9-azabicyclo[3.3.1]nonan-7-yl 1-(2,2-difluoroethyl)-5-fluoro-1H-indole-3-carboxylate 2,2,2-trifluoroacetic acid The title compound was synthesized by utilizing similar procedure as described in Example 13 above.

Step 2: (1R,5S,7S)-9-(2-Fluoroethyl)-3-oxa-9-azabicyclo[3.3.1]nonan-7-yl 1-(2,2-difluoroethyl)-5-fluoro-1H-indole-3-carboxylate, 2,2,2-trifluoroacetic acid A solution of (1R,5S,7S)-3-oxa-9-azabicyclo[3.3.1]nonan-7-yl 1-(2,2-difluoroethyl)-5-fluoro-1H-indole-3-carboxylate 2,2,2-trifluoroacetate (20 mg, 0.041 mmol), triethylamine (28.9 µl, 0.207 mmol), and 1-bromo-2-fluoroethane (9.29 µl, 0.124 mmol) in MeCN (415 µl) was heated to 100° C. for 2 days. HPLC purification (after dilution with DMF and filtration) gave the title compound as a white solid. MS (ESI, pos. ion) m/z: 415.2 (M+1)

Compound 50 in Table 1 above was synthesized by utilizing a similar procedure as described in Example 15 above.

Example 16

Synthesis of N-((1R,5S,7S)-3-oxa-9-azabicyclo[3.3.1]nonan-7-yl)-5-fluoro-1-(2,2,2-trifluoroethyl)-1H-indole-3-carboxamide 2,2,2-trifluoroacetic acid

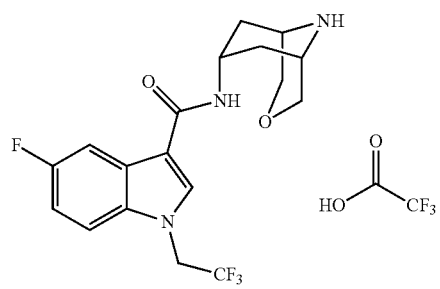 [SMILES: O=C(NC1CC2COCC(C1)N2)c1cn(CC(F)(F)F)c2ccc(F)cc12 ; O=C(O)C(F)(F)F]

Step 1: (1R,5S,7S)-tert-Butyl 7-(5-fluoro-1-(2,2,2-trifluoroethyl)-1H-indole-3-carboxamido)-3-oxa-9-azabicyclo[3.3.1]nonane-9-carboxylate The title compound was synthesized by a similar procedure as described in Example 11 above.

Step 2: N-((1R,5S,7S)-3-Oxa-9-azabicyclo[3.3.1]nonan-7-yl)-5-fluoro-1-(2,2,2-trifluoroethyl)-1H-indole-3-carboxamide, 2,2,2-trifluoroacetic acid salt Similar conditions as described in Example 12, Step 2 were utilized to afford the title compound as a clear oil. MS (ESI, pos. ion) m/z: 386.2 (M+1).

Following compounds in Table 1 above were synthesized by utilizing a similar procedure as described in Example 16 above: Compounds 39, 38, 65 (Step 1 used from Example 8 above), 78 (see Reference 10 for carboxylic acid synthesis), 82, 105, and 185.

Example 17

Synthesis of N-((1R,5S,7S)-3-oxa-9-azabicyclo[3.3.1]nonan-7-yl)-5-fluoro-1-(2,2,2-trifluoroethyl)-1H-indole-3-carboxamide 2,2,2-trifluoroacetate

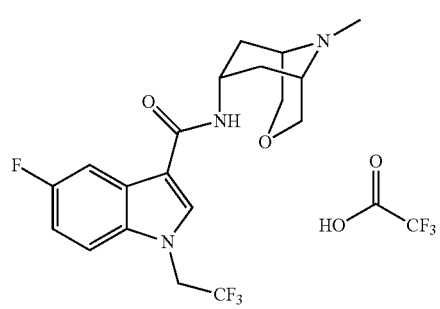 [SMILES: CN1C2COCC1CC(NC(=O)c1cn(CC(F)(F)F)c3ccc(F)cc13)C2 ; O=C(O)C(F)(F)F]

Step 1 and 2: N-((1R,5S,7S)-3-Oxa-9-azabicyclo [3.3.1]nonan-7-yl)-5-fluoro-1-(2,2,2-trifluoroethyl)-1H-indole-3-carboxamide 2,2,2-trifluoroacetate The title compound was synthesized by utilizing similar conditions as described in Example 16 above.

Step 3: N-((1R,5S,7S)-3-Oxa-9-azabicyclo[3.3.1] nonan-7-yl)-5-fluoro-1-(2,2,2-trifluoroethyl)-1H-indole-3-carboxamide 2,2,2-trifluoroacetate Similar conditions as described in Example 14, Step 3 were utilized to afford the title compound as a clear film. MS (ESI, pos. ion) m/z: 400.25 (M+1)

Compounds 129 and 186 in Table 1 above was synthesized by utilizing a similar procedure as described in Example 17 above. Carboxylic acid was synthesized using method in Reference 6 above).

Example 18

Synthesis of 5-fluoro-N-((1R,5S,7S)-9-methyl-$d_3$-3-oxa-9-azabicyclo[3.3.1]nonan-7-yl)-1-(2,2,2-trifluoroethyl)-1H-pyrrolo[2,3-b]pyridine-3-carboxamide 2,2,2-trifluoroacetate

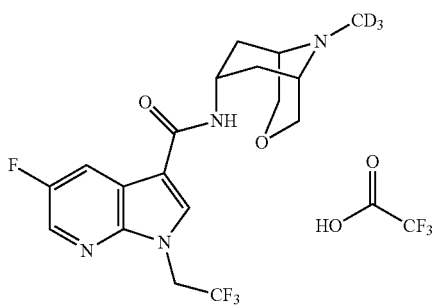 [SMILES: [2H]C([2H])([2H])N1C2COCC1CC(NC(=O)c1cn(CC(F)(F)F)c3ncc(F)cc13)C2 ; O=C(O)C(F)(F)F]

Steps 1 and 2: N-((1R,5S,7S)-3-Oxa-9-azabicyclo [3.3.1]nonan-7-yl)-5-fluoro-1-(2,2,2-trifluoroethyl)-1H-pyrrolo[2,3-b]pyridine-3-carboxamide 2,2,2-trifluoroacetate The title compound was synthesized by utilizing similar conditions as described in Example 16 above.

Step 3: 5-Fluoro-N-((1R,5S,7S)-9-methyl-$d_3$-3-oxa-9-azabicyclo[3.3.1]nonan-7-yl)-1-(2,2,2-trifluoroethyl)-1H-pyrrolo[2,3-b]pyridine-3-carboxamide 2,2,2-trifluoroacetate A mixture of N-((1R,5S,7S)-3-oxa-9-azabicyclo[3.3.1] nonan-7-yl)-5-fluoro-1-(2,2,2-trifluoroethyl)-1H-pyrrolo[2,3-b]pyridine-3-carboxamide 2,2,2-trifluoroacetate (16.2 mg, 0.032 mmol), methyl-$d_3$-4-methylbenzenesulfonate (12.25 mg, 0.065 mmol) and $K_2CO_3$ (13.42 mg, 0.097 mmol) in MeCN (324 µl) was heated at 80° C. for 10 min and purified by HPLC (after dilution with DMF and filtration). Neutralization with $K_2CO_3$ and prep-TLC (DCM/MeOH) afforded the title compound as a colorless film. MS (ESI, pos. ion) m/z: 404.2 (M+1).

Compound 130 in Table 1 above were synthesized by utilizing a similar procedure as described in Example 18 above.

Example 19

Synthesis of (1R,3R,5S)-8-methyl-8-azabicyclo [3.2.1]octan-3-yl 3,4-dihydro-2H-[1,3]oxazino[3,2-a]indole-10-carboxylate 2,2,2-trifluoroacetate

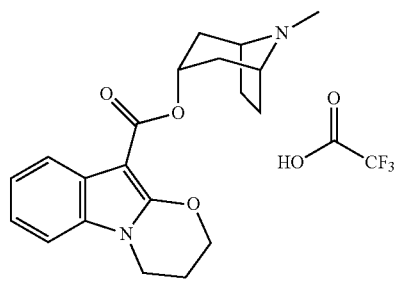 [SMILES: CN1C2CCC1CC(OC(=O)c1c3n(c4ccccc14)CCCO3)C2 ; O=C(O)C(F)(F)F]

Step 1: (1R,3R,5S)-8-Methyl-8-azabicyclo[3.2.1] octan-3-yl 2-(3-bromopropoxy)-1H-indole-3-carboxylate NCS (35.2 mg, 0.264 mmol) was added to a suspension of (1R,3R,5S)-8-methyl-8-azabicyclo[3.2.1]octan-3-yl 1H-indole-3-carboxylate (50 mg, 0.176 mmol) and 4A MS (100 mg) in chloroform (879 µl) at RT. After 30 min, 3-bromopropan-1-ol (48.9 mg, 0.352 mmol) was added to the solution. After being stirred at RT for 14 h, the reaction mixture was filtered through a pad of Celite. The filtrate was washed with brine, dried over anhydrous $Na_2SO_4$, filtered and concentrated under reduced pressure to afford the title compound, which was used without further purification.

Step 2: (1R,3R,5S)-8-Methyl-8-azabicyclo[3.2.1] octan-3-yl 3,4-dihydro-2H-[1,3]oxazino[3,2-a]indole-10-carboxylate 2,2,2-trifluoroacetate (1R,3R,5S)-8-Methyl-8-azabicyclo[3.2.1]octan-3-yl 2-(3-bromopropoxy)-1H-indole-3-carboxylate (74.2 mg, 0.176 mmol) and $K_2CO_3$ (73.0 mg, 0.528 mmol) were suspended in acetone (1760 µl) at RT. After being stirred for 24 h, the reaction mixture was diluted with DMF, filtered and purified by HPLC to afford the title compound as colorless film. MS (ESI, pos. ion) m/z: 341.3 (M+1)

Compounds 28 and 84 in Table 1 above were synthesized by utilizing a similar procedure as described in Example 19 above.

Example 20

Synthesis of (1R,5S,7S)-9-methyl-3-oxa-9-azabicyclo[3.3.1]nonan-7-yl 1-(2-fluoroethyl)-1H-indole-3-carboxylate 2,2,2-trifluoroacetic acid

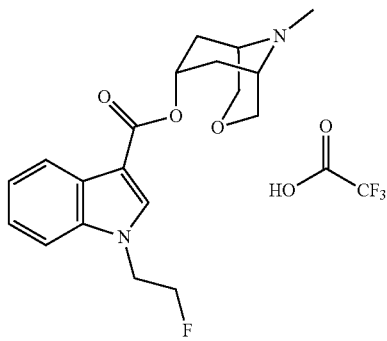 [SMILES: CN1C2COCC1CC(OC(=O)c1cn(CCF)c3ccccc13)C2 ; O=C(O)C(F)(F)F]

Steps 1, 2 and 3: (1R,5S,7S)-9-Methyl-3-oxa-9-azabicyclo[3.3.1]nonan-7-yl 1H-indole-3-carboxylate The title compound was synthesized by utilizing a similar procedure as described in Example 14 above. Similar conditions as described in Example 1 above were utilized for Step 1.

Step 4: (1R,5S,7S)-9-Methyl-3-oxa-9-azabicyclo[3.3.1]nonan-7-yl 1-(2-fluoroethyl)-1H-indole-3-carboxylate 2,2,2-trifluoroacetic acid Sodium hydride (11.98 mg, 0.300 mmol, 60% dispersion in mineral oil) was added to a solution of (1R,5S,7S)-9-methyl-3-oxa-9-azabicyclo[3.3.1]nonan-7-yl 1H-indole-3-carboxylate (60 mg, 0.200 mmol) in DMF (600 µl) at RT. After 15 min, 1-bromo-2-fluoroethane (22.38 µl, 0.300 mmol) was added and the reaction was stirred for a further 1 h. Direct HPLC purification (after dilution with DMF and filtration) gave the title compound as a clear oil. MS (ESI, pos. ion) m/z: 347.3 (M+1).

Example 21

Synthesis of (1R,5S,7S)-9-methyl-3-oxa-9-azabicyclo[3.3.1]nonan-7-yl 1-(methylsulfonyl)-1H-indole-3-carboxylate 2,2,2-trifluoroacetic acid

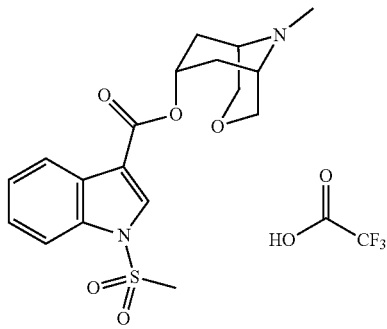 [SMILES: CN1C2COCC1CC(OC(=O)c1cn(S(C)(=O)=O)c3ccccc13)C2 ; O=C(O)C(F)(F)F]

Steps 1, 2 and 3: (1R,5S,7S)-9-Methyl-3-oxa-9-azabicyclo[3.3.1]nonan-7-yl 1H-indole-3-carboxylate 2,2,2-trifluoroacetate The title compound was synthesized by utilizing a similar procedure as described in Example 14 above. Similar conditions as described in Example 1 above were utilized for Step 1.

Step 4: (1R,5S,7S)-9-Methyl-3-oxa-9-azabicyclo[3.3.1]nonan-7-yl 1-(methylsulfonyl)-1H-indole-3-carboxylate 2,2,2-trifluoroacetic acid Similar conditions as described in Example 6, Step 2 were utilized to afford the title compound as a colorless oil. MS (ESI, pos. ion) m/z: 379.15 (M+1).

Example 22

Synthesis of (1R,5S,7S)-3-oxa-9-azabicyclo[3.3.1]nonan-7-yl 1-(isopropylsulfonyl)-1H-indole-3-carboxylate 2,2,2-trifluoroacetate

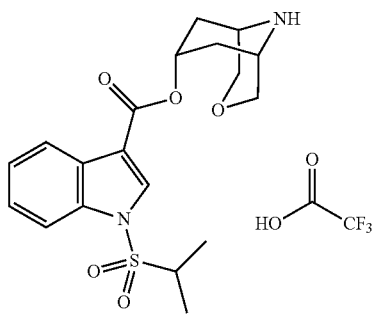 [SMILES: CC(C)S(=O)(=O)n1cc(C(=O)OC2CC3COCC(C2)N3)c2ccccc21 ; O=C(O)C(F)(F)F]

Step 1: (1R,5S,7S)-3-Oxa-9-azabicyclo[3.3.1]nonan-7-yl 1H-indole-3-carboxylate 2,2,2-trifluoroacetate The title compound was synthesized by utilizing similar conditions as described in Example 13, Step 3.

Step 2: (1R,5S,7S)-tert-Butyl 7-((1H-indole-3-carbonyl)oxy)-3-oxa-9-azabicyclo[3.3.1]-nonane-9-carboxylate Di-tert-butyl dicarbonate (168 µl, 0.731 mmol) was added to a solution of (1R,5S,7S)-3-oxa-9-azabicyclo[3.3.1]nonan-7-yl 1H-indole-3-carboxylate 2,2,2-trifluoroacetate (278.6 mg, 0.696 mmol) and N,N-diisopropylethylamine (182 µl, 1.044 mmol) in THF (Volume: 3479 µl) at RT. After 30 min, the mixture was concentrated under reduced pressure, taken up in EtOAc, washed with saturated aqueous NH$_4$Cl and brine. The combined organic layers were dried over anhydrous Na$_2$SO$_4$, filtered and concentrated under reduced pressure to afford the title compound as a white foam.

Step 3: (1R,5S,7S)-3-Oxa-9-azabicyclo[3.3.1]nonan-7-yl 1-(isopropylsulfonyl)-1H-indole-3-carboxylate 2,2,2-trifluoroacetate In a round-bottom flask containing (1R,5S,7S)-tert-butyl 7-((1H-indole-3-carbonyl)oxy)-3-oxa-9-azabicyclo[3.3.1]nonane-9-carboxylate (304 mg, 0.787 mmol) in THF (Volume: 7867 μl) in a water bath was added sodium hydride (60% in mineral oil, 47.2 mg, 1.180 mmol) and the white mixture was stirred for 20 min. Propane-2-sulfonyl chloride (177 μl, 1.573 mmol) was then added slowly and the solution became clear. After 30 min, HCl (4.0 M in dioxane, 9833 μl, 39.3 mmol) was then added and the mixture was heated to 50° C. for 30 min. Concentration and HPLC purification (after dilution with DMF and filtration) gave the title compound as a clear oil. MS (ESI, pos. ion) m/z: 393.2 (M+1).

Compounds 19, 132, 133, 134, and 135 in Table 1 above were synthesized by utilizing a similar procedure as described in Example 22 above.

Example 24

Synthesis of (1R,5S,7s)-3-oxa-9-azabicyclo[3.3.1]nonan-7-yl 1-(pyridazin-3-yl)-1H-indole-3-carboxylate, 2,2,2-trifluoroacetic acid salt

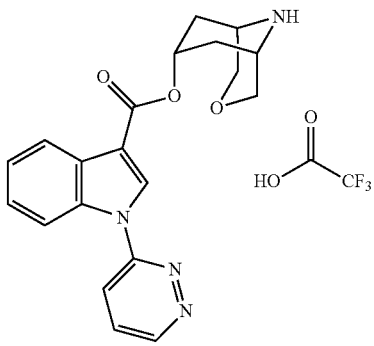

To a solution of (1R,5S,7s)-tert-butyl 7-((1H-indole-3-carbonyl)oxy)-3-oxa-9-azabicyclo[3.3.1]nonane-9-carboxylate (20 mg, 0.052 mmol) in NMP (104 μl) was added cesium carbonate (67.5 mg, 0.207 mmol) and 3-chloropyridazine (17.78 mg, 0.155 mmol). The mixture was heated at 110° C. for 3 h. Purification by HPLC gave the title compound as a tan solid. MS (ESI, pos. ion) m/z: 365.20 (M+1).

Example 25

Synthesis of (1R,5S,7s)-9-methyl-3-oxa-9-azabicyclo[3.3.1]nonan-7-yl 1-(6-fluoropyridazin-3-yl)-1H-indole-3-carboxylate

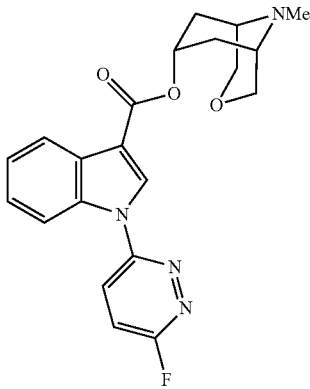 [SMILES: CN1C2COCC1CC(OC(=O)c1cn(-c3ccc(F)nn3)c3ccccc13)C2]

To a solution of (1R,5S,7s)-9-methyl-3-oxa-9-azabicyclo[3.3.1]nonan-7-yl 1H-indole-3-carboxylate (10 mg, 0.033 mmol) in THF (333 μl) was added NaH (1.332 mg, 0.033 mmol, 60% suspension in mineral oil) and 3,6-difluoropyridazine (5.80 mg, 0.050 mmol). The mixture was stirred at RT for 1 h then purified by ISCO (0-20% MeOH/DCM) to give the title compound as a white solid. MS (ESI, pos. ion) m/z: 397.20 (M+1).

Example 26

Synthesis of N-((1R,5S,7s)-9-methyl-3-oxa-9-azabicyclo[3.3.1]nonan-7-yl)-1-phenyl-1H-indole-3-carboxamide, 2,2,2-trifluoroacetic acid salt

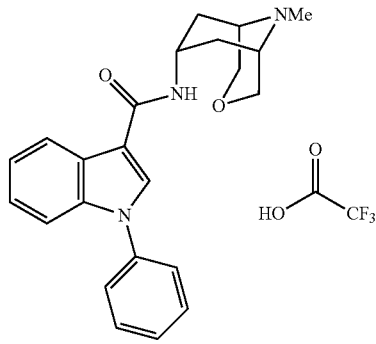 [SMILES: CN1C2COCC1CC(NC(=O)c1cn(-c3ccccc3)c3ccccc13)C2 ; O=C(O)C(F)(F)F]

A 5 mL screwtop vial containing 1-phenyl-1H-indole-3-carboxylic acid (20 mg, 0.084 mmol), HATU (32.1 mg, 0.084 mmol), and N-ethyl-N-isopropylpropan-2-amine (58.9 μl, 0.337 mmol) in DMF (421 μl) was stirred for 10 min then (1R,5S,7s)-9-methyl-3-oxa-9-azabicyclo[3.3.1]nonan-7-amine 2,2,2-trifluoroacetate (22.78 mg, 0.084 mmol) was added and stirred for 1 h. Direct HPLC purification afforded the title compound as a white foam. MS (ESI, pos. ion) m/z: 376.25 (M+1).

The following compounds were prepared by a similar procedure, either with commercially available carboxylic acids or those synthesized according to reference compound procedures:

1-(1-methyl-1H-imidazol-5-yl)-N-((1R,5S,7s)-9-methyl-3-oxa-9-azabicyclo[3.3.1]nonan-7-yl)-1H-indole-3-carboxamide, 2,2,2-trifluoroacetic acid salt; 1-(cyanomethyl)-N-((1R,5S,7s)-9-methyl-3-oxa-9-azabicyclo[3.3.1]nonan-7-yl)-1H-indole-3-carboxamide, 2,2,2-trifluoroacetic acid salt; N-((1R,5S,7s)-9-methyl-3-oxa-9-azabicyclo[3.3.1]nonan-7-yl)-1-(thiazol-2-yl)-1H-pyrrolo[2,3-b]pyridine-3-carboxamide, 2,2,2-trifluoroacetic acid salt; N-((1R,5S,7s)-9-methyl-3-oxa-9-azabicyclo[3.3.1]nonan-7-yl)-1-(thiazol-4-yl)-1H-pyrrolo[2,3-b]pyridine-3-carboxamide, 2,2,2-trifluoroacetic acid salt; N-((1R,5S,7s)-9-methyl-3-oxa-9-azabicyclo[3.3.1]nonan-7-yl)-1-(thiazol-5-yl)-1H-pyrrolo[2,3-b]pyridine-3-carboxamide, 2,2,2-trifluoroacetic acid salt; 5-fluoro-N-((1R,5S,7s)-9-methyl-3-oxa-9-azabicyclo[3.3.1]nonan-7-yl)-1-(thiazol-2-yl)-1H-pyrrolo[2,3-b]pyridine-3-carboxamide, 2,2,2-trifluoroacetic acid salt; 5-fluoro-N-((1R,5S,7s)-9-methyl-3-oxa-9-azabicyclo[3.3.1]nonan-7-yl)-1-(thiazol-4-yl)-1H-pyrrolo[2,3-b]pyridine-3-carboxamide, 2,2,2-trifluoroacetic acid salt; 5-fluoro-N-((1R,5S,7s)-9-methyl-3-oxa-9-azabicyclo[3.3.1]nonan-7-yl)-1-(thiazol-5-yl)-1H-pyrrolo[2,3-b]pyridine-3-carboxamide, 2,2,2-trifluoroacetic acid salt; N-((1R,5S,7s)-9-methyl-3-oxa-9-azabicyclo[3.3.1]nonan-7-yl)-1-(thiazol-5-yl)-1H-indazole-3-carboxamide, 2,2,2-trifluoroacetic acid salt;

1-(isothiazol-4-yl)-N-((1R,5S,7s)-9-methyl-3-oxa-9-azabicyclo[3.3.1]nonan-7-yl)-1H-indole-3-carboxamide, 2,2,2-trifluoroacetic acid salt; 1-(isothiazol-3-yl)-N-((1R,5S,7s)-9-methyl-3-oxa-9-azabicyclo[3.3.1]nonan-7-yl)-1H-indole-3-carboxamide, 2,2,2-trifluoroacetic acid salt; 1-(isothiazol-5-yl)-N-((1R,5S,7s)-9-methyl-3-oxa-9-azabicyclo[3.3.1]nonan-7-yl)-1H-indole-3-carboxamide, 2,2,2-trifluoroacetic acid salt; N-((1R,5S,7s)-9-methyl-3-oxa-9-azabicyclo[3.3.1]nonan-7-yl)-1-(oxazol-2-yl)-1H-indole-3-carboxamide, 2,2,2-trifluoroacetic acid salt; N-((1R,5S,7S)-9-methyl-3-oxa-9-azabicyclo[3.3.1]nonan-7-yl)-1-(pyridazin-4-yl)-1H-indole-3-carboxamide; N-((1R,5S,7S)-9-methyl-3-oxa-9-azabicyclo[3.3.1]nonan-7-yl)-1-(pyridazin-4-yl)-1H-indole-3-carboxamide; and (1R,5S,7S)-9-methyl-3-oxa-9-azabicyclo[3.3.1]nonan-7-yl 1-(pyrimidin-2-yl)-1H-indole-3-carboxylate.

Example 27

Synthesis of (1R,5S,7s)-3-oxa-9-azabicyclo[3.3.1]nonan-7-yl 1-(pyrazin-2-yl)-1H-indole-3-carboxylate, 2,2,2-trifluoroacetic acid salt

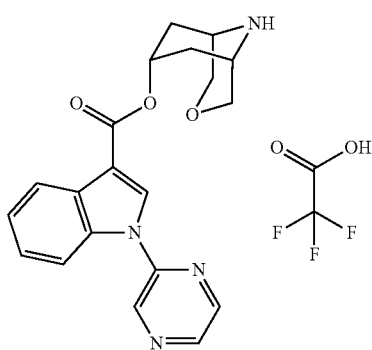 [SMILES: O=C(OC1CC2COCC(C1)N2)c1cn(-c2cnccn2)c2ccccc12 ; O=C(O)C(F)(F)F]

Step 1: (1R,5S,7s)-tert-butyl 7-((1-(pyrazin-2-yl)-1H-indole-3-carbonyl)oxy)-3-oxa-9-azabicyclo[3.3.1]nonane-9-carboxylate A solution of (1R,5S,7s)-tert-butyl 7-((1H-indole-3-carbonyl)oxy)-3-oxa-9-azabicyclo[3.3.1]nonane-9-carboxylate (36 mg, 0.093 mmol) in DMF (466 µl) was treated with sodium hydride (4.10 mg, 0.102 mmol, 60% suspension in mineral oil) at RT and the solution was stirred for 30 min. 2-fluoropyrazine (8.29 µl, 0.102 mmol) was then added, the vial capped and the resulting reaction mixture stirred at 90° C. for 4 h. The reaction mixture was quenched with a few drops of methanol, followed by ISCO purification (20% EtOAc/hexanes) to afford the title compound as a white solid.

Step 2: (1R,5S,7s)-3-oxa-9-azabicyclo[3.3.1]nonan-7-yl 1-(pyrazin-2-yl)-1H-indole-3-carboxylate, 2,2,2-trifluoroacetic acid salt A solution of (1R,5S,7s)-tert-butyl 7-((1-(pyrazin-2-yl)-1H-indole-3-carbonyl)oxy)-3-oxa-9-azabicyclo[3.3.1]nonane-9-carboxylate (30 mg, 0.065 mmol) in DCM (646 µl) was treated with TFA (74.6 µl, 0.969 mmol) dropwise at RT and the resulting reaction mixture was stirred for 3 h. ISCO purification (5% MeOH/DCM) afforded the title compound as a white solid. MS (ESI, pos. ion) m/z: 365.20 (M+1).

The following compound was prepared by a similar procedure: (1R,5S,7S)-3-oxa-9-azabicyclo[3.3.1]nonan-7-yl 1-(cyanomethyl)-1H-indole-3-carboxylate.

Example 28

Synthesis of (1R,5S,7s)-3-oxa-9-azabicyclo[3.3.1]nonan-7-yl 1-(2-cyanophenyl)-1H-indole-3-carboxylate, 2,2,2-trifluoroacetic acid salt

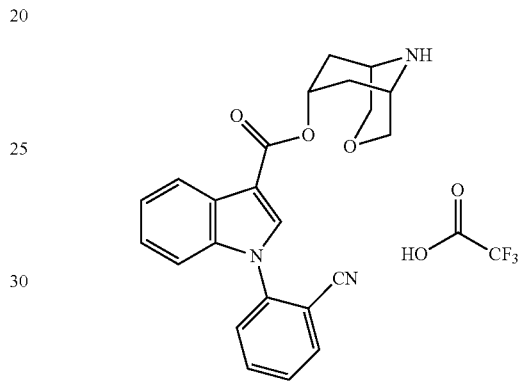

Step 1: (1R,5S,7s)-tert-butyl 7-((1-(2-cyanophenyl)-1H-indole-3-carbonyl)oxy)-3-oxa-9-azabicyclo[3.3.1]nonane-9-carboxylate A solution of (1R,5S,7s)-tert-butyl 7-((1H-indole-3-carbonyl)oxy)-3-oxa-9-azabicyclo[3.3.1]nonane-9-carboxylate (30 mg, 0.078 mmol) and 2-bromobenzonitrile (15.54 mg, 0.085 mmol) in toluene (155 µl) was treated with (1R,2R)—N1,N2-dimethylcyclohexane-1,2-diamine (2.53 µl, 0.016 mmol), potassium phosphate (36.3 mg, 0.171 mmol) and copper(I) iodide (4.44 mg, 0.023 mmol) and the resulting reaction mixture stirred at 110° C. for 12 h. HPLC purification afforded the title compound as an orange solid.

Step 2: (1R,5S,7s)-3-oxa-9-azabicyclo[3.3.1]nonan-7-yl 1-(2-cyanophenyl)-1H-indole-3-carboxylate, 2,2,2-trifluoroacetic acid salt.

A solution of (1R,5S,7s)-tert-butyl 7-((1-(2-cyanophenyl)-1H-indole-3-carbonyl)oxy)-3-oxa-9-azabicyclo[3.3.1]nonane-9-carboxylate 2,2,2-trifluoroacetate (14 mg, 0.023 mmol) in DCM (233 n1) was treated with TFA (17.93 µl, 0.233 mmol) at RT and the resulting reaction mixture stirred for 1 h. ISCO purification (10% MeOH/DCM) afforded the title compound as a white solid. MS (ESI, pos. ion) m/z: 388.20 (M+1).

The following compounds were prepared by a similar procedure, where Boc group was removed either with TFA or HCl:

(1R,5S,7s)-3-oxa-9-azabicyclo[3.3.1]nonan-7-yl 1-(3-cyanophenyl)-1H-indole-3-carboxylate, 2,2,2-trifluoroacetic acid salt; (1R,5S,7s)-3-oxa-9-azabicyclo[3.3.1]nonan-7-yl 1-(4-cyanophenyl)-1H-indole-3-carboxylate, 2,2,2-trifluoroacetic acid salt; (1R,5S,7s)-3-oxa-9-azabicyclo[3.3.1]nonan-7-yl 1-(isothiazol-4-yl)-1H-indole-3-carboxylate, 2,2,2-trifluoroacetic acid salt; (1R,5S,7s)-3-oxa-9-azabicyclo[3.3.1]nonan-7-yl 1-(isothiazol-3-yl)-1H-indole-3-carboxylate, 2,2,2-trifluoroacetic acid salt; (1R,5S,7s)-3-oxa-9-azabicyclo[3.3.1]nonan-7-yl 1-(isothiazol-5-yl)-1H-indole-3-carboxylate, 2,2,2-trifluoroacetic acid salt; (1R,5S,7s)-3-oxa-9-azabicyclo[3.3.1]nonan-7-yl; (1R,5S,7s)-3-oxa-9-azabicyclo[3.3.1]nonan-7-yl 1-(1-methyl-2-oxo-1,2-dihydropyridin-4-yl)-1H-indole-3-carboxylate, 2,2,2-trifluoroacetic acid salt; and (1R,5S,7s)-3-oxa-9-azabicyclo[3.3.1]nonan-7-yl 1-(oxazol-2-yl)-1H-indole-3-carboxylate, 2,2,2-trifluoroacetic acid salt.

Example 29

Synthesis of (1R,5S,7s)-9-methyl-3-oxa-9-azabicyclo[3.3.1]nonan-7-yl 1-(cyanomethyl)-7-fluoro-1H-pyrrolo[2,3-c]pyridine-3-carboxylate, 2,2,2-trifluoroacetic acid salt

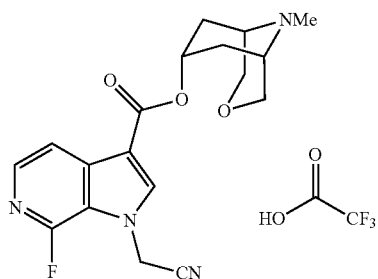 [SMILES: CN1C2COCC1CC(OC(=O)c1cn(CC#N)c3c(F)nccc13)C2 ; O=C(O)C(F)(F)F]

Step 1: (1R,5S,7s)-9-methyl-3-oxa-9-azabicyclo[3.3.1]nonan-7-yl 7-fluoro-1H-pyrrolo[2,3-c]pyridine-3-carboxylate Di(1H-imidazol-1-yl)methanone (113 mg, 0.696 mmol) was added to a solution of 7-fluoro-1H-pyrrolo[2,3-c]pyridine-3-carboxylic acid (104.5 mg, 0.580 mmol) in DMF (1160 µl) at RT. After 1 h, (1R,5S,7s)-9-methyl-3-oxa-9-azabicyclo[3.3.1]nonan-7-ol (182 mg, 1.160 mmol) was added to the mixture and the resulting brown solution was heated at 100° C. for 3 days. The reaction mixture was then directly purified by HPLC, followed by neutralization (with NaHCO₃) and prep-TLC (DCM/MeOH) to afford the title compound as a white solid.

Step 2: (1R,5S,7s)-9-methyl-3-oxa-9-azabicyclo[3.3.1]nonan-7-yl 1-(cyanomethyl)-7-fluoro-1H-pyrrolo[2,3-c]pyridine-3-carboxylate, 2,2,2-trifluoroacetic acid salt Sodium hydride (20.19 mg, 0.505 mmol, 60% suspension in mineral oil) was added to a solution of (1R,5S,7s)-9-methyl-3-oxa-9-azabicyclo[3.3.1]nonan-7-yl 7-fluoro-1H-pyrrolo[2,3-c]pyridine-3-carboxylate 2,2,2-trifluoroacetate (109.4 mg, 0.252 mmol) in DMF (841 µl) at RT. After 10 min, 2-bromoacetonitrile (17.58 µl, 0.252 mmol) was added to the mixture at RT. After 30 min, the mixture was directly purified by HPLC to afford the title compound as a white solid. MS (ESI, pos. ion) m/z: 359.15 (M+1).

Example 30

Synthesis of (1R,5S,7s)-9-methyl-3-oxa-9-azabicyclo[3.3.1]nonan-7-yl 5-cyano-1-(2-fluoroethyl)-1H-indole-3-carboxylate, 2,2,2-trifluoroacetic acid salt.

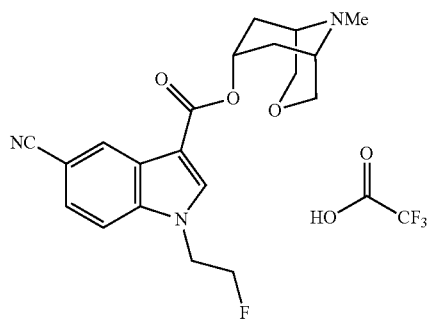 [SMILES: CN1C2COCC1CC(OC(=O)c1cn(CCF)c3ccc(C#N)cc13)C2 ; O=C(O)C(F)(F)F]

Step 1: (1R,5S,7s)-9-methyl-3-oxa-9-azabicyclo[3.3.1]nonan-7-yl 5-cyano-1H-indole-3-carboxylate, 2,2,2-trifluoroacetic acid salt 2,2,2-Trifluoroacetic anhydride (64.5 µl, 0.457 mmol) was added to a solution of 5-cyano-1H-indole-3-carboxylic acid (85 mg, 0.457 mmol) in toluene (1660 µl) and TFA (415 µl) at RT. After 15 min, (1R,5S,7s)-9-methyl-3-oxa-9-azabicyclo[3.3.1]nonan-7-ol (65.3 mg, 0.415 mmol) was added to the mixture. After 1 h, the mixture was directly purified by HPLC to afford the title compound as a colorless oil.

Step 2: (1R,5S,7s)-9-methyl-3-oxa-9-azabicyclo[3.3.1]nonan-7-yl 5-cyano-1-(2-fluoroethyl)-1H-indole-3-carboxylate, 2,2,2-trifluoroacetic acid salt Sodium hydride (6.28 mg, 0.157 mmol, 60% suspension in mineral oil) was added to a solution of (1R,5S,7s)-9-methyl-3-oxa-9-azabicyclo[3.3.1]nonan-7-yl 5-cyano-1H-indole-3-carboxylate 2,2,2-trifluoroacetate (30 mg, 0.068 mmol) in DMF (341 µl) at RT. After 10 min, 1-bromo-2-fluoroethane (11.27 mg, 0.089 mmol) was added to the mixture at RT. After 30 min, the reaction mixture was directly purified by HPLC to yield the title compound as a white solid. MS (ESI, pos. ion) m/z: 359.15 (M+1).

The following compound was prepared by a similar procedure:
(1R,5S,7s)-9-methyl-3-oxa-9-azabicyclo[3.3.1]nonan-7-yl 5-cyano-1-(6-fluoropyridazin-3-yl)-1H-indole-3-carboxylate.

Example 32

Synthesis of (1R,5S,7s)-9-methyl-3-oxa-9-azabicyclo[3.3.1]nonan-7-yl 1-(6-hydroxypyridazin-3-yl)-1H-indole-3-carboxylate, 2,2,2-trifluoroacetic acid salt

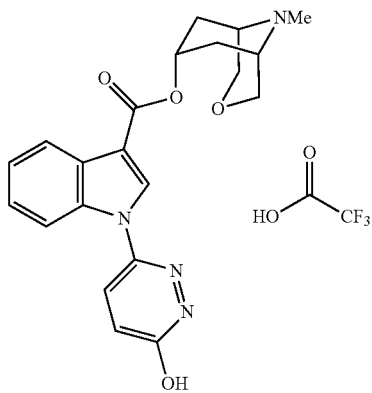 [SMILES: CN1C2COCC1CC(OC(=O)c1cn(-c3ccc(O)nn3)c3ccccc13)C2 ; O=C(O)C(F)(F)F]

Potassium trimethylsilanolate (5.83 mg, 0.045 mmol) was added to a solution of (1R,5S,7s)-9-methyl-3-oxa-9-azabicyclo[3.3.1]nonan-7-yl 1-(6-fluoropyridazin-3-yl)-1H-indole-3-carboxylate (18 mg, 0.045 mmol) in THF (227 µl) at RT. After 1 h, 2M aq KOH (100 uL) was added and the mixture was stirred at RT for 14 h. HPLC purification yielded the title compound as a white solid. MS (ESI, pos. ion) m/z: 395.20 (M+1).

Example 33

(1R,5S,7S)-9-methyl-3-oxa-9-azabicyclo[3.3.1]nonan-7-yl 1-(5-fluoropyrazin-2-yl)-1H-indole-3-carboxylate, 2,2,2-trifluoroacetic acid salt

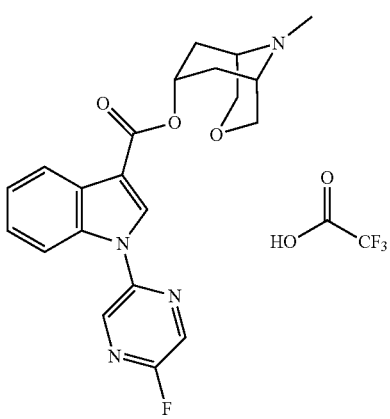 [SMILES: CN1C2COCC1CC(OC(=O)c1cn(-c3cnc(F)cn3)c3ccccc13)C2 ; O=C(O)C(F)(F)F]

A solution of (1R,5S,7S)-9-methyl-3-oxa-9-azabicyclo[3.3.1]nonan-7-yl 1-(5-chloropyrazin-2-yl)-1H-indole-3-carboxylate (10 mg, 0.024 mmol), 1,4,7,10,13,16-hexaoxacyclooctadecane (3.20 mg, 0.012 mmol) and potassium fluoride (4.22 mg, 0.073 mmol) was heated at 120° C. for 1 h. Direct HPLC purification gave the title compound as a white solid. MS (ESI, pos. ion) m/z: 397.20 (M+1).

Example 34

Synthesis of (1R,5S,7S)-9-methyl-3-oxa-9-azabicyclo[3.3.1]nonan-7-yl 1-(isothiazol-3-yl)-1H-indole-3-carboxylate, 2,2,2-trifluoroacetic acid salt

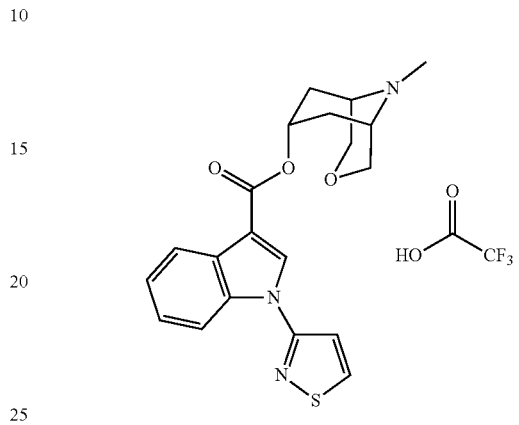

A solution of (1R,5S,7S)-9-methyl-3-oxa-9-azabicyclo[3.3.1]nonan-7-yl 1H-indole-3-carboxylate (200 mg, 0.666 mmol) and 3-bromoisothiazole (138 mg, 0.799 mmol) in toluene (Volume: 1332 µl) was treated with (1R,2R)—N1,N2-dimethylcyclohexane-1,2-diamine (32.6 µl, 0.200 mmol), potassium phosphate (306 mg, 1.398 mmol) and copper(I) iodide (38.0 mg, 0.200 mmol). The resulting reaction mixture was stirred at 120° C. overnight. HPLC purification afforded the title compound as a tan solid. MS (ESI, pos. ion) m/z: 384.3 (M+1).

Compound 189 in Table 1 above was synthesized by utilizing a similar procedure as described in Example 34 above.

BIOLOGICAL EXAMPLES

Biological Example 1

Inhibition of Ca Flux Activity of 5HT3 In Vitro Assay

The 5HT3 antagonist activity of the compounds of the invention was determined by measuring the ability of the compounds to inhibit the calcium flux activity of 3HT3a receptor expressed in HEK-293T cells. HEK-293T cells were transfected with the 5HT3a expression construct using Xtreme Gene 9 (Roche) in 150 mm tissue culture treated plates and incubated for 24 hours at 37° C. Cells were then split and plated at a density of 60K cells/well in poly-lysine coated, black 96-well plates with clear bottoms (BD Biosciences) and incubated overnight at 37° C. Growth media was removed and cells loaded with 200 uL calcium indicator dye in HBSS containing 20 mM HEPES (Calcium 5 Assay kit, Molecular Devices) and incubated at 37° C. for 1 hour. While cells were incubating, the 10× antagonist and agonist/antagonist addition plates were made. For 10× antagonist plate: half log serial dilutions (final concentrations range from $10^{-7}$ through $10^{-10}$ with the bottom well a negative, no ligand control) were made from test compounds in DMSO at a 1000× concentration and then diluted to 10× in HBSS/20 mM HEPES. For addition plate: 5HT was diluted to 100× in HBSS/20 mM HEPES (final concentration in the assay—216 nM) and 15 uL was added to each well of the addition plate, 15 uL of 10× compound was also added to the addition plate, and finally 120 uL of HBSS/20 mM HEPES (for a total of 150 uL). Cells were then removed from the incubator and equilibrated to room temperature for 10 minutes, then 22.5 uL of 10× test compounds were added in triplicate to the plates and incubated at room temperature for 10 minutes (Tropisetron was used as a positive control in every assay). Test plate and addition plate were loaded into the FlexStation III (Molecular Devices), and using the fluidics, 22.5 uL compound additions were made (at t=~17 seconds), and fluorescence was measured for 90 seconds, reading every 2.2 seconds. Data sets were analyzed as max minus min using Software Max Pro (Molecular Devices). $IC_{50}$ curves were generated using non-linear regression in GraphPad Prism.

Approximate $IC_{50}$ values of a representative number of compounds of the invention this assay are provided in the Table 2 below.

TABLE 2

| Cpd. No. from Table I above | IC50 [nM] | Cpd. No. from Table I above | IC50 [nM] | Cpd. No. from Table I above | IC50 [nM] |
|---|---|---|---|---|---|
| 1 | 2.13 | 2 | 1.71 | 3 | 1.03 |
| 4 | 1.4 | 5 | 1.35 | 6 | 2.33 |
| 7 | 0.49 | 8 | 0.68 | 9 | 1.8 |
| 10 | 0.57 | 11 | 0.95 | 12 | 0.45 |
| 13 | 0.93 | 14 | 3.71 | 15 | 0.53 |
| 16 | 3.25 | 17 | 4.39 | 18 | 4.06 |
| 19 | 7.72 | 20 | 0.4 | 21 | 0.40 |
| 22 | 1.13 | 24 | 1.06 | 25 | 3.88 |
| 26 | 0.54 | 27 | 0.89 | 28 | 1.08 |
| 29 | 0.95 | 30 | 0.20 | 31 | 1.29 |
| 32 | 1.38 | 33 | 14.41 | 34 | 0.74 |
| 35 | 0.54 | 36 | 0.50 | 37 | >1000 |
| 38 | 1.82 | 39 | 24.1 | 40 | 0.78 |
| 41 | 5.56 | 42 | 0.94 | 43 | 1.02 |
| 44 | 1.87 | 45 | 3.09 | 46 | 0.59 |
| 47 | 0.33 | 48 | 0.84 | 49 | 1.82 |
| 50 | 13.0 | 51 | 0.60 | 52 | 1.05 |
| 53 | 1.05 | 54 | 5.61 | 55 | 0.90 |
| 56 | 0.53 | 57 | >1000 | 58 | 0.24 |
| 59 | 2.36 | 60 | 0.44 | 61 | 1.0 |
| 62 | 0.75 | 63 | 0.49 | 64 | 1.43 |
| 65 | 4.09 | 66 | 1.07 | 67 | >1000 |
| 68 | 0.95 | 69 | 1.06 | 70 | 1.13 |
| 71 | 0.51 | 72 | 3.59 | 73 | 3.15 |
| 74 | 0.42 | 75 | 3.15 | 76 | 1.22 |
| 77 | 10.5 | 78 | 4.81 | 79 | 0.41 |
| 80 | 1.03 | 81 | 1.44 | 82 | >1000 |
| 83 | 1.04 | 84 | 1.64 | 85 | 1.04 |
| 86 | 2.48 | 87 | 0.18 | 88 | 0.22 |
| 89 | 0.66 | 90 | 0.75 | 91 | >1000 |
| 93 | 1.39 | 95 | 0.89 | 96 | 0.83 |
| 97 | 1.45 | 98 | 5.45 | 99 | 0.29 |
| 100 | 12.79 | 101 | >1000 | 102 | >1000 |
| 103 | 8.2 | 104 | >1000 | 105 | 34.13 |
| 107 | 1.1 | 108 | 1.05 | 109 | 1.11 |
| 110 |  | 111 | 0.77 | 112 | 0.53 |
| 113 | 0.23 | 116 | >1000 | 117 | 0.39 |
| 118 | 0.86 | 119 | 0.40 | 120 | 0.39 |
| 122 | 1.01 | 123 | 0.28 | 126 | 0.86 |
| 127 | 0.22 | 128 | 2.16 | 129 | 0.64 |
| 130 | 0.55 | 131 | 1.93 | 132 | 2.30 |
| 133 | 1.50 | 134 | 1.99 | 135 | 11.7 |
| 136 | 0.914 | 137 | 0.681 | 141 | 1.119 |
| 142 | 0.9457 | 143 | 0.4155 | 144 | 0.61 |
| 145 | 2.71 | 146 | 0.702 | 147 | 0.40 |
| 148 | 0.40 | 153 | 0.87 | 154 | 0.328 |
| 155 | 1.26 | 158 | 1.36 | 159 | 0.2985 |
| 160 | 0.746 | 161 | >1000 | 162 | 1.81 |
| 163 | 1.81 | 164 | 1.1795 | 165 | 1.533 |
| 168 | 1.165 | 169 | 0.5975 | 170 | 1.5 |

TABLE 2-continued

| Cpd. No. from Table I above | IC50 [nM] | Cpd. No. from Table I above | IC50 [nM] | Cpd. No. from Table I above | IC50 [nM] |
|---|---|---|---|---|---|
| 171 | 1.1055 | 172 | 2.89 | 174 | 2.065 |
| 175 | 0.861 | 177 | 3.219 | 178 | 1.027 |
| 180 | 5.914 | 181 | 1.10 | 182 | 1.62 |
| 183 | 1.27 | 184 | 1.25 | 185 | 3.06 |
| 186 | 1.50 | 187 | 1.18 | 188 | 1.75 |
| 189 | 0.46 | 190 | 0.75 |  |  |

Biological Example 2

Rodent Novel Object Recognition (NOR) Assay in Phencyclidine-Induced Cognitive Deficits Modeling Schizophrenia The aim of this study was to investigate the ability of the compounds of the invention to improve subchronic PCP-induced impairment in cognition memory using the NOR task in the rat, a paradigm of relevance to cognition in schizophrenia. Adult male Sprague-Dawley rats (250-350 g; Harlan, USA) were used for the experiments Animal were acclimated to the facility for 7 days prior to experimentation. Seven groups of 14 animals per group were used for the experiment. One group of animals received vehicle (0.9% saline twice daily) and the remaining six groups received PCP (2.5 mg/kg, s.c. twice daily) for 7 days, followed by 5-days drug free. On the test day, the animals were allowed to acclimate to the testing room for 30 min prior to initiation of experiments. Experiments were carried out in a white plexiglass chamber, designated as experimental arena. The arena was placed in a dark experimental room that was illuminated by a halogen lamp, providing a dim light to the arena.

Animals were placed in the arena for a 5 minute period to freely explore the test chamber in the absence of objects (habituation). Animals were then returned to their home cage immediately upon completion of habituation for a 120 min period. (1R,3R,5S)-8-Methyl-8-azabicyclo[3.2.1]octan-3-yl 1-(2,2,2-trifluoroethyl)-1H-indole-3-carboxylate (0.1, 1, 10 mg/kg s.c.), or vehicle (veh, saline) was administered 120 min prior to T1 and galantamine (5 mg/kg, i.p.) was administered 30 min prior to T1. Animals were returned to the arena which contained two identical objects (plastic balls) placed at one end of the arena (acquisition, T1), and allowed to explore for a 5 min period. The time spent exploring the two objects was recorded Animals were once again returned to the home cage for a period of 120 min (ITI).

ITI was followed by the retention phase (T2) where one of the objects presented in the first trial was replaced by a novel object and animals were allowed to explore for an additional 5 min period. Again, the time spent exploring the two objects was recorded.

For the retention phase, the differences between the time spent exploring the familiar object and the novel object were examined. All sessions were recorded and scored blindly for the time exploring objects. Exploration is defined as touching the object or directing nose towards object at a distance less that 2 cm. A minimal exploration criterion was used such that only animals with exploration time of greater than 5 seconds per object were included.

Comparisons of all treatment groups were conducted using a one-way ANOVA followed by a Bonferroni's post hoc test for multiple comparisons.

Results: Vehicle/vehicle-treated animals displayed a statistically significant discrimination between familiar (TF) and novel objects (TN) [27.99±2.77 (TN) versus 15.74±2.118 (TF)] at a 2 h ITI, indicative of good performance and/or lack or cognitive deficit. In contrast, the vehicle/PCP-treated animals displayed a statistically non-significant discrimination between familiar and novel objects [23.31±1.998 (TN) versus 17.13±1.112 (TF)]. Galantamine-treated animals, the positive control group, displayed a statistically significant discrimination between familiar and novel objects [22.8±2.2 (TN) versus 11.19±1.376 (TF)] at a 2 h ITI, indicative of reversal of the PCP-induced cognitive deficits. (1R,3R,5S)-8-methyl-8-azabicyclo[3.2.1]octan-3-yl 1-(2,2,2-trifluoroethyl)-1H-indole-3-carboxylate did not demonstrate a statistically significant discrimination between familiar and novel objects at 0.1 mg/kg [0.01 mg/kg 22.9±3.65 (TN) versus 12.5±2.152 (TF)] but demonstrated a statistically significant discrimination between familiar and novel objects at 1 and 10 mg/kg, [0.1 mg/kg: 25.3±2.51 (TN) versus 12.7±1.027 (TF)], [10 mg/kg 22.8±2.48 (TN) versus 9.831±1.53 (TF)], indicative of an attenuation of PCP-induced cognitive deficits.

Formulation Examples

The following are representative pharmaceutical formulations containing a compound of Formula (I).

Tablet Formulation

The following ingredients are mixed intimately and pressed into single scored tablets.

| Ingredient | Quantity per tablet |
| --- | --- |
| compound of this invention | 0.5-150 mg |
| cornstarch | 50 mg |
| croscarmellose sodium | 25 mg |
| lactose | 120 mg |
| magnesium stearate | 5 mg |

Capsule Formulation

The following ingredients are mixed intimately and loaded into a hard-shell gelatin capsule.

| Ingredient | Quantity per capsule |
| --- | --- |
| compound of this invention | 0.5-150 mg |
| lactose spray dried | 148 mg |
| magnesium stearate | 2 mg |

Injectable Formulation

Compound of the invention (e.g., compound 1) in 2% HPMC, 1% Tween 80 in DI water, pH 2.2 with MSA, q.s. to at least 20 mg/mL.

What is claimed is:
1. A compound of Formula (I):

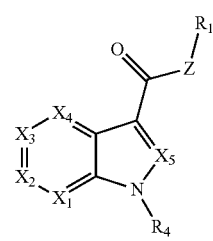

(I)

wherein:
Z is O or $NR_a$;
$R_a$ is hydrogen or $C_{1-6}$ alkyl;
$R_1$ is a ring of the formula (a), (d), (e), or (g) below:

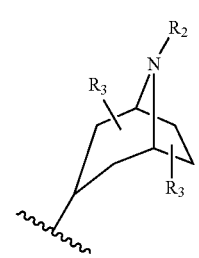

(a)

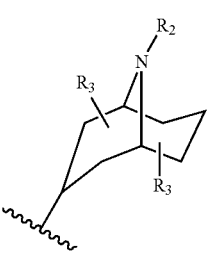

(d)

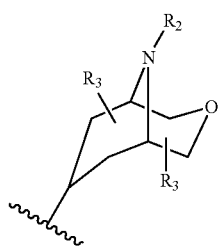

(e)

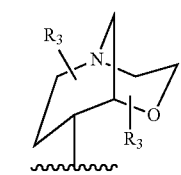

(f)

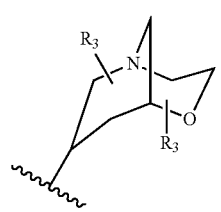

(g)

wherein:

R₂ is hydrogen, $C_{1-6}$ alkyl, or $C_{1-6}$ haloalkyl;

each R₃ is independently hydrogen, $C_{1-6}$ alkyl, $C_{1-6}$ alkoxy, $C_{1-6}$ haloalkoxy, or halo and can be present on any carbon atom in the rings;

R₄ is heteroaryl selected from the group consisting of furanyl, pyrrolyl, imidazolyl, oxazolyl, isoxazolyl, oxadiazolyl, thiazolyl, isothiazolyl, thiadiazolyl, triazolyl, tetrazolyl, pyrazinyl, and pyridazinyl, each R₄ heteroaryl is optionally substituted with one or two substituents independently selected from $C_{1-6}$ alkyl, $C_{1-6}$ haloalkyl, $C_{1-6}$ haloalkoxy, $C_{1-6}$ alkoxy, hydroxy, cyano, or halo;

all of X₁-X₄ are CR₅;

each R₅ is hydrogen;

X⁵ is CR⁶ where R⁶ is hydrogen, $C_{1-6}$ alkyl, or halo;

or a pharmaceutically acceptable salt thereof or N-oxide thereof.

2. The compound or pharmaceutically acceptable salt according to claim 1, wherein Z is O.

3. The compound or pharmaceutically acceptable salt according to claim 1, wherein Z is NH.

4. The compound or pharmaceutically acceptable salt according to claim 3, wherein R₁ is a ring of formula (a) or (d).

5. The compound or pharmaceutically acceptable salt according to claim 3, wherein R₁ is a ring of formula (e), (f), or (g).

6. The compound or pharmaceutically acceptable salt according to claim 3, wherein R₁ is a ring of formula (e).

7. The compound or pharmaceutically acceptable salt according to claim 6, wherein each R₃ is hydrogen.

8. The compound or pharmaceutically acceptable salt according to claim 7, wherein R₂ is methyl.

9. The compound or pharmaceutically acceptable salt according to claim 1, wherein X₅ is CR₆ and R₆ is hydrogen.

10. The compound according to claim 1 which is selected from:

N-((1R,5S,7S)-9-methyl-3-oxa-9-azabicyclo[3.3.1]nonan-7-yl)-1-(pyridazin-3-yl)-1H-indole-3-carboxamide;

N-((1R,5S,7S)-9-methyl-3-oxa-9-azabicyclo[3.3.1]nonan-7-yl)-1-(thiazol-2-yl)-1H-indole-3-carboxamide;

N-((1R,5S,7S)-9-methyl-3-oxa-9-azabicyclo[3.3.1]nonan-7-yl)-1-(thiazol-5-yl)-1H-indole-3-carboxamide;

N-((1R,5S,7S)-9-methyl-d₃-3-oxa-9-azabicyclo[3.3.1]nonan-7-yl)-1-(pyridazin-3-yl)-1H-indole-3-carboxamide;

(1R,5S,7S)-3-oxa-9-azabicyclo[3.3.1]nonan-7-yl 1-(thiazol-2-yl)-1H-indole-3-carboxylate;

N-((1R,5S,7S)-9-methyl-3-oxa-9-azabicyclo[3.3.1]nonan-7-yl)-1-(pyrazin-2-yl)-1H-indole-3-carboxamide;

N-((1R,5S,7S)-9-methyl-d₃-3-oxa-9-azabicyclo[3.3.1]nonan-7-yl)-1-(pyrazin-2-yl)-1H-indole-3-carboxamide;

(1R,5S,7s)-3-oxa-9-azabicyclo[3.3.1]nonan-7-yl 1-(pyridazin-3-yl)-1H-indole-3-carboxylate;

(1R,5S,7s)-9-methyl-3-oxa-9-azabicyclo[3.3.1]nonan-7-yl 1-(6-fluoropyridazin-3-yl)-1H-indole-3-carboxylate;

(1R,5S,7s)-3-oxa-9-azabicyclo[3.3.1]nonan-7-yl 1-(pyrazin-2-yl)-1H-indole-3-carboxylate;

(1R,5S,7s)-3-oxa-9-azabicyclo[3.3.1]nonan-7-yl 1-(isothiazol-4-yl)-1H-indole-3-carboxylate;

1-(isothiazol-4-yl)-N-((1R,5S,7s)-9-methyl-3-oxa-9-azabicyclo[3.3.1]nonan-7-yl)-1H-indole-3-carboxamide;

(1R,5S,7s)-3-oxa-9-azabicyclo[3.3.1]nonan-7-yl 1-(isothiazol-3-yl)-1H-indole-3-carboxylate;

1-(isothiazol-3-yl)-N-((1R,5S,7s)-9-methyl-3-oxa-9-azabicyclo[3.3.1]nonan-7-yl)-1H-indole-3-carboxamide;

1-(1-methyl-1H-imidazol-5-yl)-N-((1R,5S,7s)-9-methyl-3-oxa-9-azabicyclo[3.3.1]nonan-7-yl)-1H-indole-3-carboxamide;

(1R,5S,7s)-3-oxa-9-azabicyclo[3.3.1]nonan-7-yl 1-(isothiazol-5-yl)-1H-indole-3-carboxylate;

1-(isothiazol-5-yl)-N-((1R,5S,7s)-9-methyl-3-oxa-9-azabicyclo[3.3.1]nonan-7-yl)-1H-indole-3-carboxamide;

(1R,5S,7s)-9-methyl-3-oxa-9-azabicyclo[3.3.1]nonan-7-yl 1-(6-hydroxypyridazin-3-yl)-1H-indole-3-carboxylate;

(1R,5S,7s)-3-oxa-9-azabicyclo[3.3.1]nonan-7-yl 1-(oxazol-2-yl)-1H-indole-3-carboxylate;

N-((1R,5S,7s)-9-methyl-3-oxa-9-azabicyclo[3.3.1]nonan-7-yl)-1-(oxazol-2-yl)-1H-indole-3-carboxamide;

(1R,5S,7S)-9-methyl-3-oxa-9-azabicyclo[3.3.1]nonan-7-yl 1-(pyrazin-2-yl)-1H-indole-3-carboxylate;

(1R,5S,7S)-9-methyl-3-oxa-9-azabicyclo[3.3.1]nonan-7-yl 1-(isothiazol-3-yl)-1H-indole-3-carboxylate;

(1R,5S,7S)-9-methyl-3-oxa-9-azabicyclo[3.3.1]nonan-7-yl 1-(thiazol-5-yl)-1H-indole-3-carboxylate;

(1R,5S,7S)-9-methyl-3-oxa-9-azabicyclo[3.3.1]nonan-7-yl 1-(5-fluoropyrazin-2-yl)-1H-indole-3-carboxylate;

N-((1R,5S,7S)-3-oxa-9-azabicyclo[3.3.1]nonan-7-yl)-1-(isothiazol-4-yl)-N-methyl-1H-indole-3-carboxamide;

1-(isothiazol-4-yl)-N-methyl-N-((1R,5S,7S)-9-methyl-3-oxa-9-azabicyclo[3.3.1]nonan-7-yl)-1H-indole-3-carboxamide; and N-((1R,5S,7S)-9-methyl-3-oxa-9-azabicyclo[3.3.1]nonan-7-yl)-1-(pyridazin-4-yl)-1H-indole-3-carboxamide;

or a pharmaceutically acceptable salt of each above mentioned compound.

11. A pharmaceutical composition comprising a compound as defined in claim 1, or pharmaceutically acceptable salt thereof, and a pharmaceutically acceptable excipient.

* * * * *